United States Patent
Markwalder et al.

(10) Patent No.: US 9,895,330 B2
(45) Date of Patent: Feb. 20, 2018

(54) IDO INHIBITORS

(71) Applicant: BRISTOL-MYERS SQUIBB COMPANY, Princeton, NJ (US)

(72) Inventors: Jay A Markwalder, Lahaska, PA (US); James Aaron Balog, Lambertville, NJ (US); Audris Huang, New Hope, PA (US); Steven P Seitz, Swarthmore, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/903,091

(22) PCT Filed: Jul. 10, 2014

(86) PCT No.: PCT/US2014/046066
§ 371 (c)(1),
(2) Date: Jan. 6, 2016

(87) PCT Pub. No.: WO2015/006520
PCT Pub. Date: Jan. 15, 2015

(65) Prior Publication Data
US 2016/0143870 A1    May 26, 2016

Related U.S. Application Data

(60) Provisional application No. 61/844,897, filed on Jul. 11, 2013.

(51) Int. Cl.
| | | |
|---|---|---|
| C07C 233/55 | (2006.01) |
| C07D 257/04 | (2006.01) |
| C07D 401/10 | (2006.01) |
| C07D 401/12 | (2006.01) |
| C07D 403/10 | (2006.01) |
| C07D 409/12 | (2006.01) |
| C07D 413/12 | (2006.01) |
| C07D 487/08 | (2006.01) |
| C07D 405/12 | (2006.01) |
| A61K 31/196 | (2006.01) |
| A61K 31/41 | (2006.01) |
| A61K 31/454 | (2006.01) |
| A61K 31/4439 | (2006.01) |
| A61K 31/422 | (2006.01) |
| A61K 31/4155 | (2006.01) |
| A61K 31/5377 | (2006.01) |
| C07D 417/12 | (2006.01) |
| C07D 261/08 | (2006.01) |
| C07C 255/57 | (2006.01) |
| A61K 45/06 | (2006.01) |
| A61K 31/427 | (2006.01) |
| A61N 5/10 | (2006.01) |

(52) U.S. Cl.
CPC ............ *A61K 31/196* (2013.01); *A61K 31/41* (2013.01); *A61K 31/4155* (2013.01); *A61K 31/422* (2013.01); *A61K 31/427* (2013.01); *A61K 31/4439* (2013.01); *A61K 31/454* (2013.01); *A61K 31/5377* (2013.01); *A61K 45/06* (2013.01); *A61N 5/10* (2013.01); *C07C 233/55* (2013.01); *C07C 255/57* (2013.01); *C07D 257/04* (2013.01); *C07D 261/08* (2013.01); *C07D 401/10* (2013.01); *C07D 401/12* (2013.01); *C07D 403/10* (2013.01); *C07D 405/12* (2013.01); *C07D 409/12* (2013.01); *C07D 413/12* (2013.01); *C07D 417/12* (2013.01); *C07D 487/08* (2013.01); *C07C 2601/14* (2017.05)

(58) Field of Classification Search
None
See application file for complete search history.

(56) References Cited

U.S. PATENT DOCUMENTS

2016/0022619 A1    1/2016  Balog et al.

FOREIGN PATENT DOCUMENTS

| WO | WO2004/099168 A2 | 11/2004 |
| WO | WO2007/130780 A2 | 11/2007 |
| WO | WO2009/070516 A1 | 6/2009 |
| WO | WO2011/056652 A1 | 5/2011 |
| WO | WO2014/150677 A1 | 9/2014 |

OTHER PUBLICATIONS

Eduard Dolusic et al. "Indoleamine 2,3-dioxygenase inhibitors: a patent review (2008-2012)", Expert Opinion on Therapeutic Patents, vol. 23, No. 10, pp. 1367-1381, Oct. 1, 2013.

*Primary Examiner* — Emily Bernhardt
(74) *Attorney, Agent, or Firm* — Serena Farquharson-Torres; Elliott Korsen

(57) ABSTRACT

There are disclosed compounds of Formula (I) that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

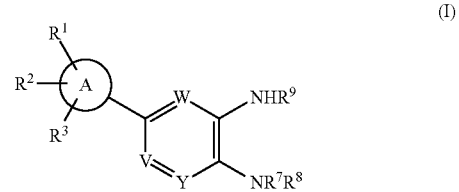

10 Claims, No Drawings

IDO INHIBITORS

CROSS-REFERENCE TO RELATED APPLICATIONS

This application claims the benefit of U.S. Provisional Application No. 61/844,897, filed Jul. 11, 2013, the disclosure of which is incorporated herein by reference in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. It is required for the biosynthesis of the neurotransmitter serotonin, the synthesis of the cofactor nicotinamide adenine dinucleotide (NAD), and is an important component in the immune system response ("immune escape") to tumors. Depletion of levels of tryptophan is associated with adverse effects on the proliferation and function of lymphocytes and diminished immune system response.

The enzyme indoleamine-2,3-deoxygenase (IDO) is overexpressed in many human tumors. IDO catalyzes the initial, rate-limiting step in the conversion of tryptophan to N-formylkynurenime. Moreover, IDO has been implicated in neurologic and psychiatric disorders including mood disorders as well as other chronic diseases characterized by IDO activation and tryptophan degradation such as viral infections, for example, AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting the function of IDO would be an important addition for the treatment of patients with diseases or conditions affected by the activity of the enzyme.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO inhibition, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides compounds of Formula (I)

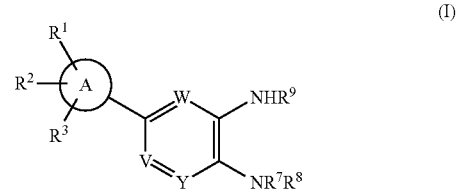

wherein:
W is $CR^4$ or N,
V is $CR^5$ or N, and
Y is $CR^6$ or N;

is optionally substituted phenyl or optionally substituted heteroaryl, $R^1$ is COOH, optionally substituted heterocyclyl, $-NHSO_2R^{20}$,

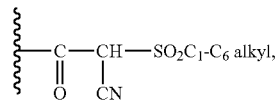

$-CONHSO_2R^{21}$, $-CONHCOOR^{22}$ or $-SO_2NHCOR^{23}$;
$R^2$ and $R^3$ are independently H, optionally substituted $C_1$-$C_6$ alkyl, optionally substituted $C_1$-$C_6$ alkoxy or optionally substituted $N(C_1$-$C_6$ alkyl$)_2$;
$R^4$, $R^5$ and $R^6$ are independently H, halo, CN, OH, optionally substituted $C_1$-$C_6$ alkyl or optionally substituted $C_1$-$C_6$ alkoxy;
$R^7$ and $R^8$ are independently H, optionally substituted $C_1$-$C_6$ alkyl, optionally substituted $C_1$-$C_6$ alkoxy, optionally substituted $C_3$-$C_8$ cycloalkyl, optionally substituted di-deutero-$C_1$-$C_{10}$-alkyl, optionally substituted $C_2$-$C_{10}$ alkynyl, optionally substituted 5- to 7-membered monocyclic heteroaryl, optionally substituted 8- to 10-membered bicyclic heteroaryl, optionally substituted aryl $C_1$-$C_6$ alkyl, optionally substituted $C_2$-$C_6$ alkenyl, or optionally substituted $C_5$-$C_8$ cycloalkenyl, provided that only one of $R^7$ and $R^8$ is H;

or $R^7$ and $R^8$ are taken together with the nitrogen to which they are attached to form an optionally substituted 5- to 10-membered monocyclic, bicyclic or tricyclic heterocyclic ring, or an optionally substituted 5- to 7-membered monocyclic heteroaryl ring;

$R^9$ is

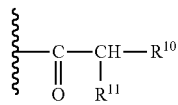

or —COOR$^{12}$;

$R^{10}$ is CN, optionally substituted aryl, optionally substituted benzodioxolyl optionally substituted $C_1$-$C_6$ alkyl, optionally substituted 5- to 7-membered monocyclic heteroaryl, optionally substituted mono- or di-$C_1$-$C_6$-alkyl-substituted 5- to 7-membered monocyclic heteroaryl, optionally substituted arylsulfonyl, optionally substituted di-$C_1$-$C_6$-alkylamino, optionally substituted 5- to 7-membered monocyclic heterocyclo, optionally substituted $C_3$-$C_8$ cycloalkyl, optionally substituted di-$C_1$-$C_{10}$-alkylaminocarbonyl-$C_1$-$C_6$-alkyl, optionally substituted aryloxy, optionally substituted $C_1$-$C_6$ alkoxy, optionally substituted $C_1$-$C_6$ alkylsulfonyl, optionally substituted $C_2$-$C_6$ alkenyl, optionally substituted $C_2$-$C_6$ alkynyl, optionally substituted $C_5$-$C_8$ cycloalkenyl, or optionally substituted 1-hydroxybenzyl;

wherein the optional substitutents, where possible, are 1 or 2 groups selected from H, OH, CN, optionally substituted $C_1$-$C_6$ alkyl, halo, aryl, optionally substituted $C_1$-$C_6$ alkoxy, aryloxy or dialkylamino;

$R^{11}$ is H, OH, optionally substituted $C_1$-$C_6$ alkoxy, or —OCOC$_1$-$C_6$ alkyl;

$R^{12}$ is optionally substituted aryl, optionally substituted $C_1$-$C_6$ alkyl or benzodioxolyl;

wherein the optional substitutents, where possible, are 1 or 2 groups selected from H, OH, halo, optionally substituted aryl, optionally substituted $C_1$-$C_6$ alkyl, optionally substituted $C_1$-$C_6$ alkoxy, NO$_2$ or aryl-$C_1$-$C_{10}$-alkoxy;

$R^{20}$ is optionally substituted $C_1$-$C_6$ alkyl;

$R^{21}$ is optionally substituted $C_1$-$C_6$ alkyl or optionally substituted $C_3$-$C_8$ cycloalkyl;

$R^{22}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

$R^{23}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

and/or a stereoisomer, a tautomer or a pharmaceutically acceptable salt thereof.

In a second aspect, the invention provides a compound of Formula (II) within the scope of the first aspect

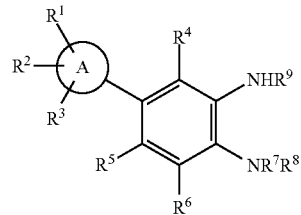

wherein:

is optionally substituted phenyl or optionally substituted heteroaryl, $R^1$ is COOH, optionally substituted heterocyclyl, —NHSO$_2$R$^{20}$,

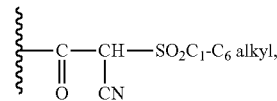

—CONHSO$_2$R$^{21}$, —CONHCOOR$^{22}$ or —SO$_2$NHCOR$^{23}$;

$R^2$ and $R^3$ are independently H, optionally substituted $C_1$-$C_6$ alkyl, optionally substituted $C_1$-$C_6$ alkoxy or optionally substituted N($C_1$-$C_6$ alkyl)$_2$;

$R^4$ and $R^5$ are independently H, halo, CN, OH, optionally substituted $C_1$-$C_6$ alkyl or optionally substituted $C_1$-$C_6$ alkoxy;

$R^6$ is H;

$R^7$ and $R^8$ are independently H, optionally substituted $C_1$-$C_6$ alkyl, optionally substituted $C_1$-$C_6$ alkoxy, optionally substituted $C_3$-$C_8$ cycloalkyl, optionally substituted di-deutero-$C_1$-$C_{10}$-alkyl, optionally substituted $C_2$-$C_{10}$ alkynyl, optionally substituted 5- to 7-membered monocyclic heteroaryl, optionally substituted 8- to 10-membered bicyclic heteroaryl, optionally substituted aryl $C_1$-$C_6$ alkyl, optionally substituted $C_2$-$C_6$ alkenyl, or optionally substituted $C_5$-$C_8$ cycloalkenyl;

provided that only one of $R^7$ and $R^8$ is H;

or $R^7$ and $R^8$ are taken together with the nitrogen to which they are attached to form an optionally substituted 5- to 10-membered monocyclic, bicyclic or tricyclic heterocyclic ring, or an optionally substituted 5- to 7-membered monocyclic heteroaryl ring;

$R^9$ is

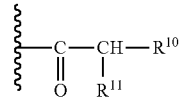

or —COOR$^{12}$;

$R^{10}$ is CN, optionally substituted aryl, optionally substituted benzodioxolyl optionally substituted $C_1$-$C_6$ alkyl, optionally substituted 5- to 7-membered monocyclic heteroaryl, optionally substituted mono- or di-$C_1$-$C_6$-alkyl-substituted 5- to 7-membered monocyclic heteroaryl, optionally substituted arylsulfonyl, optionally substituted di-$C_1$-$C_6$-alkylamino, optionally substituted 5- to 7-membered monocyclic heterocyclo, optionally substituted $C_3$-$C_8$ cycloalkyl, optionally substituted di-$C_1$-$C_{10}$-alkylaminocarbonyl-$C_1$-$C_6$-alkyl, optionally substituted aryloxy, optionally substituted $C_1$-$C_6$ alkoxy, optionally substituted $C_1$-$C_6$ alkylsulfonyl, optionally substituted $C_2$-$C_6$ alkenyl, optionally substituted $C_2$-$C_6$ alkynyl, optionally substituted $C_5$-$C_8$ cycloalkenyl, or optionally substituted 1-hydroxybenzyl;

wherein the optional substitutents, where possible, are 1 or 2 groups selected from H, OH, CN, optionally substituted $C_1$-$C_6$ alkyl, halo, aryl, optionally substituted $C_1$-$C_6$ alkoxy, aryloxy or dialkylamino;

$R^{11}$ is H, OH, optionally substituted $C_1$-$C_6$ alkoxy or —OCOC$_1$-$C_6$ alkyl;

$R^{12}$ is optionally substituted aryl, optionally substituted $C_1$-$C_6$ alkyl or benzodioxolyl;

wherein the optional substitutents, where possible, are 1 or 2 groups selected from H, OH, halo, optionally substituted aryl, optionally substituted $C_1$-$C_6$ alkyl, optionally substituted $C_1$-$C_6$ alkoxy, $NO_2$ or aryl-$C_1$-$C_{10}$-alkoxy;

$R^{20}$ is optionally substituted $C_1$-$C_6$ alkyl;

$R^{21}$ is optionally substituted $C_1$-$C_6$ alkyl or optionally substituted $C_3$-$C_8$ cycloalkyl;

$R^{22}$ is optionally substituted $C_1$-$C_6$ alkyl, optionally substituted $C_3$-$C_8$ cycloalkyl, optionally substituted $C_2$-$C_6$ alkenyl or optionally substituted $C_2$-$C_6$ alkynyl;

$R^{23}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

and/or a stereoisomer, a tautomer or a pharmaceutically acceptable salt thereof.

In a third aspect, the invention provides a compound of Formula (I) within the scope of the first and second aspects wherein

is phenyl, and/or a stereoisomer, a tautomer or a pharmaceutically acceptable salt thereof.

In a fourth aspect, the invention provides a compound of Formula (I) within the scope of the first through third aspects wherein:

$R^1$ is tetrazol-5-yl or COOH;
$R^2$ is H or halo; and
$R^3$ is H.

and/or a stereoisomer, a tautomer or a pharmaceutically acceptable salt thereof.

In a fifth aspect, the invention provides a compound of Formula (I) within the scope of the previously mentioned aspects wherein:

$R^7$ and $R^8$ are independently optionally substituted $C_1$-$C_6$ alkyl, $C_1$-$C_6$ alkoxy, optionally substituted aryl $C_1$-$C_6$ alkyl, optionally substituted $C_1$-$C_6$ alkyl aryl $C_1$-$C_6$ alkyl, optionally substituted $C_1$-$C_6$-alkoxy aryl-$C_1$-$C_6$-alkyl, 5- to 6-membered heteroaryl-$C_1$-$C_6$-alkyl or optionally substituted $C_3$-$C_8$ cycloalkyl;

or $R^7$ and $R^8$ are taken together with the nitrogen to which they are attached to form

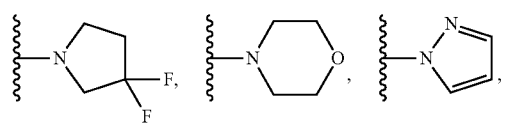

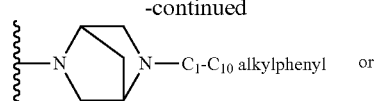

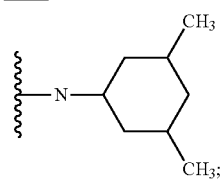

and
$R^9$ is

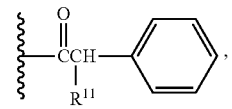

or —COOR$^{12}$;
$R^{11}$ is H or $C_1$-$C_6$ alkanoyl; and
$R^{12}$ is naphthyl, nitroaryl, phenyl, $C_1$-$C_6$ alkylphenyl, $C_1$-$C_6$ alkoxyphenyl,

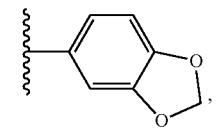 [SMILES: *c1ccc2c(c1)OCO2]

$C_1$-$C_6$ alkoxy(halo)phenyl, halophenyl, or phenyl-$C_1$-$C_6$-alkoxyphenyl;

and/or a stereoisomer, a tautomer or a pharmaceutically acceptable salt thereof.

In a sixth aspect, the invention provides a compound of Formula (III)

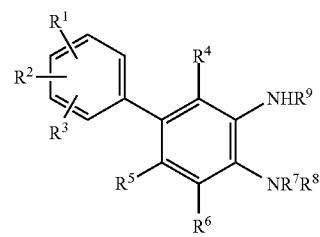

(III)

wherein:
$R^1$ is optional substituted tetrazol-5-yl or COOH;
$R^2$ is H or halo;
$R^3$ is H or halo;
$R^4$ is H or halo;
$R^5$ is H or halo;
$R^6$ is H or halo;
$R^7$ and $R^8$ are independently optionally substituted $C_1$-$C_6$ alkyl, $C_1$-$C_6$ alkoxy, optionally substituted aryl $C_1$-$C_6$ alkyl, optionally substituted $C_1$-$C_6$ alkyl aryl $C_1$-$C_6$ alkyl, optionally substituted $C_1$-$C_6$-alkoxy aryl-$C_1$-$C_6$-alkyl, 5- to 6-membered heteroaryl-$C_1$-$C_6$-alkyl or optionally substituted $C_3$-$C_8$ cycloalkyl;

or R$^7$ and R$^8$ together with the nitrogen to which they are attached form a 5- to 10-membered monocyclic or bicyclic heterocyclo ring optionally substituted with 1 or 2 groups which are halo, phenyl-C$_1$-C$_6$-alkyl, or C$_1$-C$_6$ alkyl or a 5- to 7-membered monocyclic heteroaryl ring;

R$^9$ is

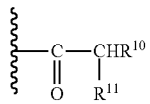

or —COOR$^{12}$;

R$^{10}$ is optionally substituted C$_1$-C$_6$ alkyl, optionally substituted C$_1$-C$_6$ alkylphenyl, optionally substituted aryl, optionally substituted C$_1$-C$_6$ alkoxyphenyl,

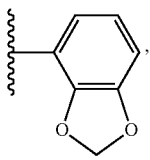 [SMILES: *c1cccc2c1OCO2]

C$_1$-C$_6$-alkoxy(trihalo-C$_1$-C$_6$-alkyl)phenyl, optionally substituted aryl-C$_1$-C$_6$-alkyl, cyano, optionally substituted 5- to 7-membered monocyclic heteroaryl, arylsulfonyl, C$_3$-C$_8$ cycloalkyl, di-C$_1$-C$_6$-alkylamino, 5- to 7-membered monocyclic heterocyclo, phenoxyphenyl, C$_1$-C$_6$ alkylphenyloxy, di-C$_1$-C$_6$-alkylaminocarbonyl-C$_1$-C$_6$-alkyl, C$_1$-C$_6$ alkylsulfonyl or C$_1$-C$_6$-alkoxy-C$_1$-C$_6$-alkoxy, R$^{11}$ is H, C$_1$-C$_6$ alkylCO— or OH;

R$^{12}$ is selected from C$_1$-C$_6$ alkylaryl, C$_1$-C$_6$-alkoxy-C$_1$-C$_6$-alkyl, 5- to 7-membered monocyclic heteroaryl, aryl-C$_1$-C$_6$-alkyl, optionally substituted aryl, C$_1$-C$_6$ alkoxyaryl, benzodioxolyl, optionally substituted (C$_1$-C$_6$ alkoxy)aryl, or aryl-C$_1$-C$_6$-alkoxyaryl;

and/or a stereoisomer, a tautomer or a pharmaceutically acceptable salt thereof.

In another aspect, the invention provides a compound of Formula (III) within the scope of one or more previous aspects of the invention wherein:

R$^9$ is

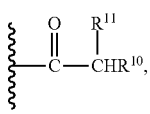

where R$^{11}$ is H or OH; and
R$^{10}$ is CN,

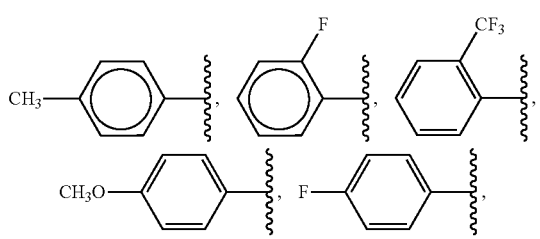

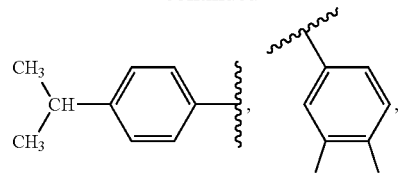

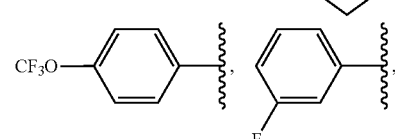

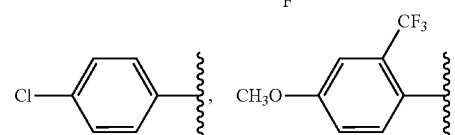

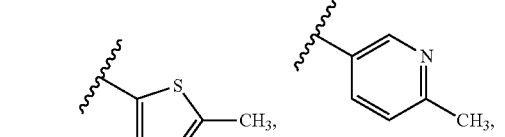

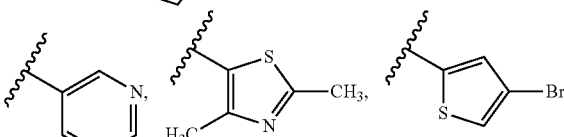

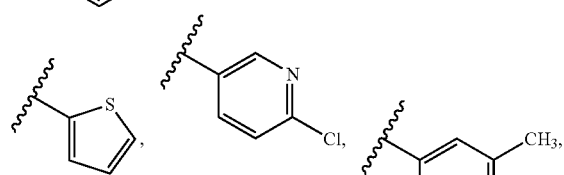

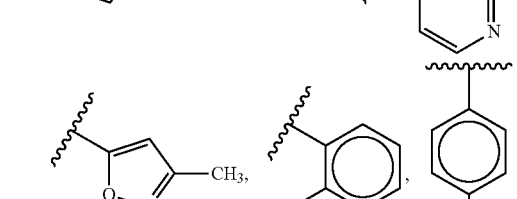

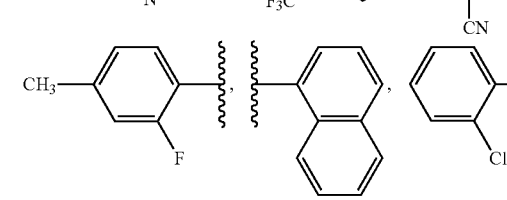

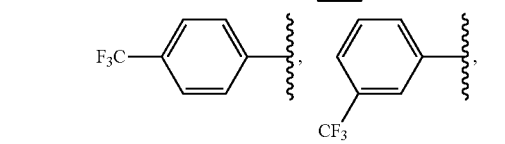

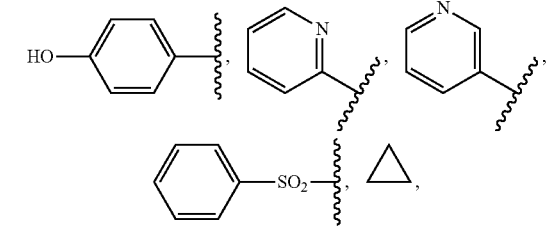

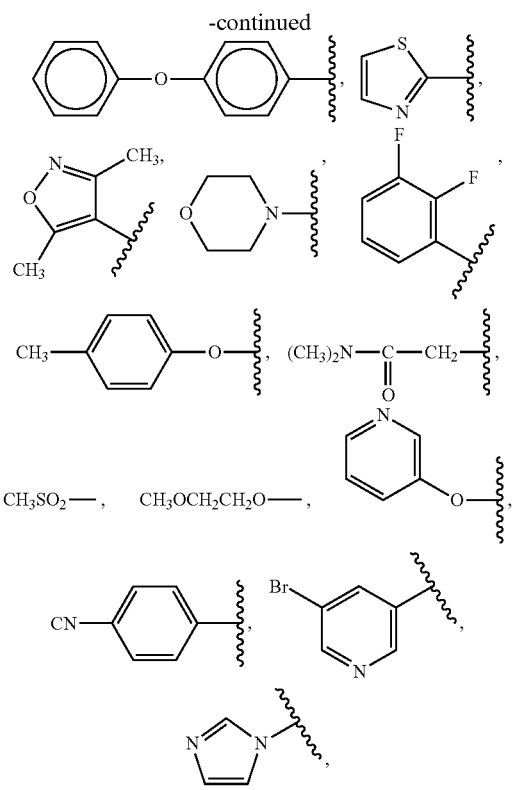

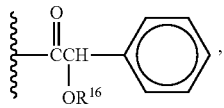

where R^16 is CH_3CO— or H;
and/or a pharmaceutically acceptable salt thereof, a tautomer thereof or stereoisomer thereof.

In yet another aspect, the invention provides a compound of Formula (III) within the scope of the previously mentioned aspects of the invention wherein:

R^9 is —COOR^{12}, where R^{12} is

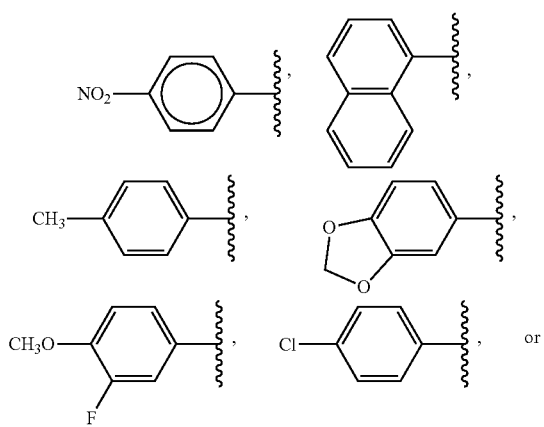

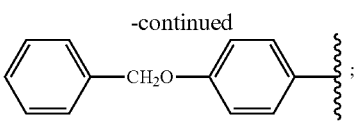

and/or a pharmaceutically acceptable salt thereof, a tautomer thereof or stereoisomer thereof.

In another aspect, the invention provides a compound selected from the exemplified examples within the scope of the previous aspects, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO $IC_{50}$ values ≤250 nM.

In another embodiment, the compounds of the invention have human IDO $IC_{50}$ values ≤50 nM.

In another embodiment, the compounds of the invention have human IDO $IC_{50}$ values ≤20 nM.

In another embodiment, the compounds of the invention have human IDO $IC_{50}$ values ≤10 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $—SO_2NH_2$, substituted sulfonamido, nitro, cyano, carboxy, carbamyl, e.g. $—CONH_2$, substituted carbamyl e.g.

—CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol ⌅— is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", "or aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

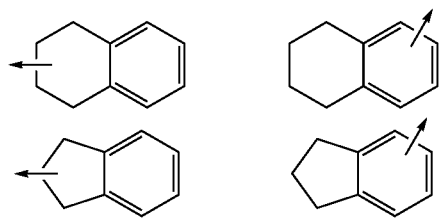

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or prop ionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

VI. Methods of Preparation

The compounds of the present invention may be prepared by methods such as those illustrated in the following Schemes utilizing transformations known to those skilled in the art. Solvents, temperatures, pressures, and other reaction conditions may readily be selected by one of ordinary skill in the art. Starting materials are commercially available or have been described in the chemical literature and can be readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these transformations can be found in Smith, M. B. et al., *March's Advanced Organic Chemistry Reactions, Mechanisms, and Structure*, Fifth Edition, Wiley-Interscience, New York, publ. (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is: Greene, T. W. et al., *Protective Groups in Organic Synthesis*, Third Edition, Wiley-Interscience, New York, publ. (1999).

Referring to the following Schemes, treatment of compounds (i) where X is Cl, Br or I and Q is halo with amines $HNR^7R^8$ (Scheme 1) and a suitable base in a solvent such as THF, DMF, NMP, dioxane or the like affords intermediates (vii). Generally heating is required. Suitable bases include, but are not limited to aliphatic tertiary amines, sodium or potassium carbonate, or an excess of the reacting primary or secondary amine $HNR^7R^8$. Reduction of the nitro group in compounds (vii) to afford anilines (viii) can be effected by various means including catalytic hydrogenation and dissolving metal reductions both in their various forms. See House, H. O., *Modern Synthetic Reactions*, Second Edition, W. A. Benjamin, Inc., Menlo Park, Calif., publ. (1972). A preferred method for effecting this reduction without removal of the halogen substituent X involves stirring a solution of the nitroaromatic in a wet alcoholic solvent with an acid such as ammonium chloride and finely divided zinc. Coupling of (viii) with arylboronic acids or esters, preferably under the conditions of Suzuki (See Kotha, S. et al., *Tetrahedron*, 58:9633-9695 (2002)) affords compounds IA of the invention ($R^9$=H). Typically, this reaction is performed by heating the halide and the boronic acid or ester at a temperature of about 95° C. with a base such as aqueous tribasic sodium or potassium phosphate or sodium or potassium carbonate in a solvent such as dioxane, DMF, THF, or NMP using a catalyst such as tetrakis(triphenylphosphine) palladium or $Cl_2Pd(dppf)$. Many variations on this reaction involving the use of different temperatures, solvents, bases, anhydrous conditions, catalysts, boronate derivatives, and halide surrogates such as triflates are known to those skilled in the art of organic/medicinal chemistry. Recently, mild conditions have been reported for the coupling of sensitive boronic acid derivatives. See: Kinzel, T. et al., *J. Am. Chem. Soc.*, 132(40):14073-14075 (2010). Related coupling reactions for the conversion of (viii) and other aryl halide intermediates described in later schemes into compounds of the invention include the Heck (olefin) (*J. Am. Chem. Soc.*, 96(4):1133-1136 (1974)), Stille (organostannane) (*Synthesis*, 803-815 (1992)), Sonogashira (acetylene) (Sonogashira, K. et al., *Tetrahedron Lett.*, 16(50):4467-4470 (1975)), and Negishi (organozinc) (*Aldrichimica Acta.*, 38(3):71-78 (2005)) coupling reactions.

As shown below in Scheme 1, Compound IA can be coupled with a carboxylic acid

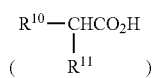

to form compound IB

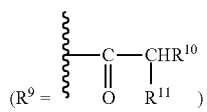

of the invention or reacted with a chloridate ($R^{12}OCOCl$) to form compound IC

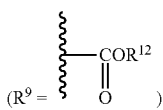

of the invention.

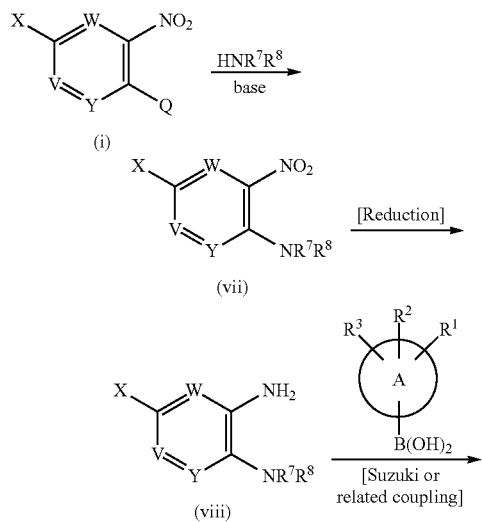

Scheme 1

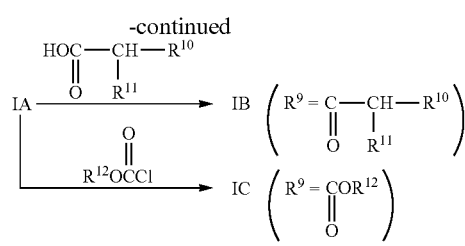

Scheme 2 illustrates a route to compounds of the invention I in which the Suzuki or related coupling is performed on intermediates (vii) to afford intermediates (xi). Reduction under the conditions described above provides anilines of the invention IA which can be coupled with a carboxylic acid or appropriate chloridate to form compounds of the invention IB or IC.

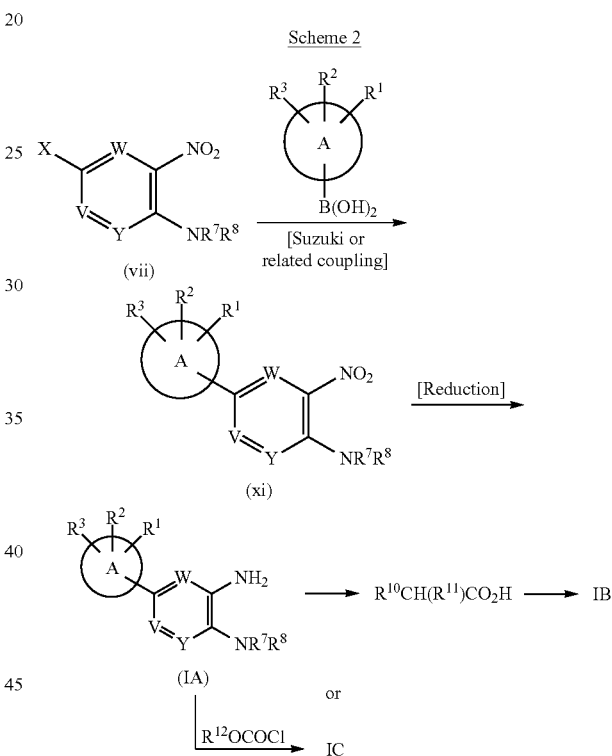

Scheme 2

Scheme 3 illustrates a method suitable for preparation of compounds of the invention for which the boronic acid/ester or related derivatives of the

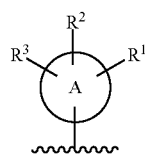

group do not readily undergo coupling reactions or are not commercially available or readily accessible. Derivatives (viii) can be coupled with boronate ester dimers such as bis(neopentylglycolato)diboron by heating in a solvent such as DMSO, dioxane, toluene or DMF in the presence of a base such as potassium acetate and a catalyst such as Cl$_2$Pd(dppf) to give aryl boronate esters (xiii). These esters can undergo Suzuki or related couplings as described above, to afford compound IA of the invention. Functionalization as above by treatment with carboxylic acid

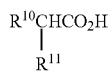

or chloridate R$^{12}$OCOCl affords compounds of the invention IB or IC, respectively.

Scheme 3

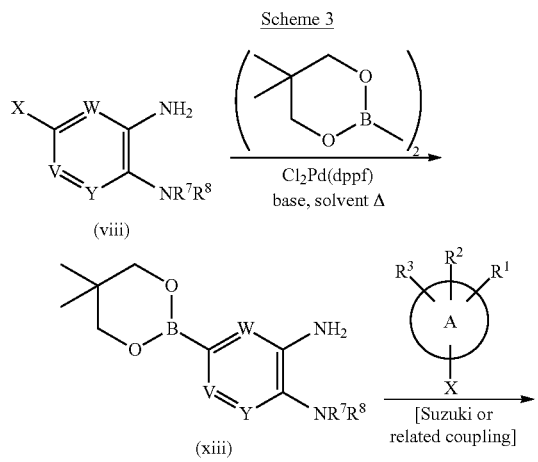

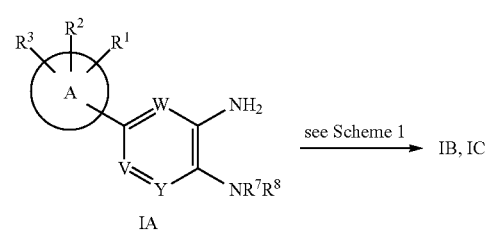

In Scheme 4 the order of synthetic steps is changed from that shown in Scheme 3. Accordingly, aryl boronate esters (xiii) are functionalized by coupling with a carboxylic acid R$^{10}$R$^{11}$CHCO$_2$H or acid chloride R$^{10}$R$^{11}$CHCOCl or chloroformate R$^{12}$OCOCl, to give amides or carbamates (xv) which undergo Suzuki or related couplings as described above to afford compounds of the invention IB or IC. Alternatively, (xv) may be prepared from viii or xxxvi (Scheme 11) by the conditions shown in Scheme 3 on viii. These derivatives undergo Suzuki or related coupling reactions to afford compounds IA, IB or IC of the invention.

Scheme 4

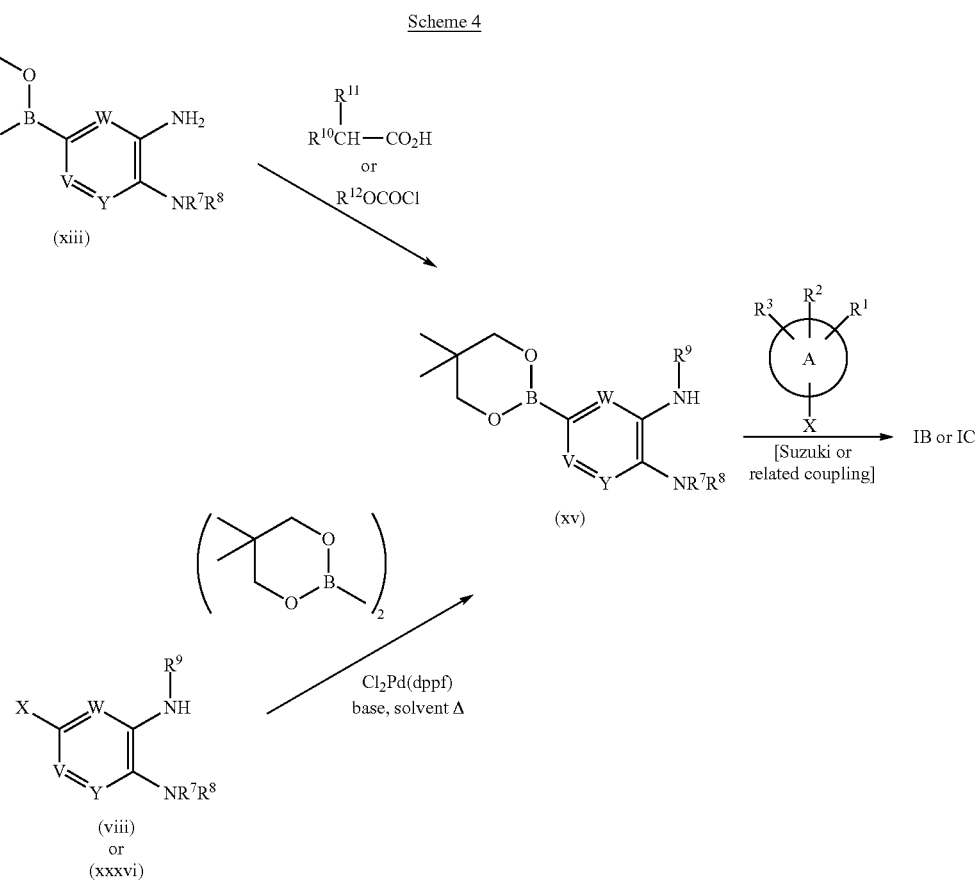

Scheme 5 describes an additional method for the preparation of compounds of the invention I. Compound (xvi) can react with primary or secondary amines HNR⁷R⁸, either in excess or in the presence of a suitable base such as an aliphatic tertiary amine, optionally in the presence of a solvent such as DMF or NMP, at elevated temperature to provide adducts (xvii). Esters (xvii) may be converted to the corresponding carboxylic acids under various conditions familiar to those of ordinary skill in the art. Generally this is effected using an alkali metal hydroxide (MOH) in aqueous solution, preferably with an organic co-solvent such as methanol or THF. Carboxylic acids (xviii) can be converted (by treatment with DPPA and a tertiary amine base) to acyl azides which rearrange (Curtius rearrangement) upon heating to form isocyanates which can be trapped by alcohols R'OH to furnish carbamates (xix). Many variations on the Curtius rearrangement are familiar to those skilled in the art of organic/medicinal chemistry which have utility for the transformation of carboxylic acids such as (xviii) into carbamates (xix) or the related amines (viii). Transformation of carbamates (xix) into the corresponding anilines (viii) is effected in a manner which depends upon the nature of the R' group. Typically, acidic conditions (~4M HCl in dioxane or ~1:1 TFA-CH$_2$Cl$_2$) are used for acid-labile carbamates (R'=t-Bu). Benzylic carbamates are generally cleaved to the corresponding anilines by exposure to hydrogen gas in the presence of a noble metal catalyst such as Pd or Pt or by phase transfer hydrogenolysis. (*Synthesis*, 685 (1976).) Methods for transformation of carbamates (xix) and anilines (viii) into compounds of the invention I are described in the other Schemes.

Scheme 5

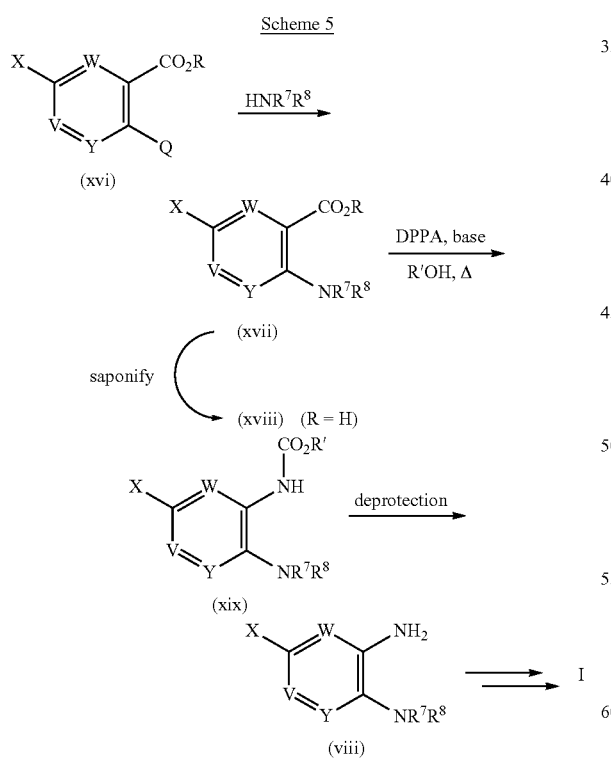

Compounds of the invention IA are useful for preparation of further compounds of the invention as shown in Scheme 6. Treatment of IA with a phenyl chloroformate derivative and a suitable base, generally in a solvent such as dichloromethane provides phenyl carbamate derivatives (IC). Analogs wherein R is a p-nitro group are highly electrophilic and react with phenols under basic conditions to yield further compounds of the invention (IC). Suitable bases include but are not limited to pyridines and aliphatic tertiary amines. These derivatives may be isolated or used in the next reaction without isolation.

Scheme 6

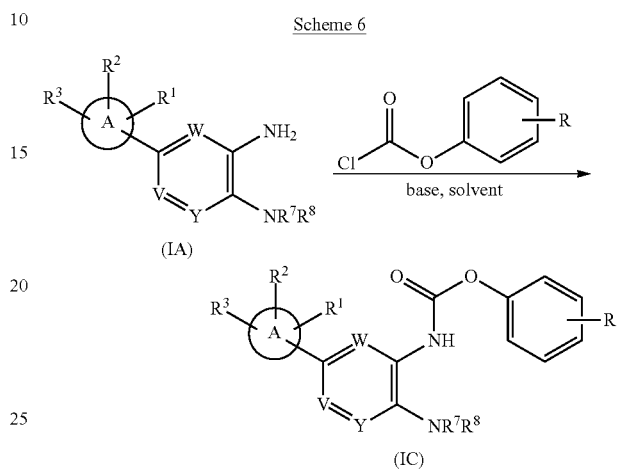

Intermediates prepared in the above Schemes may require further elaboration in order to be converted into compounds of the invention. Examples of this are provided in the following Schemes.

Scheme 7 illustrates the conversion of nitriles (ID) into tetrazoles of the invention (IE). Typically, the nitrile (ID) is prepared by chemistry described above (often Suzuki coupling on an intermediate such as (viii)) and heated with an azide such as tributyltinazide in a solvent such as toluene at or near the boiling point. This methodology could be used to prepare aliphatic or heteroaromatic tetrazole derivatives in addition to the phenyl derivatives shown.

Scheme 7

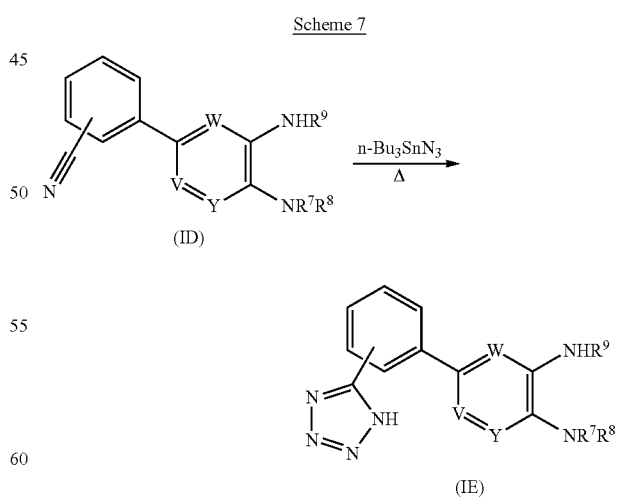

Scheme 8 illustrates the transformation of intermediates or compounds of the invention into further intermediates or compounds of the invention by functional group interconversions. Accordingly, alkyl ethers (xxv) can be converted to phenols by treatment with Lewis acids such as BBr₃, preferably in a solvent such as CH₂Cl₂ or CH₂ClCH₂Cl. Re-alkylation affords new ether derivatives (xxx) in which the carboxylic acid has also been alkylated. Alternatively, phenols may be alkylated using the Mitsunobu reaction. (Reviewed in Kumara Swamy, K. C. et al., "Mitsunobu and Related Reactions: Advances and Applications", *Chem. Rev.*, 109:2551-2651 (2009).) Further transformation affords carboxylic acids derivatives (IF) which, depending upon the group R' may be compounds of the invention I or protected intermediates which could be further transformed into compounds of the invention I. The saponification reaction is generally accomplished by the use of an alkali metal hydroxide in aqueous or mixed aqueous/organic solvents. This methodology could be used to prepare heteroaromatic carboxylate derivatives in addition to the phenyl derivatives shown.

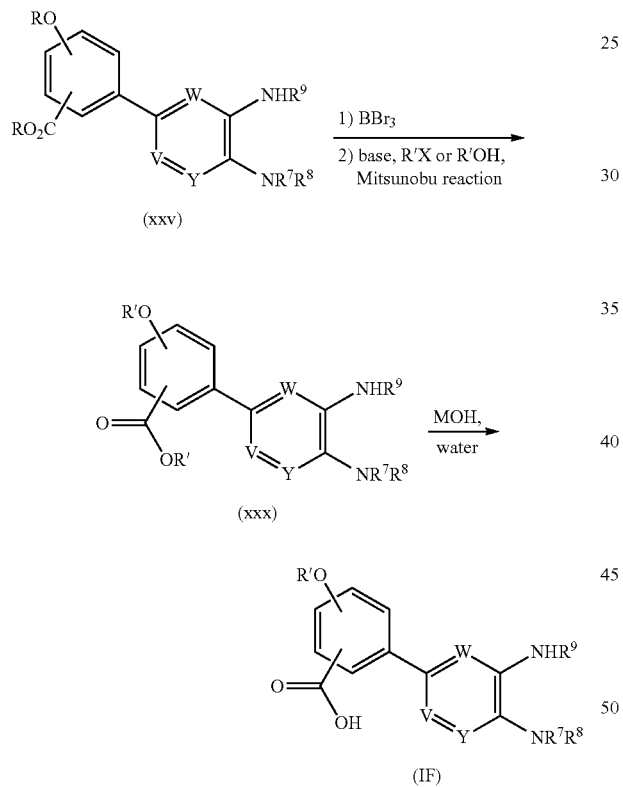

Carboxylic acids (IF) can be derivatized, as shown below in Scheme 9, to provide acylsulfonamides (IC) which, depending upon the group R may be compounds of the invention I or which may be transformed into compounds of the invention I using chemistry described in the schemes above. Generally, the conversion of carboxylic acids to acylsulfonamides is accomplished using a coupling reagent such as CDI and a base such as DBU in a solvent such as DMF or THF. This methodology could be used to prepare heteroaromatic acylsulfonamide derivatives in addition to the phenyl derivatives shown.

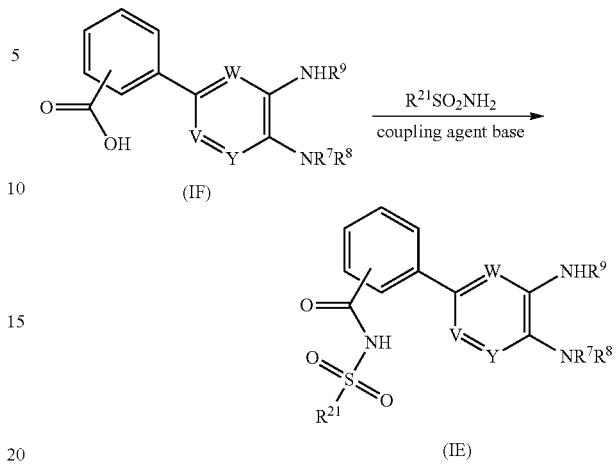

The methods described in the above Schemes can be used to prepare amine derivatives (IJ) which may be further elaborated by treatment with a base and an electrophile such as an acyl or sulfonyl chloride or a carboxylic or sulfonic acid anhydride or activated esters or the like to prepare carboxamide or sulfonamide compounds of the invention I (Scheme 10). Alternatively, this derivatization could be performed on an earlier intermediate which could be transformed into compounds of the invention I using reactions described in the schemes above. This methodology could be used to prepare heteroaromatic amine derivatives in addition to the aniline derivatives shown.

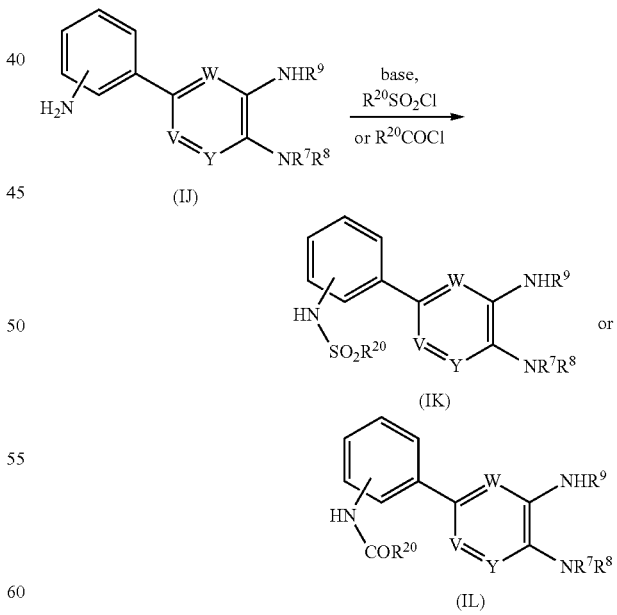

Compounds (viii) (prepared by the methods described above) may be coupled with carboxylic acids using peptide coupling reagents such as Bop, Pybop, HATU or a similar reagent and a suitable base in a solvent such as THF, DMF, NMP, or the like to afford intermediates (xxxvi) (Scheme 11). The use of such peptide coupling reagents has been reviewed by Han, S.-Y. et al., *Tetrahedron*, 60:2447-2467 (2004). Suitable bases include, but are not limited to aliphatic tertiary amines. Alternatively, amines (viii) could react with acid chlorides of the formula R$^{10}$CH$_2$COCl to give amides (xxxvi) as above or under biphasic (Schotten-Bauman) conditions. Conversion of (xxxvi) to compounds of the invention IM is accomplished by coupling under Suzuki or related conditions as described above.

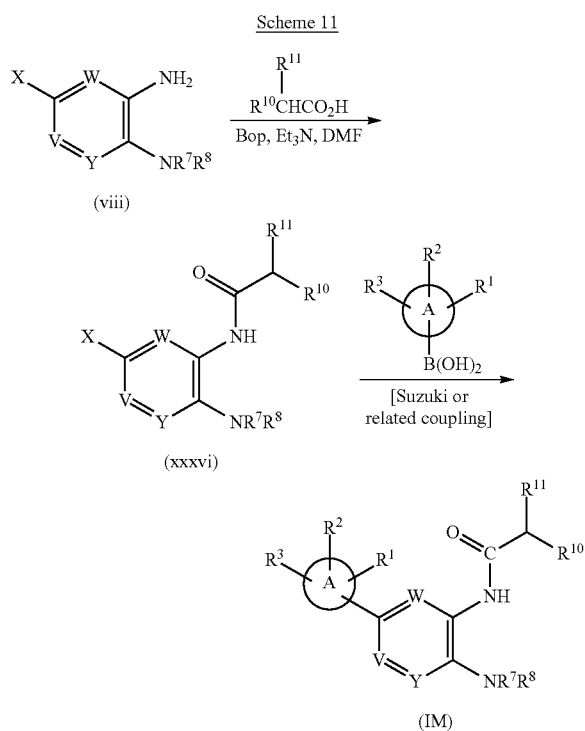

Scheme 11

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

General Experimental

Air- or moisture-sensitive reactions were generally performed under an atmosphere of nitrogen or argon in anhydrous solvents (EMD DRISOLV®). Zinc (~325 mesh) for nitro group reduction was obtained from Alfa Aesar. Reaction concentrations indicated in the tables and procedures are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/F254 were used with visualization by UV light at ~254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous MgSO$_4$ followed by filtration and rinsing the residual solids with an appropriate organic solvent. "Stripped" means concentration under reduced pressure, generally on a rotary evaporator. "Silica gel chromatography", "flash chromatography", or "chromatographed on silica gel" refers to glass column chromatography performed in a manner similar to that described by Still (*J. Org. Chem.*, 43:2923 (1978)). Typically silica gel 60 (EMD, 230-400 mesh ASTM) is used with solvents from JT Baker or Mallinckrodt. HPLC refers to purification by reverse-phase high-performance liquid chromatography generally on C18 columns using the stated mobile phases. Analytical HPLC runs were performed using the columns, flow rates, and mobile phases indicated. It is understood that analytical HPLC retention times (T$_r$) are reported in minutes, and may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Generally, mass spectral results are reported as the (M+H)$^+$ value. For halogenated compounds where two or more peaks are significant, m/z for one peak in the cluster, generally the most intense, is reported. $^1$H NMR spectra were recorded on dilute solutions at 400 or 500 MHz on VARIAN® or JEOL® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Unless otherwise specified, the various substituents of the compounds as employed herein are defined in the same manner as compounds of the invention of Formula (I).

For ease of reference, the following abbreviations may be used herein.

| Abbreviations | |
|---|---|
| AcOH, HOAc | acetic acid |
| ACN | acetonitrile |
| Ac$_2$O | acetic anhydride |
| ADDP | 1,1'-(azodicarbonyl)dipiperidine |
| aq. | aqueous |
| Bn | benzyl |
| Boc | t-butyl carbamate |
| Boc$_2$O | di-t-butyl dicarbonate |
| Bu | butyl |
| Cbz | benzyl carbamate |
| conc. | concentrated |
| DCE | dichloroethane |
| DCM | dichloromethane |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethylsulfoxide |
| DMT-MM | 4-(4,6-dimethoxy-1,3,5-triazin-2-yl)-4-methylmorpholinium chloride |

-continued

| Abbreviations | |
|---|---|
| EDC | 1-(3-(dimethylamino)propyl)-3-ethylcarbodiimide hydrochloride |
| Et | ethyl |
| EtOAc | ethyl acetate |
| EtOH | ethanol |
| $Et_2O$ | diethyl ether |
| $Et_3N$ | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high performance liquid chromatography |
| i-PrOH | isopropanol |
| KOAc | potassium acetate |
| LAH | Lithium aluminum hydride |
| min | minute(s) |
| Me | methyl |
| MeCN | acetonitrile |
| MeOH | methanol |
| $Me_2NH$ | dimethylamine |
| NaHMDS | sodium bis(trimethylsilyl)amide |
| $Na(OAc)_3BH$ | sodium triacetoxyborohydride |
| n-BuLi | n-butyllithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| $Pd(dppf)_2Cl_2$ | [1,1'-bis(diphenylphosphino)ferrocene]dichloropalladium(II) |
| $Pd(OAc)_2$ | palladium acetate |
| $Pd(PPh_3)_4$ | tetrakis(triphenylphosphine)palladium |
| $Pd_2(dba)_3$ | tris(dibenzylideneacetone)dipalladium(0) |
| PE | Petroleum ether |
| Ph | phenyl |
| PhMe | toluene |
| $Ph_2TfN$ | 1,1,1-trifluoro-N-phenyl-N-(trifluoromethyl)sulfonylmethanesulfonamide |
| $PPh_3$ | triphenyl phosphine |
| RB | Round-bottom flask |
| rt | room temperature |
| sat. | saturated |
| t-Bu | tertiary butyl |
| t-BuOH | tertiary butanol |
| TFA | trifluoroacetic acid |
| $Tf_2O$ | trifluoromethylsulfonic anhydride |
| THF | tetrahydrofuran |
| TMS | trimethylsilyl |
| TsO | p-toluenesulfonyl |

Analytical HPLC Conditions:

[a] Waters Sunfire C18 4.6×150 mm 3.5μ. 1 mL/min, 10-90% methanol-water 0.2% $H_3PO_4$, gradient over 15 min.

[b] Waters Sunfire C18 4.6×150 mm 3.5 n. 1 mL/min, 10-90% methanol-water 0.2% $H_3PO_4$, gradient over 10 min.

[c] YMC S5 ODS, 4.6×50 mm. 4 mL/min, 10-90% methanol-water 0.2% $H_3PO_4$, gradient over 12 min.

[d] Waters X-Bridge Phenyl 4.6×150 mm 3.5 n, 1 mL/min, 10-90% methanol-water 0.2% $H_3PO_4$, gradient over 10 min.

[e] YMC S5 ODS, 4.6×50 mm. 4 mL/min, 10-90% methanol-water 0.2% $H_3PO_4$, gradient over 4 min.

[f] YMC S5 ODS, 4.6×50 mm. 1 mL/min, 10-90% methanol-water 0.2% $H_3PO_4$, gradient over 15 min.

[g] Sunfire C18 3.0×150 mm 3.5μ. 0.5 mL/min, 14-95% acetonitrile-water, 0.05% TFA, gradient over 12 min.

[h] YMC pro c18 S5 ODS, 4.6×50 mm. 4 mL/min, 10-90% methanol-water 0.2% $H_3PO_4$, gradient over 12 min.

[i] SUPELCO® Ascentis 4.6×50 mm, 2.7μ C18, 4 mL/min, 5-95% acetonitrile-water, 10 mM $NH_4OAc$, gradient over 4 min. (Column temp.=35° C.)

[j] Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

[k] Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[l] Luna C18, 4.6×30 mm, 3-μm particles; 10-90% MeOH-water (0.1% TFA in both phases) gradient over 5 min. Flow: 4 mL/min.

[m] ZORBAX® SB C18, 4.6×75 mm, 50-90% MeOH-water (0.1% TFA in both phases) gradient over 8 min. Flow: 2.5 mL/min.

[n] YMC S5 ODS, 4.6×50 mm. 4 mL/min, 10-90% methanol-water 0.05% TFA, gradient over 4 min.

[o] Luna C18, 4.6×30 mm, 3-μm particles; 10-86% $CH_3CN$-water (10 mM $NH_4OAc$ in both phases) gradient over 2 min. Flow: 4 mL/min.

[p] Luna C18, 4.6×30 mm, 3-μm particles; 10-90% MeOH-water (0.1% TFA in both phases) gradient over 2 min. Flow: 4 mL/min.

[q] Luna C18, 4.6×30 mm, 3-μm particles; 10-90% MeOH-water (0.1% TFA in both phases) gradient over 3.5 min. Flow: 4 mL/min.

[r] PHENOMENEX®, 2.0×30 mm, 2.5-μm particles; 26-90% MeOH-water (0.1% TFA in both phases) gradient over 3 min. Flow: 1 mL/min.

[s] Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[t] Column: Xbridge (150×4.6 mm), 3.5μ; Method: 0.05% TFA in water pH2.5; Mobile Phase A: Buffer: acetonitrile (95:5) Mobile Phase B: acetonitrile: Buffer (95:5) Flow: 1.0 ml/min.

[u] Column: Sunfire (150×4.6 mm), Method: 0.05% TFA in water pH2.5 Mobile Phase A: Buffer: acetonitrile (95:5) Mobile Phase B: acetonitrile: Buffer (95:5) Flow: 1.0 ml/min.

[v] Column: Ascentis Express C8 (5×2.1 mm) 2.7 μM particles, 10 mM in ammonium formate. 98:2 to 2:98 water-acetonitrile gradient over 1.5 min. Flow: 1.0 ml/min.

The initial synthetic step shown in the schemes preparation of compounds of the present invention is generally addition of an amine to a halobenzene derivative. Many of the amines employed for these transformations are either commercially-available or or known in the literature. Other, novel amines are prepared by the transformations shown herein.

Intermediate Example 1a

N-(4,4,4-trifluorobutyl)cyclohexanamine

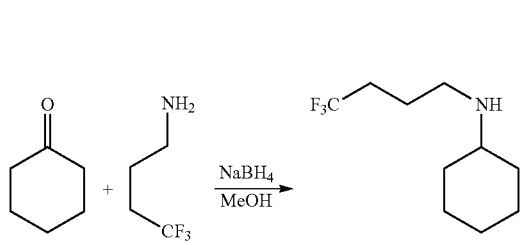

A solution of 4,4,4-trifluorobutan-1-amine (1.802 ml, 15.73 mmol) and cyclohexanone (1.712 ml, 16.52 mmol) in MeOH (31.5 ml) was heated at 40° C. for 1 h, then allowed to cool to rt. sodium borohydride (0.893 g, 23.60 mmol) was added. Caution: exotherm! The reaction was allowed to stir at rt overnight. The solvent was evaporated and the crude material taken up in EtOAc and $H_2O$. Layers were separated. The aqueous phase was extracted with EtOAc (2×). The combined organic phases were dried over $Na_2SO_4$, filtered, and concentrated to afford N-(4,4,4-trifluorobutyl)cyclohexanamine (3.03 g, 13.76 mmol, 87% yield) as a colorless oil. MS(ES): m/z=210 [M+H]$^+$.

Intermediate Example 1b

N-(3-methoxy-3-methylbutyl)cyclohexanamine

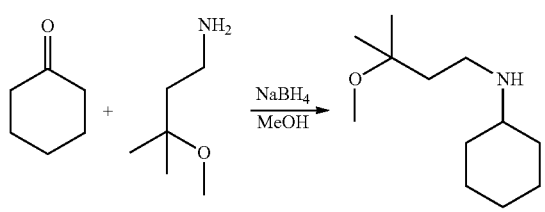

A solution of and 3-methoxy-3-methylbutan-1-amine (0.5 g, 4.27 mmol) in MeOH (2.133 ml) was warmed to 40° C. for 30 min. then cooled to RT. This solution was treated with sodium borohydride (0.242 g, 6.40 mmol) and stirred overnight. The reaction was diluted with water and ext. twice with dichloromethane. The combined organic extracts were dried and solvent was removed under a stream of nitrogen to afford N-(3-methoxy-3-methylbutyl)cyclohexanamine (0.74 g, 3.53 mmol, 83% yield) as a colorless oil. MS(ES): m/z=200 [M+H]$^+$.

Intermediate Example 2a

N-(2-isopropoxyethyl)-2-methylpropan-1-amine

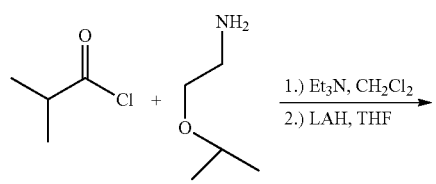

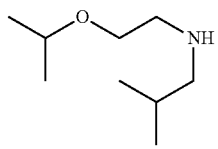

A solution of 2-isopropoxyethanamine (3.38 ml, 27.5 mmol) and triethylamine (3.83 ml, 27.5 mmol) in dichloromethane (25.00 ml) was cooled to 0° C. then treated with isobutyryl chloride (2.62 ml, 25 mmol) over 1-2 min. The resulting slurry was warmed to RT then washed with aq. HOAc then aq. sodium bicarbonate, dried, and stripped to afford N-(2-isopropoxyethyl)isobutyramide as a colorless oil. Spectra consistent with the proposed amide at a purity of >95%. LCMS: 174 ((M+H)$^+$). A solution of N-(2-isopropoxyethyl)isobutyramide (3.98 g, 23 mmol) in 5 mL of THF was treated with a 1M solution of LAH (25 mL, 25 mmol) in THF over 2-3 min. The resulting solution was stirred at reflux for 6 h then ON at RT, then stirred 6 h longer at reflux. The reaction was quenched by the method of Fieser, filtered, and stripped to afford N-(2-isopropoxyethyl)-2-methylpropan-1-amine (3.2 g, 19.09 mmol, 83% yield) as a colorless oil. LCMS: 160 ((M+H)$^+$).

Intermediate Example 2b

N-isobutylpentan-3-amine

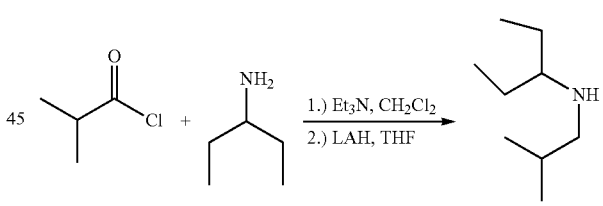

A stirred, cooled (0° C.) solution of pentan-3-amine (2.80 mL, 24.00 mmol) and triethylamine (3.35 mL, 24.00 mmol) in dichloromethane (20 mL) was treated with isobutyryl chloride (2.112 mL, 20 mmol) over 5 min. The resulting mixture was brought to RT and stirred for 1 h. The reaction was diluted with 1:1 ether-hexanes and washed with 1M aq. HCl then sat. aq. sodium bicarbonate. The org. phase was dried and stripped to afford N-(pentan-3-yl)isobutyramide (3.1 g, 18.73 mmol, 94% yield) as a colorless solid. LCMS: 158 (M+H)$^+$. A 1M solution of LAH (20.00 ml, 20 mmol) in THF was added to N-(pentan-3-yl)isobutyramide (1.94 g, 12.34 mmol). The resulting solution was brought to reflux and stirred ON. The reaction was cooled to RT and given a Fieser quench. The resulting slurry was filtered and stripped to afford N-isobutylpentan-3-amine (1.5 g, 9.95 mmol, 81% yield) as a colorless oil. LCMS: 144 (M+H)$^+$.

Example 1

4'-(Diisobutylamino)-5-fluoro-3'-(2-p-tolylacet-amido)biphenyl-2-carboxylic acid

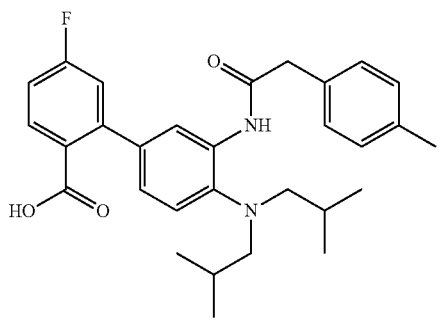 [SMILES: Cc1ccc(CC(=O)Nc2cc(-c3cc(F)ccc3C(=O)O)ccc2N(CC(C)C)CC(C)C)cc1]

1A. 4-Bromo-N,N-diisobutyl-2-nitroaniline

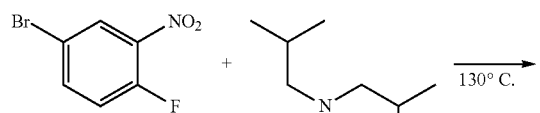

A solution of diisobutylamine (0.284 g, 2.200 mmol) and 4-bromo-1-fluoro-2-nitrobenzene (0.220 g, 1 mmol) was heated at 130° C. for 6 h. The reaction was cooled and diluted with ethyl acetate. This solution was washed with aq. HCl then brine, dried, and stripped to afford 0.3 g (87%) of 4-bromo-N,N-diisobutyl-2-nitroaniline (1A) as an orange oil. $^1$H NMR (400 MHz, DMSO-d$_6$) δ ppm 7.90(d, 1 H, J=2.6 Hz); 7.60(dd, 1 H, J=9.0, 2.4 Hz); 7.32(d, 1 H, J=9.0 Hz); 2.89(d, 4H, J=7.3 Hz); 1.76-1.86(m, 2H); 0.77(d, 12H, J=6.4 Hz). MS(ES): m/z=331 [M+H]$^+$.

1B. 4-Bromo-N1,N1-diisobutylbenzene-1,2-diamine

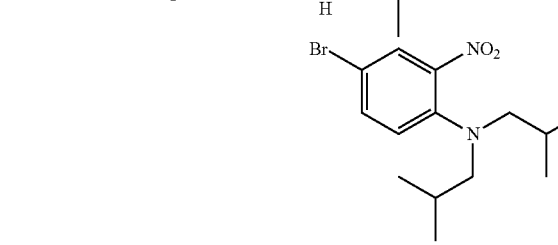

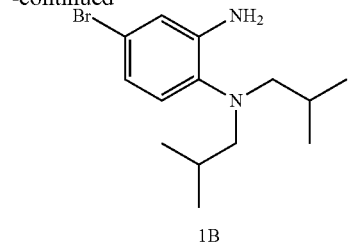

To a stirred solution of 4-bromo-N,N-diisobutyl-2-nitroaniline (1A) (0.9 g, 2.7 mmol) in ethanol (Volume: 10 mL) was added 2 mL of water followed by ammonium chloride (1.46 g, 27.3 mmol) then zinc (1.79 g, 27.3 mmol). The mixture was stirred 1 h, cooling to RT then diluted with dichloromethane and filtered. The filtrate was washed with water, dried, and stripped to afford an oil. Chromatography on silica gel (gradient elution with ether-hexanes) afforded, after removal of solvent, 0.66 g (77%) of 4-bromo-N1,N1-diisobutylbenzene-1,2-diamine (1B) as a pale purple oil. MS(ES): m/z=301 [M+H]$^+$. $^1$H NMR (400 MHz, DMSO-d$_6$) δ ppm 6.92(d, 1 H, J=8.4 Hz); 6.81(d, 1 H, J=2.2 Hz); 6.63(dd, 1 H, J=8.1, 2.2 Hz); 2.53(d, 4H, J=7.0 Hz); 1.59-1.69(m, 2H); 0.84(d, 12H, J=6.6 Hz).

1C. N-(5-Bromo-2-(diisobutylamino)phenyl)-2-p-tolylacetamide

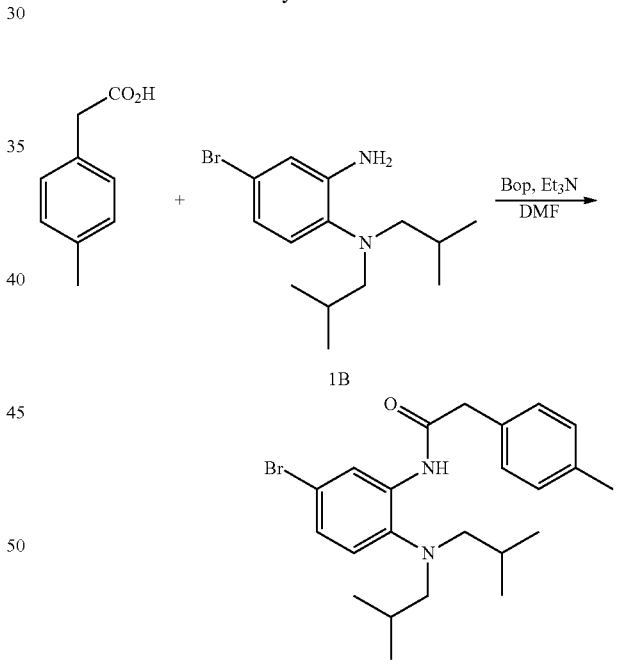

To a solution of 4-bromo-N1,N1-diisobutylbenzene-1,2-diamine (1B) (0.1 g, 0.334 mmol) in DMF (Volume: 1 mL) was added 2-p-tolylacetic acid (0.060 g, 0.401 mmol). The solution was treated with triethylamine (0.093 mL, 0.668 mmol) then BOP (0.177 g, 0.401 mmol) and stirred 16 h at RT. The solution was diluted with ether and washed with aq. HOAc then twice with aq. sodium bicarbonate. The organic phase was dried and stripped to afford N-(5-bromo-2-(diisobutylamino)phenyl)-2-p-tolylacetamide (18A) (0.15 g, 99% yield) as a pale amber oil. $^1$H NMR (400 MHz, DMSO-$d_6$) δ ppm 8.63(s, 1H), 8.38 (d, 1H, J=2.0 Hz); 7.12-7.23(m, 6H); 3.69(s, 2H); 2.27(s, 3H); 1.46-1.56(m, 2H), 0.73(d, 12H, J=6.6 Hz) (one signal at ~2.5 poorly resolved from solvent). MS(ES): m/z=433 [M+H]$^+$.

1. 4'-(Diisobutylamino)-5-fluoro-3'-(2-p-tolylacetamido)biphenyl-2-carboxylic acid

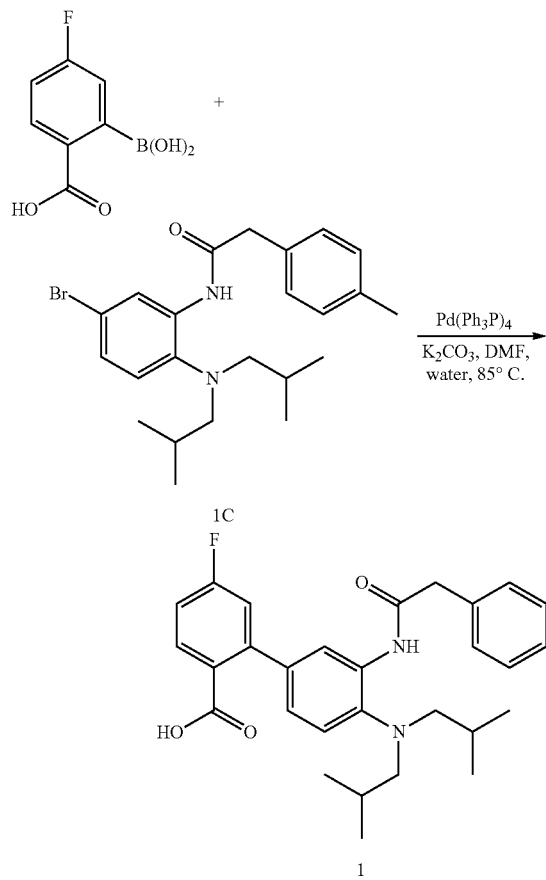

A mixture of 2-borono-4-fluorobenzoic acid (0.026 g, 0.139 mmol) and N-(5-bromo-2-(diisobutylamino)phenyl)-2-p-tolylacetamide (1C) (0.03 g, 0.070 mmol) and tetrakis(triphenylphosphine)palladium(0) (8.04 mg, 6.95 µmol) in degassed DMF (Volume: 1 mL) was treated with aq. potassium carbonate (0.232 mL, 0.348 mmol). The mixture was placed under nitrogen and stirred at 85° C. for 1 h. The reaction was cooled, brought to pH3 with HOAc, filtered, and purified by prep. HPLC (Waters XBridge C18, 19×250 mm, acetonitrile-water gradient, 10 mM in NH$_4$OAc). Concentration of the appropriate fractions by centrifugal evaporation afforded 4'-(diisobutylamino)-5-fluoro-3'-(2-p-tolylacetamido)biphenyl-2-carboxylic acid (0.017 g, 50% yield). $^1$H NMR (400 MHz, DMSO-$d_6$) δ ppm 8.71(s, 1H), 8.26(d, 1H, J=2.0 Hz); 7.74(br. t, 1H, J=6.9 Hz); 7.30(d, 1H, J=8.4 Hz); 7.26(td, 1H, J=8.4, 2.5 Hz); 7.22(d, 2H, J=7.9 Hz); 7.14-7.19(m, 3H); 7.02(dd, 1H, J=7.9, 2.0 Hz); 3.69(s, 2H); 2.56(d, 4H, J=7.4 Hz); 2.29(s, 3H); 1.54-1.64(m, 2H), 0.79(d, 12H, J=6.4 Hz). MS(ES): m/z=491 [M+H]$^+$.

Example 2

N-(4-(Diisobutylamino)-2'-(1H-tetrazol-5-yl)biphenyl-3-yl)-2-p-tolylacetamide

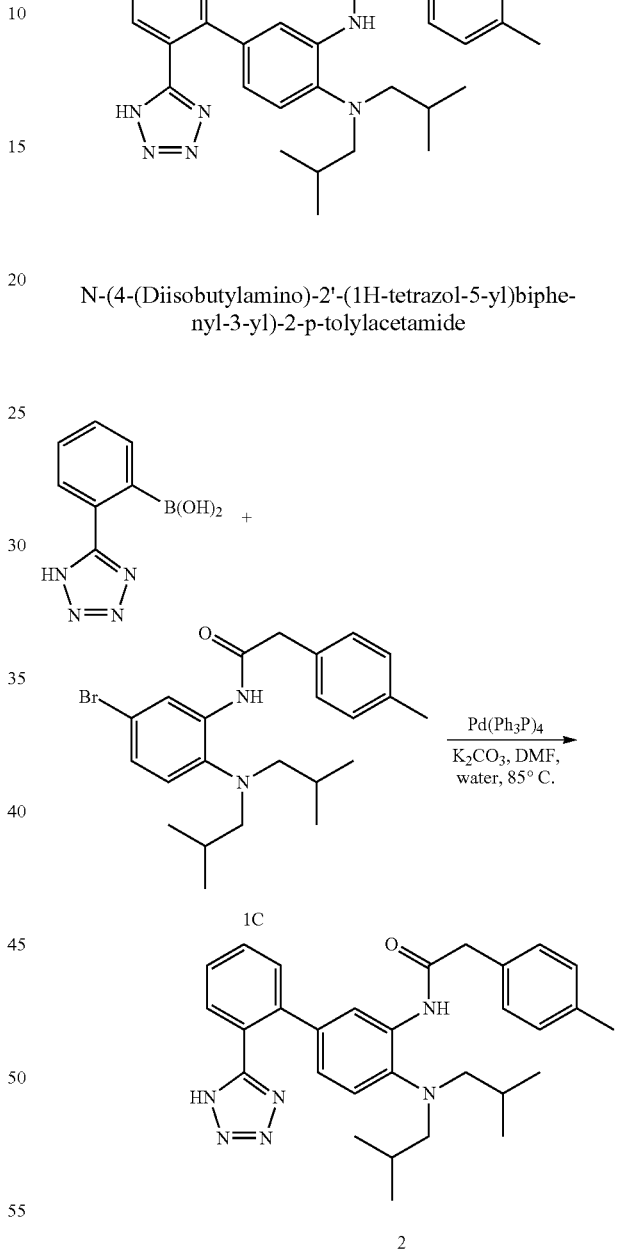

N-(4-(Diisobutylamino)-2'-(1H-tetrazol-5-yl)biphenyl-3-yl)-2-p-tolylacetamide

The title compound was prepared from 1C and 2-tetrazolylphenylboronic acid as follows. To a suspension of 2-(1H-tetrazol-5-yl)benzoic acid (0.026 g, 0.14 mmol) and compound 1C (0.03 g, 0.07 mmol) and tetrakis(triphenylphosphine)palladium(0) (0.008 g, 0.007 mmol) in degassed DMF (Volume: 1 mL) was added aq. potassium carbonate (0.23 mL, 0.35 mmol). The mixture was placed under nitrogen and heated at 85° C. for 2 h. The reaction was cooled, diluted with aq. HOAc, and purified by prep. HPLC (Column: Waters XBridge C18, 19×250 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 25-100% B over 25 minutes, then a 5-minute hold at 100% B; Flow: 20 mL/min. Fractions containing the desired product were combined and dried via centrifugal evaporation.). MS(ES): m/z=497 [M+H]$^+$. HPLC T$_r$: 3.27$^q$.

Example 3

N,N-(4-(Benzyl(isobutyl)amino)-2'-(1H-tetrazol-5-yl)biphenyl-3-yl)-2-(2-(trifluoromethyl)phenyl)acetamide

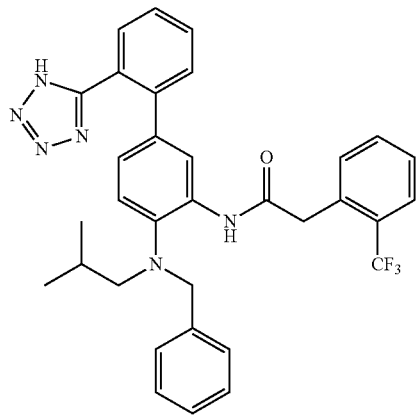 [SMILES: CC(C)CN(Cc1ccccc1)c1ccc(-c2ccccc2-c2nnn[nH]2)cc1NC(=O)Cc1ccccc1C(F)(F)F]

3A. N-Benzyl-4-bromo-N-isobutyl-2-nitroaniline

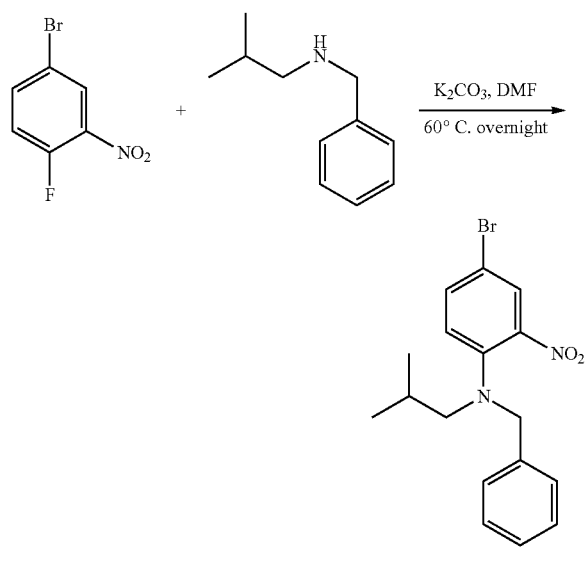 [SMILES: O=[N+]([O-])c1cc(Br)ccc1F ; CC(C)CNCc1ccccc1 ; CC(C)CN(Cc1ccccc1)c1ccc(Br)cc1[N+](=O)[O-]]

To a stirred solution of N-benzyl-2-methylpropan-1-amine (3.0 g, 13.64 mmol) in dry DMF (60 ml) was added K$_2$CO$_3$ (1.88 g, 13.64 mmol) and N-benzyl-2-methylpropan-1-amine (2.67 g, 16.36 mmol) at room temperature. The reaction mixture was heated at 60° C. for overnight. The reaction mixture was cooled to room temperature, diluted with EtOAc, washed with water (3×). The organic layer was dried over Na$_2$SO$_4$, filtered and concentrated in vacuo to give a crude semi solid. Purification using flash column chromatography (0% to 15% ethyl acetate/hexane gradient) provided N-benzyl-4-bromo-N-isobutyl-2-nitroaniline (4.47 g, 90% yield) as semi solid. $^1$H NMR (400 MHz, CDCl$_3$) δ ppm 7.86 (d, 1H, J=2.4 Hz), 7.45 (dd, 1H, J=8.8, 2.4 Hz), 7.29-7.31 (m, 2H), 7.19-7.26 (m, 3H), 7.00 (d, 1H, J=8.8 Hz), 4.25 (s, 2H), 2.82 (d, 2H, J=7.2 Hz), 1.82-1.89 (m, 1H), 0.82 (d, 6H, J=6.8 Hz). MS(ES): m/z=365. [M+H]$^+$.

3B. N1-Benzyl-4-bromo-N1-isobutylbenzene-1,2-diamine

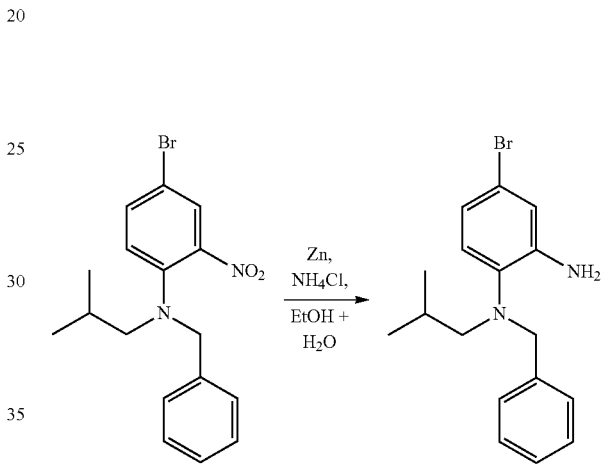

The title compound was prepared from N-benzyl-4-bromo-N-isobutyl-2-nitroaniline by the general procedure used for the conversion of 1A to 1B. $^1$H NMR (400 MHz, DMSO-d$_6$) δ ppm 7.22-7.31 (m, 5H), 6.85(d, 1H, J=2.4 Hz), 6.82 (d, 1H, J=8.4 Hz), 6.60 (dd, 1H, J=8.4, 2.4 Hz), 5.13 (s, 2H), 3.91 (s, 2H), 2.58 (d, 2H, J=6.8 Hz), 1.61-1.68 (m, 1H), 0.81 (d, 6H, J=6.8 Hz). MS(ES): m/z=335.2 [M+H]$^+$.

3C. N1-Benzyl-4-(5,5-dimethyl-1,3,2-dioxaborinan-2-yl)-N1-isobutylbenzene-1,2-diamine

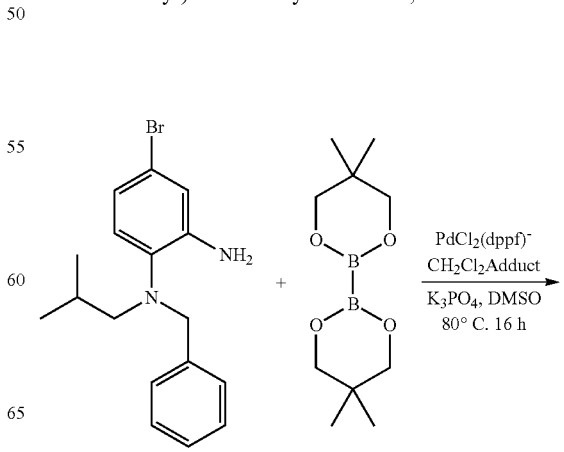

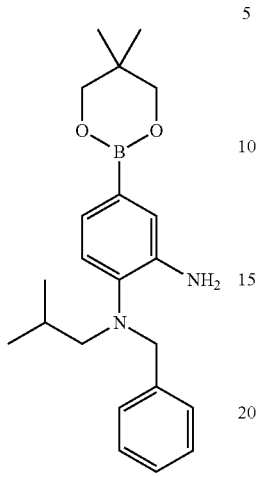

The title compound was prepared from N,N1-benzyl-4-bromo-N1-isobutylbenzene-1,2-diamine by the general procedure used for the conversion of 1B to 49A. $^1$H NMR (400 MHz, CDCl$_3$) δ ppm 7.26-7.29 (m, 1H), 7.19-7.25 (m, 5H), 7.14 (dd, 1H, J=8.0, 1.6 Hz), 6.92 (d, 1H, J=7.6 Hz), 4.03 (brs, 2H), 3.99 (s, 2H), 3.74 (s, 4H), 2.69 (d, 2H, J=7.2 Hz), 1.69-1.75 (m, 1H), 1.01 (s, 6H), 0.82 (d, 6H, J=6.8 Hz). MS(ES): m/z=299. (This mass corresponds to [M+H]$^+$ of free boronic acid. No significant [M+H]$^+$ is seen for the parent compound.)

3D. N4-Benzyl-N4-isobutyl-2'-(2-trityl-2H-tetrazol-5-yl)biphenyl-3,4-diamine

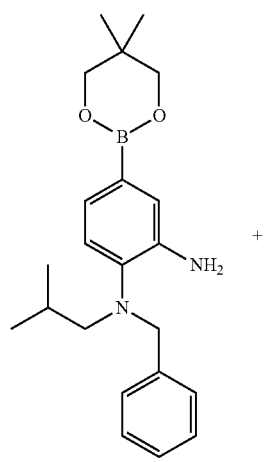

+

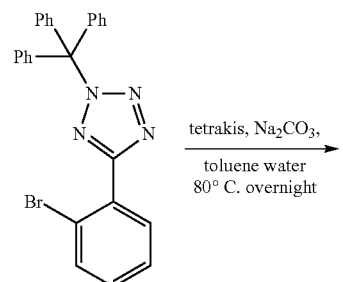

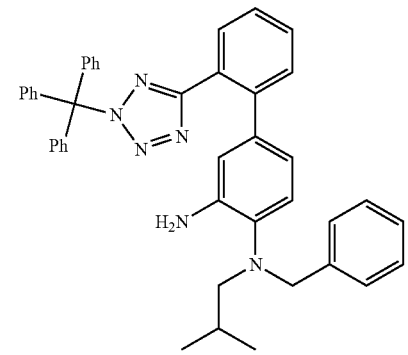

To a stirred solution of N1-benzyl-4-(5,5-dimethyl-1,3,2-dioxaborinan-2-yl)-N1-isobutylbenzene-1,2-diamine (1.42 g, 3.89 mmol), 5-(2-bromophenyl)-2-trityl-2H-tetrazole (1.30 g, 2.78 mmol) in toluene/water mixture was added sodium carbonate (590 mg, 5.56 mmol). The reaction mixture was degassed for 30 minutes, added Pd(Ph$_3$P)$_4$ (193 mg, 0.167 mmol) and again degassed for 5 minutes. The reaction mixture was heated at 80° C. for overnight. The reaction mixture was concentrated in vacuo; the resulting residue was dissolved in ethyl acetate and washed with water, dried over Na$_2$SO$_4$, and concentrated to give crude residue. Purification using flash chromatography in neutral alumina column (0% to 10%, EtOAc/hexanes gradient) provided N4-benzyl-N4-isobutyl-2'-(2-trityl-2H-tetrazol-5-yl)biphenyl-3,4-diamine (750 mg). $^1$H NMR (400 MHz CDCl$_3$) δ ppm 7.85 (dd, 1H, J=8.4, 1.6 Hz), 7.40-7.45 (m, 3H), 7.27-7.39 (m, 8H), 7.18-7.25 (m, 6H), 6.92-6.95 (m, 6H), 6.68 (d, 1H, J=8.0 Hz), 6.58 (d, 1H, J=2.0 Hz), 6.39 (dd, 1H, J=8.4, 2.4 Hz), 3.73 (s, 2H), 2.53 (d, 2H, J=7.2 Hz), 1.54-1.64 (m, 1H), 0.76 (d, 6H, J=6.4 Hz). MS(ES): m/z=641.4 [M+H]$^+$.

3E. N,N-(4-(Benzyl(isobutyl)amino)-2'-(2-trityl-2H-tetrazol-5-yl)biphenyl-3-yl)-2-(2-(trifluoromethyl)phenyl)acetamide

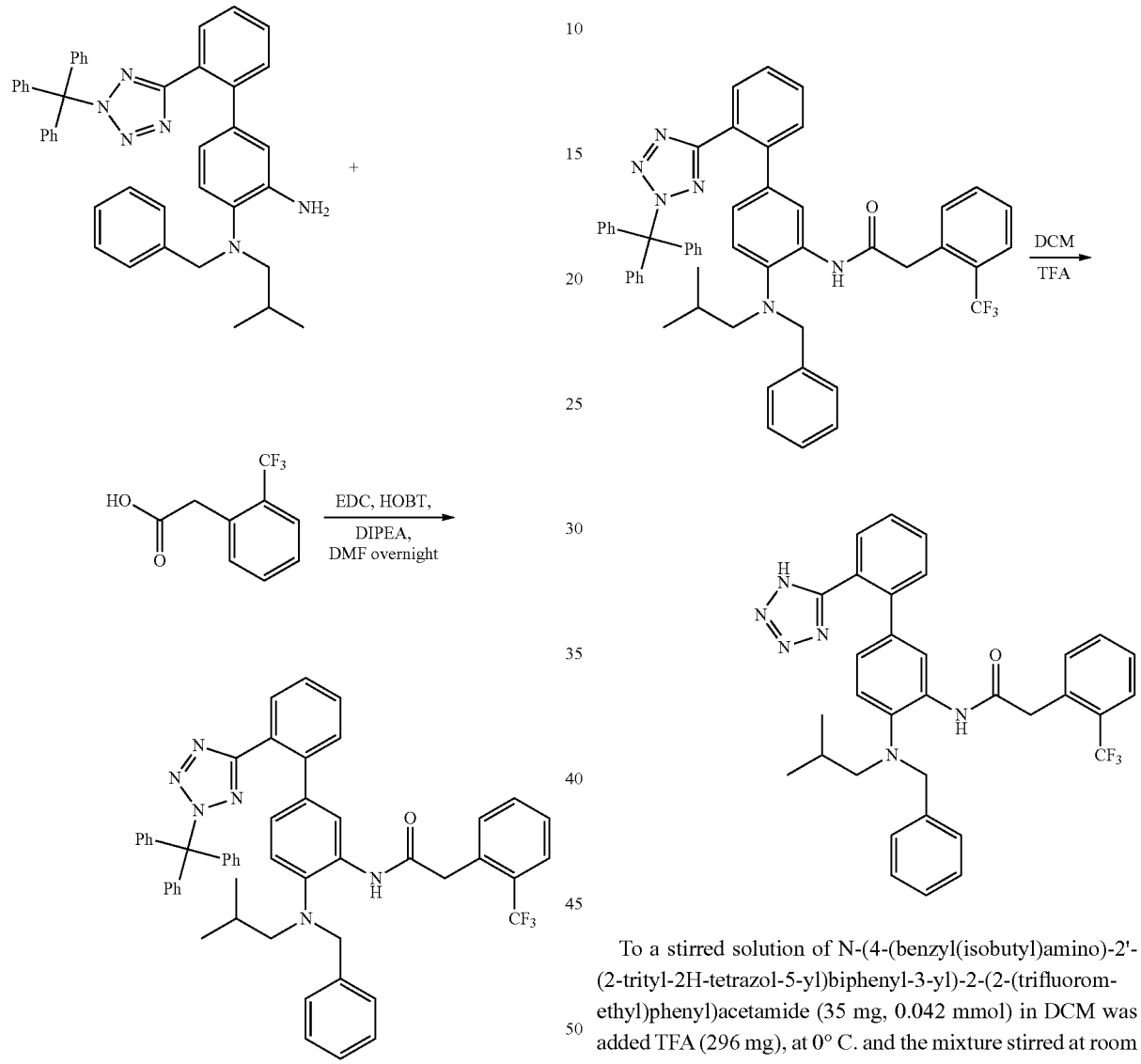

3. N,N-(4-(Benzyl(isobutyl)amino)-2'-(1H-tetrazol-5-yl)biphenyl-3-yl)-2-(2-(trifluoromethyl)phenyl)acetamide To a stirred solution of N4,N4-benzyl-N4-isobutyl-2'-(2-trityl-2H-tetrazol-5-yl)biphenyl-3,4-diamine (0.030 g, 0.047 mmol), 2-(2-(trifluoromethyl)phenyl acetic acid (0.011 g, 0.056 mmol), in DMF was added EDC (0.027 g, 0.140 mmol), HOBT (0.022 g, 0.140 mmol), DIEA (0.049 mL, 0.281 mmol) and the reaction mixture was stirred for 2 h. The reaction mixture was diluted with ethyl acetate and washed with water, dried over Na$_2$SO$_4$, concentrated to give crude residue. Purification using flash column chromatography (0% to 5% ethyl acetate/hexane gradient) provided N,N-(4-(benzyl(isobutyl)amino)-2'-(2-trityl-2H-tetrazol-5-yl)biphenyl-3-yl)-2-(2-(trifluoromethyl)phenyl)acetamide (35 mg, 90%). MS(ES): m/z=826.9 [M+H]$^+$. HPLC T$_r$: 2.81$^v$.

To a stirred solution of N-(4-(benzyl(isobutyl)amino)-2'-(2-trityl-2H-tetrazol-5-yl)biphenyl-3-yl)-2-(2-(trifluoromethyl)phenyl)acetamide (35 mg, 0.042 mmol) in DCM was added TFA (296 mg), at 0° C. and the mixture stirred at room temperature for 1 h. The reaction mixture was diluted with ethyl acetate, washed with 10% NaHCO$_3$ and water, dried over Na$_2$SO$_4$, concentrated to give crude residue. Purification using prep. HPLC provided N,N-(4-(benzyl(isobutyl)amino)-2'-(1H-tetrazol-5-yl)biphenyl-3-yl)-2-(2-(trifluoromethyl)phenyl)acetamide (12 mg, 48.4%). MS(ES): m/z=585.2 [M+H]$^+$, HPLC T$_r$: 2.10$^v$.

Examples 4 to 10

Using the methods described herein, the following compounds of the invention (Table 1) were prepared from carboxamide intermediates (xxxvi) and the appropriate arylboronic acids.

TABLE 1

| Name | A (R1/R2/R3) | R10 | NR7R8 | HPLC Tr | (M + H)+ |
|---|---|---|---|---|---|
| 4'-(diisobutylamino)-3'-(2-p-tolylacetamido)biphenyl-2-carboxylic acid | 2-CO2H-phenyl | 4-methylphenyl | N(iBu)(iBu) | 2.67[k] | 473 |
| 4'-(cyclohexyl(isobutyl)amino)-3'-(2-(2-fluorophenyl)acetamido)biphenyl-2-carboxylic acid | 2-CO2H-phenyl | 2-fluorophenyl | N(iBu)(Cy) | 2.57[k] | 503 |
| 4'-(cyclohexyl(isobutyl)amino)-5-fluoro-3'-(2-(2-fluorophenyl)acetamido)biphenyl-2-carboxylic acid | 4-fluoro-2-CO2H-phenyl | 2-fluorophenyl | N(iBu)(Cy) | 2.69[k] | 521 |
| N-(4-(cyclohexyl(isobutyl)amino)-2'-(1H-tetrazol-5-yl)biphenyl-3-yl)-2-(2-(trifluoromethyl)phenyl)acetamide | 2-(1H-tetrazol-5-yl)phenyl | 2-(trifluoromethyl)phenyl | N(iBu)(Cy) | 2.72[k] | 577 |
| 4'-(cyclohexyl(isobutyl)amino)-3'-(2-(2-(trifluoromethyl)phenyl)acetamido)biphenyl-2-carboxylic acid | 2-CO2H-phenyl | 2-(trifluoromethyl)phenyl | N(iBu)(Cy) | 2.72[k] | 553 |
| N-(4-(cyclohexyl(isobutyl)amino)-2'-(1H-tetrazol-5-yl)biphenyl-3-yl)-2-(2-fluorophenyl)acetamide | 2-(1H-tetrazol-5-yl)phenyl | 2-fluorophenyl | N(iBu)(Cy) | 2.63[k] | 527 |

TABLE 1-continued

| Name | 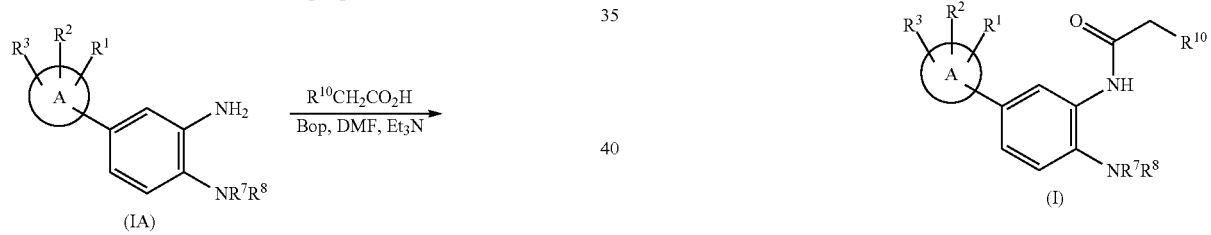 | $R^{10}$ | $NR^7R^8$ | HPLC $T_r$ | $(M + H)^+$ |
|---|---|---|---|---|---|
| N-(4-(butyl(cyclohexyl)amino)-2'-(1H-tetrazol-5-yl)-[1,1'-biphenyl]-3-yl)-2-(2-fluorophenyl)acetamide | | | | $2.54^q$ | 527 |

Examples 11 to 20

Using the methods described herein (the procedure of Example 3 is representative) the following compounds shown below in Table 2 were prepared from 1B.

TABLE 2

| Name | | $R^{10}$ | $NR^7R^8$ | HPLC $T_r$ | $(M + H)^+$ |
|---|---|---|---|---|---|
| N-(4-(diisobutylamino)-2'-(1H-tetrazol-5-yl)biphenyl-3-yl)-2-(4-methoxyphenyl)acetamide | | | | $2.53^k$ | 513 |

TABLE 2-continued

| Name | A | R<sup>10</sup> | NR<sup>7</sup>R<sup>8</sup> | HPLC T<sub>r</sub> | (M + H)<sup>+</sup> |
|---|---|---|---|---|---|
| N-(4-(diisobutylamino)-2'-(1H-tetrazol-5-yl)biphenyl-3-yl)-2-(4-fluorophenyl)acetamide | 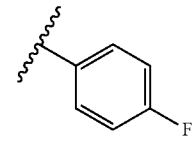 [SMILES: *c1ccc(F)cc1] | 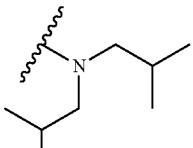 | 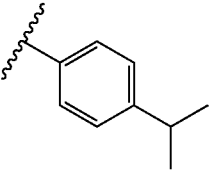 [SMILES: *c1ccc(C(C)C)cc1] | 2.57$^k$ | 501 |
| N-(4-(diisobutylamino)-2'-(1H-tetrazol-5-yl)biphenyl-3-yl)-2-(4-isopropylphenyl)acetamide | | 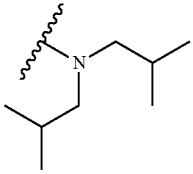 [SMILES: *N(CC(C)C)CC(C)C] | | 2.88$^k$ | 525 |
| 2-(benzo[d][1,3]dioxol-5-yl)-N-(4-(diisobutylamino)-2'-(1H-tetrazol-5-yl)biphenyl-3-yl)acetamide | | 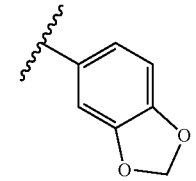 [SMILES: *c1ccc2c(c1)OCO2] | 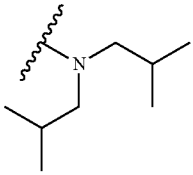 | 2.48$^k$ | 527 |
| N-(4-(diisobutylamino)-2'-(1H-tetrazol-5-yl)biphenyl-3-yl)-2-(4-(trifluoromethoxy)phenyl)acetamide | 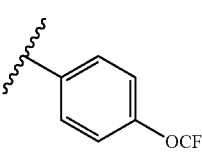 | 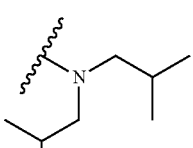 | | 2.67$^k$ | 567 |
| N-(4-(diisobutylamino)-2'-(1H-tetrazol-5-yl)biphenyl-3-yl)-2-(3-fluorophenyl)acetamide | | 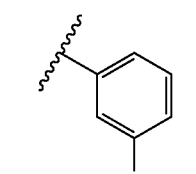 | 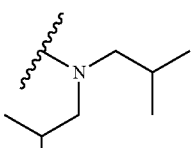 | 2.61$^k$ | 501 |
| 2-(4-chlorophenyl)-N-(4-(diisobutylamino)-2'-(1H-tetrazol-5-yl)biphenyl-3-yl)acetamide | 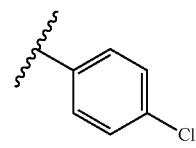 [SMILES: *c1ccc(Cl)cc1] | 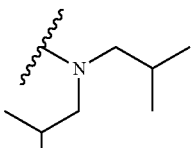 | | 2.73$^k$ | 517 |

TABLE 2-continued

| Name | R¹⁰ | NR⁷R⁸ | HPLC T$_r$ | (M + H)⁺ |
|---|---|---|---|---|
| N-(4-(diisobutylamino)-2'-(1H-tetrazol-5-yl)biphenyl-3-yl)-2-(4-methoxy-2-(trifluoromethyl)phenyl)acetamide | | | 2.76$^k$ | 581 |
| N-(4-(diisobutylamino)-2'-(1H-tetrazol-5-yl)biphenyl-3-yl)-2-(2-fluorophenyl)acetamide | | | 2.64$^k$ | 501 |
| N-(4-(diisobutylamino)-2'-(1H-tetrazol-5-yl)biphenyl-3-yl)-2-(2-fluoro-4-methylphenyl)acetamide | | | 2.76$^k$ | 515 |

Example 21

N-(4-(cis-3,5-Dimethylpiperidin-1-yl)-2'-(1H-tetrazol-5-yl)-[1,1'-biphenyl]-3-yl)-2-(p-tolyl)acetamide

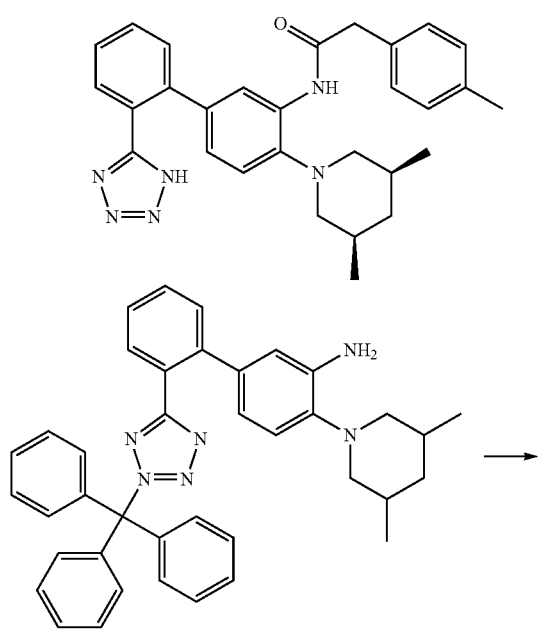

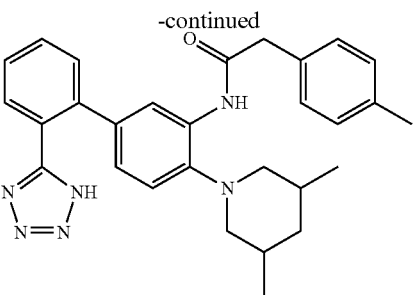

To a solution of 4-(cis-3,5-dimethylpiperidin-1-yl)-2'-(2-trityl-2H-tetrazol-5-yl)-[1,1'-biphenyl]-3-amine (prepared in a manner similar to Example 33D) (59 mg, 0.100 mmol) in DMF (1 mL) was added 2-(p-tolyl)acetic acid (15.00 mg, 0.100 mmol). The solution was treated with TEA (0.028 mL, 0.200 mmol) then BOP (53.0 mg, 0.120 mmol) and stirred 16 h at room temperature. 4M HCl in dioxane (0.150 mL, 0.598 mmol) was added to the reaction mixture. The reaction mixture was heated at 50° C. for 10 min. The reaction was concentrated and purified by HPLC Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 20-100% B over 25 minutes, then a 5-minute hold at 100% B; Flow: 20 mL/min. Fractions containing the desired product were combined and dried via centrifugal evaporation to obtain N-(4-(cis-3,5-dimethylpiperidin-1-yl)-2'-(1H-tetrazol-5-yl)-[1,1'-biphenyl]-3-yl)-2-(p-tolyl)acetamide (32.5 mg, 68% yield). LC/MS. LC/MS, m/z 481.5 (M+H)+. HPLC Rt=1.94$^j$.

Example 22

N-(4-(cis-3,5-Dimethylpiperidin-1-yl)-2'-(1H-tetrazol-5-yl)-[1,1'-biphenyl]-3-yl)-2-(4-fluorophenyl)acetamide

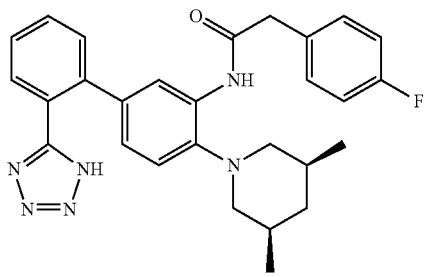 [SMILES: C[C@@H]1C[C@H](C)CN(c2ccc(-c3ccccc3-c3nnn[nH]3)cc2NC(=O)Cc2ccc(F)cc2)C1]

The title compound was prepared from p-fluorophenylacetic acid employing the procedure as described in Example 21. LC/MS. LC/MS, m/z 485.4 (M+H)+. HPLC Rt=1.83$^j$.

Examples 23 to 44

Following the procedure set out below, the following compounds were prepared.

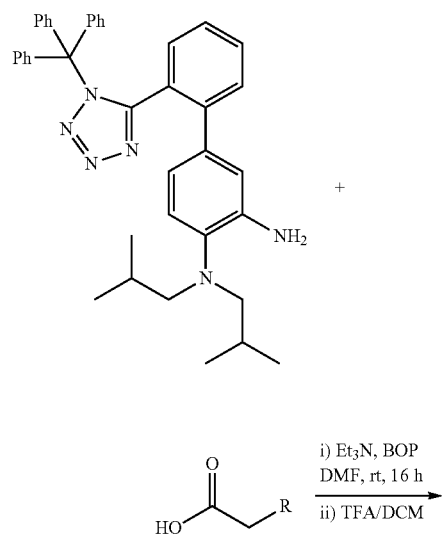

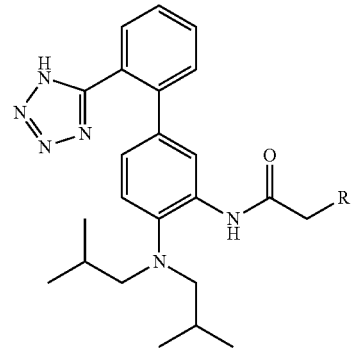

The starting material was prepared from 1B using the procedures for the preparation of 3C and 3D.

General Procedure

To a solution of N4,N4-diisobutyl-2'-(1-trityl-1H-tetrazol-5-yl)-[1,1'-biphenyl]-3,4-diamine (32.8 mg, 0.05 mmol) in DMF (1.0 ml) was added BOP (24 mg, 0.055 mmol), TEA (0.01 ml, 0.1 mmol) and corresponding acids (0.05 mmol) and the reaction mixture stirred at RT for 16 h. The reaction mixture was concentrated and stirred with TFA: DCM (0.2 ml: 0.5 ml) for 5 minutes (reactions were monitored by LCMS). Crude material was purified by reverse phase prep. HPLC using following conditions: Column: Xbridge Prep C18 19×100 mm, 5 μm. Mobile Phases: A=10 mM ammonium acetate in water, B=ACN). Flow=15 ml/min.

| Gradient | |
|---|---|
| Time (Min) | % B |
| 0.0 | 10 |
| 08.00 | X |
| 16.00 | X |
| 16.01 | 100 |
| 19.00 | 100 |

X varied depending on the retention time of each product as observed in initial LCMS analysis.

The multiple fractions of same sample were collected and evaporated to dryness using Genevac.

An aliquot of each sample were placed in 2.0 ml vial and diluted with 0.6 ml methanol and analyzed by LCMS using the following conditions for final analysis: Ascentis Express C18, 4.6×50 mm, 2.7 μm column; 4 ml/min flow; 4 min gradient from 0% B to 100% B; A=5% ACN-95% H$_2$O 10 mM NH$_4$OAc, B=95% ACN-5% H$_2$O 10 mM NH$_4$OAc, UV detection at 220 nm; and a column heater set at 45° C.

TABLE 3

| Ex. No. | Structure | M/Z (M + H)+ | Retention time |
|---|---|---|---|
| 23 | 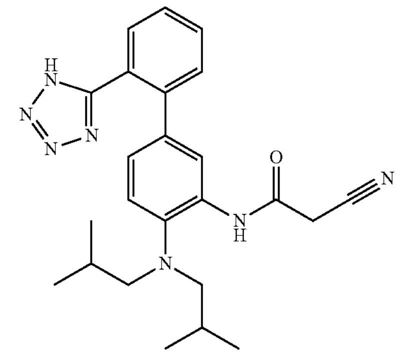 [SMILES: CC(C)CN(CC(C)C)c1ccc(-c2ccccc2-c2nnn[nH]2)cc1NC(=O)CC#N] | 432.2 | 1.95 |
| 24 | 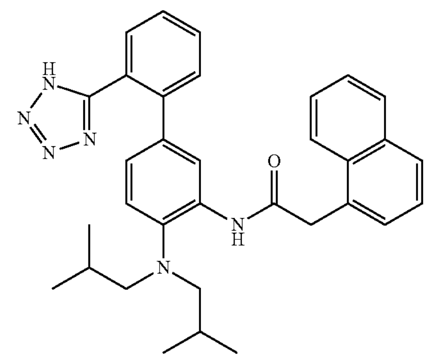 [SMILES: CC(C)CN(CC(C)C)c1ccc(-c2ccccc2-c2nnn[nH]2)cc1NC(=O)Cc1cccc2ccccc12] | 533.2 | 2.59 |
| 25 | 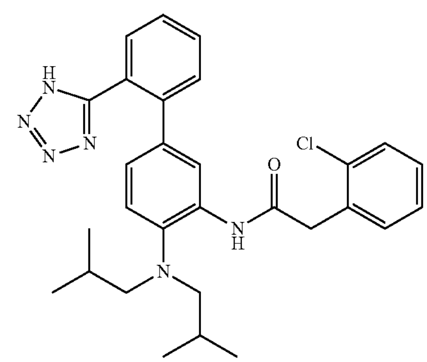 [SMILES: CC(C)CN(CC(C)C)c1ccc(-c2ccccc2-c2nnn[nH]2)cc1NC(=O)Cc1ccccc1Cl] | 517.2 | 2.51 |
| 26 | 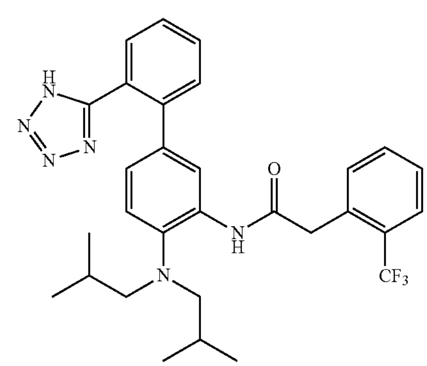 [SMILES: CC(C)CN(CC(C)C)c1ccc(-c2ccccc2-c2nnn[nH]2)cc1NC(=O)Cc1ccccc1C(F)(F)F] | 551.2 | 2.59 |

TABLE 3-continued

| Ex. No. | Structure | M/Z (M + H)+ | Retention time |
|---|---|---|---|
| 27 | 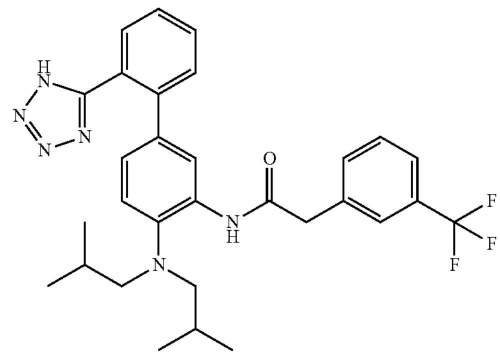 [SMILES: CC(C)CN(CC(C)C)c1ccc(-c2ccccc2-c2nnn[nH]2)cc1NC(=O)Cc1cccc(C(F)(F)F)c1] | 551.2 | 2.59 |
| 28 | 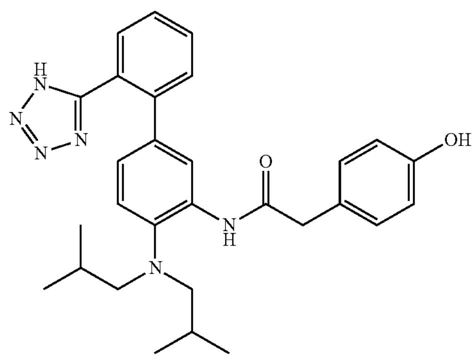 [SMILES: CC(C)CN(CC(C)C)c1ccc(-c2ccccc2-c2nnn[nH]2)cc1NC(=O)Cc1ccc(O)cc1] | 499.2 | 2.04 |
| 29 | 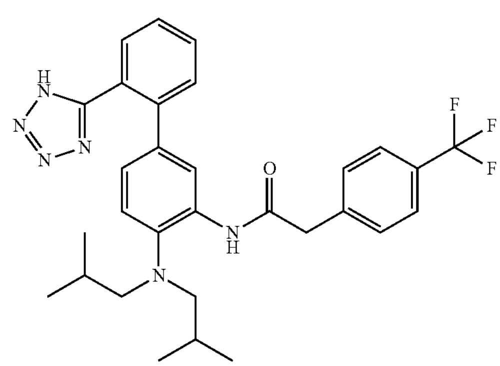 [SMILES: CC(C)CN(CC(C)C)c1ccc(-c2ccccc2-c2nnn[nH]2)cc1NC(=O)Cc1ccc(C(F)(F)F)cc1] | 551 | 2.09[j] |
| 30 | 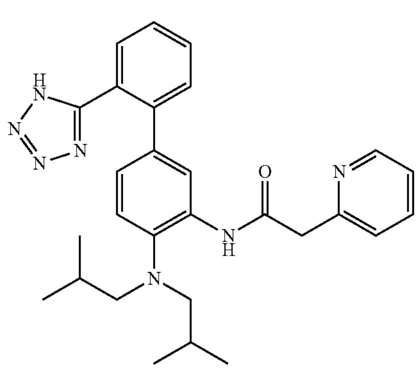 [SMILES: CC(C)CN(CC(C)C)c1ccc(-c2ccccc2-c2nnn[nH]2)cc1NC(=O)Cc1ccccn1] | 484.2 | 2.12 |

TABLE 3-continued
| Ex. No. | Structure | M/Z (M + H)+ | Retention time |
|---|---|---|---|
| 31 | 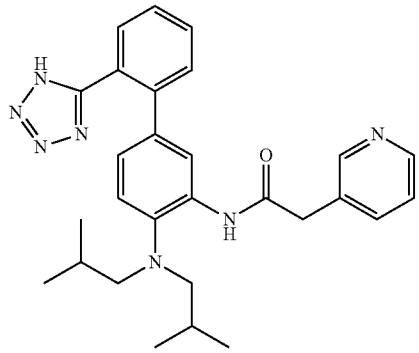 | 484.2 | 1.98 |
| 32 | 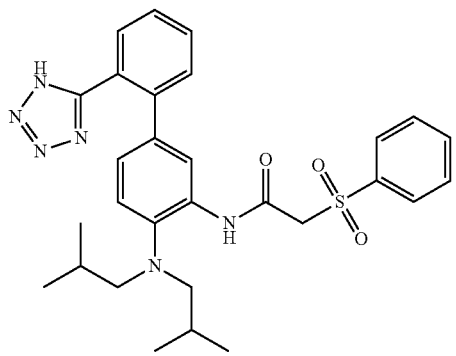 [SMILES: CC(C)CN(CC(C)C)c1ccc(-c2ccccc2-c2nnn[nH]2)cc1NC(=O)CS(=O)(=O)c1ccccc1] | 547.2 | 2.20 |
| 33 | 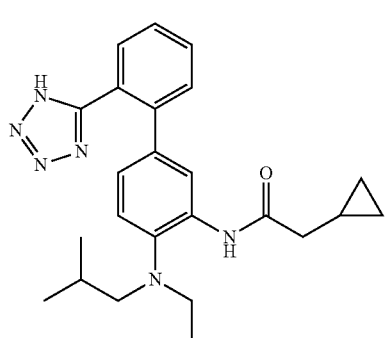 | 447.4 | 2.31 |
| 34 | 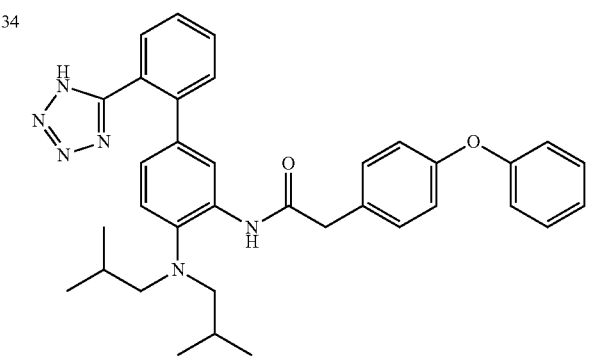 | 575.2 | 2.75 |

TABLE 3-continued
| Ex. No. | Structure | M/Z (M + H)+ | Retention time |
|---|---|---|---|
| 35 | 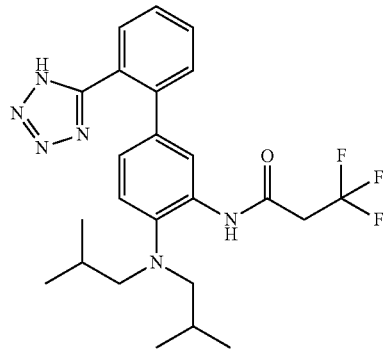 [SMILES: CC(C)CN(CC(C)C)c1ccc(-c2ccccc2-c2nnn[nH]2)cc1NC(=O)CC(F)(F)F] | 475.2 | 2.26 |
| 36 | 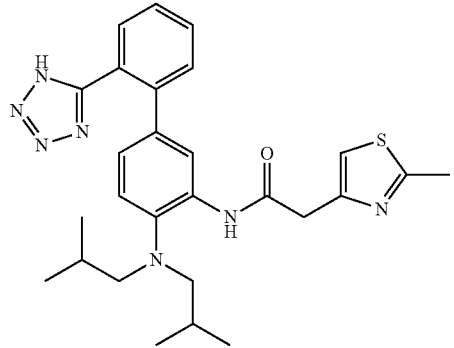 [SMILES: Cc1nc(CC(=O)Nc2cc(-c3ccccc3-c3nnn[nH]3)ccc2N(CC(C)C)CC(C)C)cs1] | 504.2 | 2.16 |
| 37 | 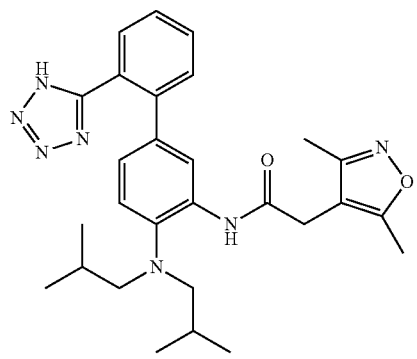 [SMILES: Cc1noc(C)c1CC(=O)Nc1cc(-c2ccccc2-c2nnn[nH]2)ccc1N(CC(C)C)CC(C)C] | 502.2 | 2.11 |
| 38 | 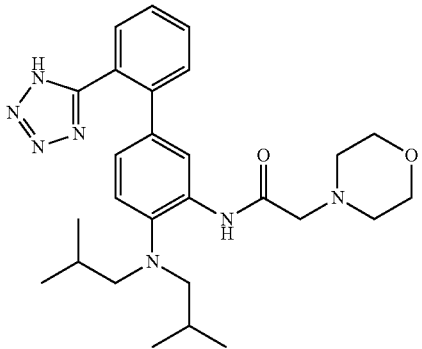 [SMILES: CC(C)CN(CC(C)C)c1ccc(-c2ccccc2-c2nnn[nH]2)cc1NC(=O)CN1CCOCC1] | 492.2 | 2.06 |

TABLE 3-continued
| Ex. No. | Structure | M/Z (M + H)+ | Retention time |
|---|---|---|---|
| 39 | 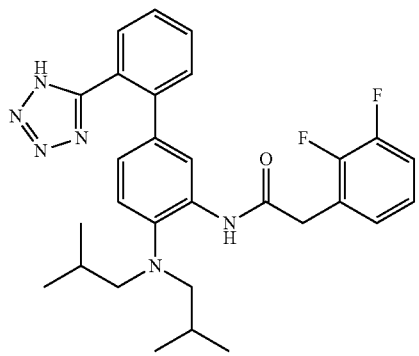 [SMILES: CC(C)CN(CC(C)C)c1ccc(-c2ccccc2-c2nnn[nH]2)cc1NC(=O)Cc1cccc(F)c1F] | 519.2 | 2.60 |
| 40 | 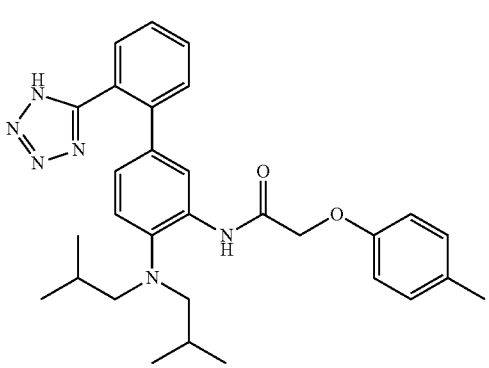 [SMILES: Cc1ccc(OCC(=O)Nc2cc(-c3ccccc3-c3nnn[nH]3)ccc2N(CC(C)C)CC(C)C)cc1] | 513.2 | 2.60 |
| 41 | 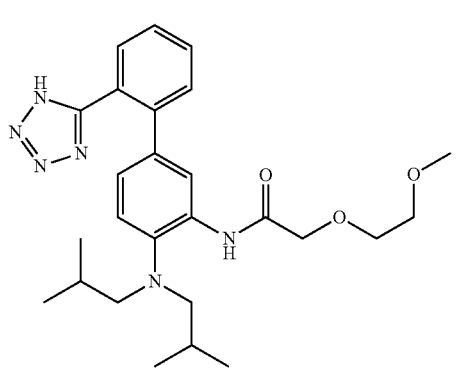 [SMILES: COCCOCC(=O)Nc1cc(-c2ccccc2-c2nnn[nH]2)ccc1N(CC(C)C)CC(C)C] | 481.2 | 2.11 |
| 42 | 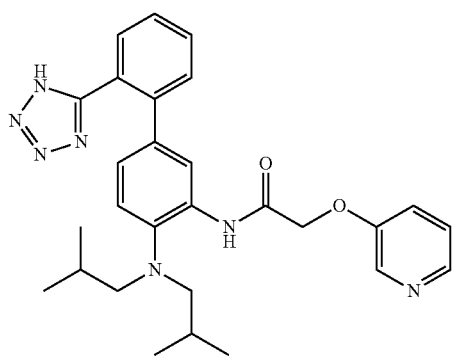 [SMILES: CC(C)CN(CC(C)C)c1ccc(-c2ccccc2-c2nnn[nH]2)cc1NC(=O)COc1cccnc1] | 500.2 | 2.02 |

TABLE 3-continued

| Ex. No. | Structure | M/Z (M + H)+ | Retention time |
|---|---|---|---|
| 43 | 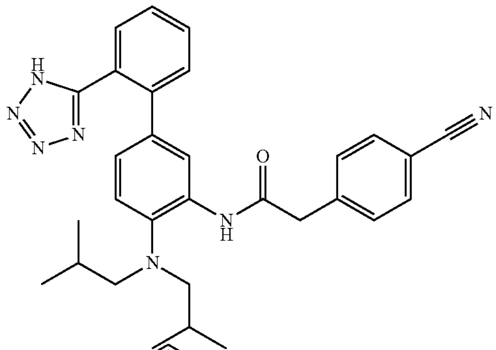 [SMILES: CC(C)CN(CC(C)C)c1ccc(-c2ccccc2-c2nnn[nH]2)cc1NC(=O)Cc1ccc(C#N)cc1] | 508.2 | 2.26 |
| 44 | 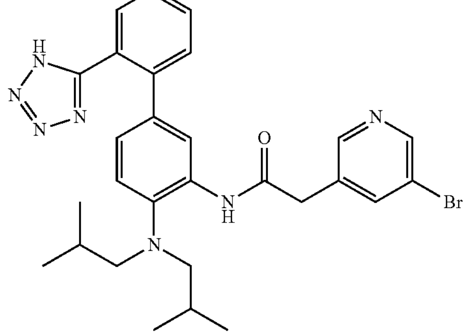 | 562.2 | 2.23 |

Example 45

4-Chlorophenyl (4-(diisobutylamino)-2'-(1H-tetrazol-5-yl)-[1,1'-biphenyl]-3-yl)carbamate

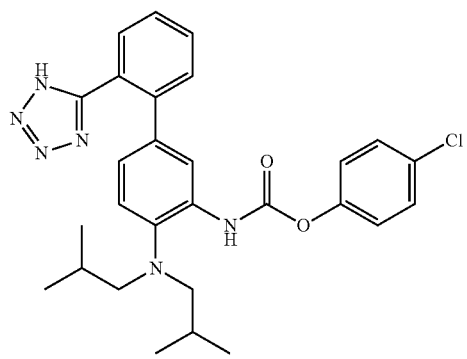 [SMILES: CC(C)CN(CC(C)C)c1ccc(-c2ccccc2-c2nnn[nH]2)cc1NC(=O)Oc1ccc(Cl)cc1]

Part A: 4-Nitrophenyl 4-(diisobutylamino)-2'-(1H-tetrazol-5-yl)biphenyl-3-ylcarbamate

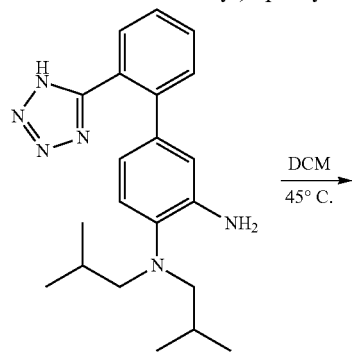

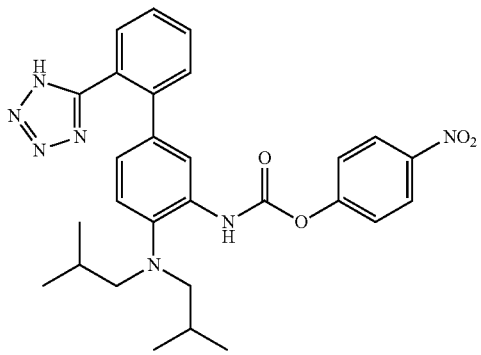

A stirred, cooled (0° C.) solution of N4,N4-diisobutyl-2'-(1H-tetrazol-5-yl)-[1,1'-biphenyl]-3,4-diamine (0.700 g, 1.921 mmol) in dry DCM under nitrogen was treated with 4-nitrophenyl carbonochloridate (0.387 g, 1.921 mmol) dissolved in DCM. The reaction mixture was heated to 45° C. and maintained for 30 minutes, and then concentrated to afford 4-nitrophenyl 4-(diisobutylamino)-2'-(1H-tetrazol-5-yl)biphenyl-3-ylcarbamate (1.0 g, 98% yield). MS(ES): m/z=530.2 [M+H]+.

Example 45

4-Chlorophenyl (4-(diisobutylamino)-2'-(1H-tetrazol-5-yl)-[1,1'-biphenyl]-3-yl)carbamate

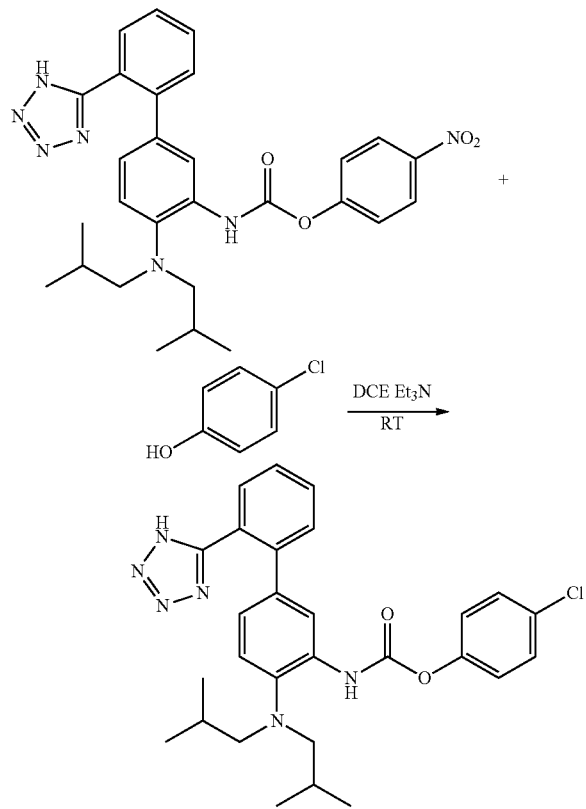

A solution of 4-nitrophenyl (4-(diisobutylamino)-2'-(1H-tetrazol-5-yl)-[1,1'-biphenyl]-3-yl)carbamate (0.05 g, 0.094 mmol) and 4-(benzyloxy)phenol (0.023 g, 0.113 mmol) in DCM (1 mL) was treated with Et$_3$N (0.020 mL, 0.142 mmol) and stirred at rt for 2 h. It was then concentrated and purified by prep HPLC to afford (8 mg, 14%) of 4-chlorophenyl (4-(diisobutylamino)-2'-(1H-tetrazol-5-yl)-[1,1'-biphenyl]-3-yl)carbamate MS(ES): m/z=519 [M+H]$^+$. HPLC T$_r$: 2.15$^v$.

Example 46

2-(4-methylphenyl)-N-[2-(1H-pyrazol-1-yl)-5-[2-(1H-1,2,3,4-tetrazol-5-yl)phenyl]phenyl]acetamide

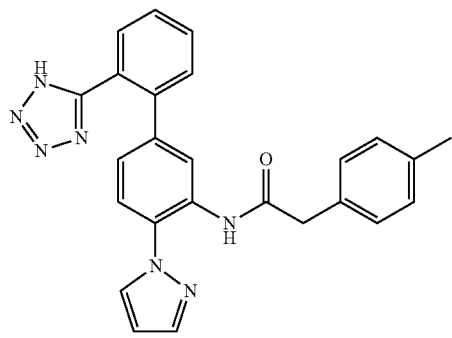 [SMILES: Cc1ccc(CC(=O)Nc2cc(-c3ccccc3-c3nnn[nH]3)ccc2-n2cccn2)cc1]

46A: 1-(4-bromo-2-nitrophenyl)-1H-pyrazole

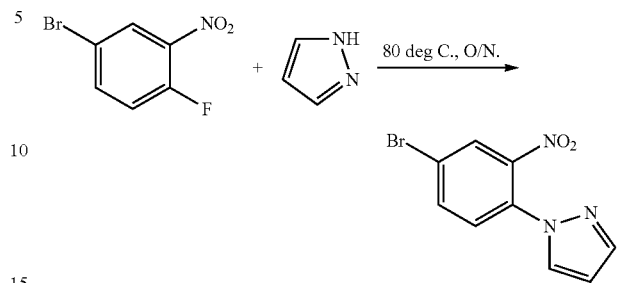

To a stirred solution of 4-bromo-1-fluoro-2-nitrobenzene (100 mg, 0.455 mmol) and 1H-pyrazole (37.1 mg, 0.545 mmol) in DMF (1 mL) was added potassium carbonate (188 mg, 1.364 mmol) at ambient temperature. The reaction mixture was then heated at 80 deg C., overnight. The reaction mixture was cooled to RT, diluted with ethyl acetate, washed with water and brine, dried over Na$_2$SO$_4$ and concentrated to afford 120 mg of yellow liquid. HPLC Tr: 1.84$^v$.

46B: 5-bromo-2-(1H-pyrazol-1-yl)aniline

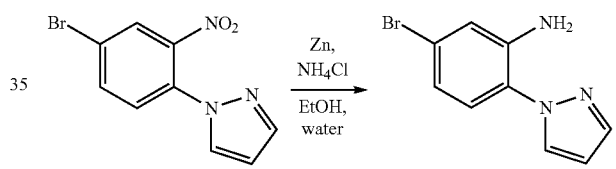

To a stirred solution of 1-(4-bromo-2-nitrophenyl)-1H-pyrazole (3.5 g, 13.06 mmol) in ethanol (35 mL) was added water (7.0 mL) followed by zinc (8.54 g, 131 mmol) and ammonium chloride (6.98 g, 131 mmol) at 0 deg C. The reaction mixture was slowly brought to RT and stirred 3 h. The reaction mixture was diluted with DCM, and filtered through a cellite bed. The filtrate was washed with water, dried over Na$_2$SO$_4$, and concentrated. The crude material was purified by silica gel column chromatography (230-400 mesh), 10% EtOAc:PE as a solvent. Concentration of the appropriate fractions afforded 2.5 g of of 5-bromo-2-(1H-pyrazol-1-yl)aniline as an off-yellow solid. MS(ES): m/z=238 [M+H]$^+$.

46C: 5-(5,5-dimethyl-1,3,2-dioxaborinan-2-yl)-2-(1H-pyrazol-1-yl)aniline

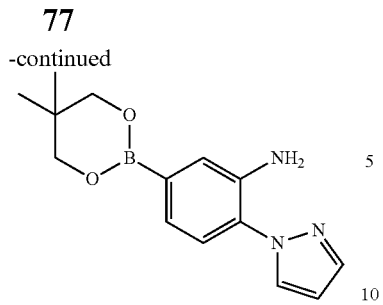

5-bromo-2-(1H-pyrazol-1-yl)aniline (2.25 g, 9.45 mmol), 5,5,5',5'-tetramethyl-2,2'-bi(1,3,2-dioxaborinane) (3.84 g, 17.01 mmol), PdCl2(dppf)-CH₂Cl₂Adduct (0.347 g, 0.425 mmol), and potassium acetate (4.17 g, 42.5 mmol) were combined in 50 ml RB, and DMSO (22.5 mL) was added. Evacuated and degassed with N₂, then heated at 80 deg C. for O/N. Workup: The reaction mixture was cooled to RT, diluted with ethyl acetate, water and extracted twice, the combined organics were washed with brine, dried over Na₂SO₄, concentrated. The crude material was purified by silica gel (230-400 mesh) column chromatography, 40-55% EtOAc:PE as a solvent to get the pure pdt. The solvent was concentrated to afford, after concentration, 1.7 g of 5-(5,5-dimethyl-1,3,2-dioxaborinan-2-yl)-2-(1H-pyrazol-1-yl)aniline as a brown solid. HPLC Tr: 1.35ᵛ.

46D: 3'-amino-4'-(1H-pyrazol-1-yl)-[1,1'-biphenyl]-2-carbonitrile

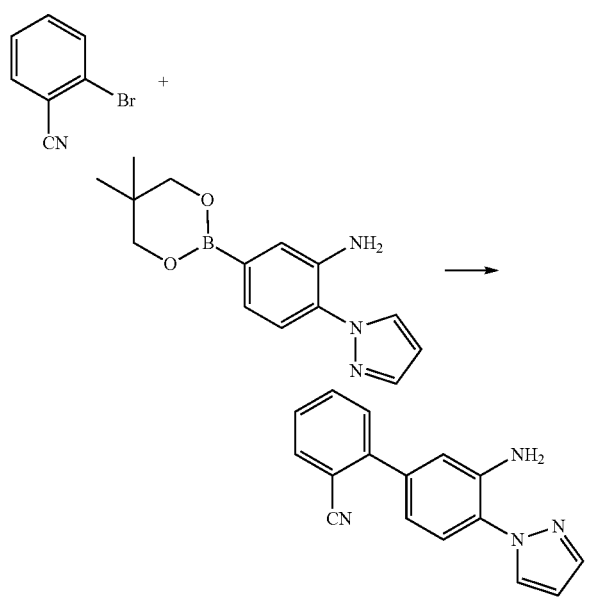

5-(5,5-dimethyl-1,3,2-dioxaborinan-2-yl)-2-(1H-pyrazol-1-yl)aniline (0.9 g, 3.32 mmol), 2-bromobenzonitrile (0.725 g, 3.98 mmol), tripotassium phosphate (2.114 g, 9.96 mmol) and PdCl₂(dppf)-CH₂Cl₂Adduct (0.542 g, 0.664 mmol) were combined in a 25 ml RB, Dioxane (9 mL) was added. The flask was evacuated and degassed with N₂, then heated at 80 deg C. for O/N. The solvent was removed, and the residue was diluted with water and extracted twice with ethyl acetate. The combined organics were washed with brine, dried over Na₂SO₄, concentrated in vacuo. The residue was purified by silica gel column chromatography and 20% ethyl acetate/Hexane as solvent to give the 3'-amino-4'-(1H-pyrazol-1-yl)-[1,1'-biphenyl]-2-carbonitrile (550 mg, 2.113 mmol, 63.7% yield) as an orange solid. MS(ES): m/z=261 [M+H]⁺. HPLC Tr: 1.83ᵛ.

46E: 4-(1H-pyrazol-1-yl)-2'-(1H-tetrazol-5-yl)-[1,1'-biphenyl]-3-amine

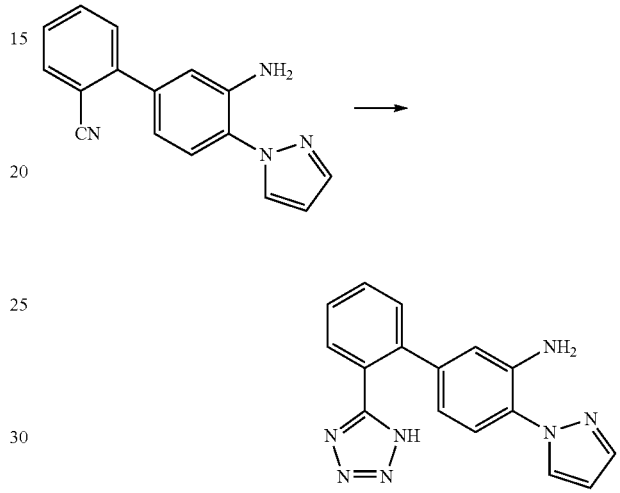

To a solution of 3'-amino-4'-(1H-pyrazol-1-yl)-[1,1'-biphenyl]-2-carbonitrile (820 mg, 3.15 mmol) in Toluene (9 mL) was added azidotributyltin (6.04 mL, 22.05 mmol) at ambient temperature. This mixture was refluxed for 24 h then cooled. The solvent was removed completely, and the resultant residue was dissolved in Ethyl acetate, washed with 10% KF solution twice, brine, dried over Na₂SO₄ and concentrated. The crude material was purified by ISCO. The solvent was concentrated to afford 4-(1H-pyrazol-1-yl)-2'-(1H-tetrazol-5-yl)-[1,1'-biphenyl]-3-amine (386 mg, 1.273 mmol, 40.4% yield) as a yellow solid. MS(ES): m/z=304 [M+H]⁺. HPLC Tr: 1.54ᵛ.

46. 2-(4-methylphenyl)-N-[2-(1H-pyrazol-1-yl)-5-[2-(1H-1,2,3,4-tetrazol-5-yl)phenyl]phenyl]acetamide

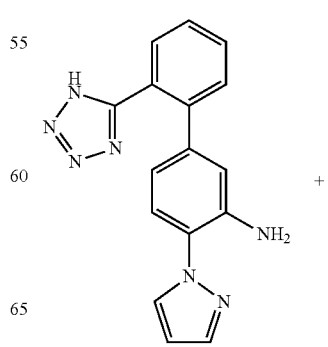

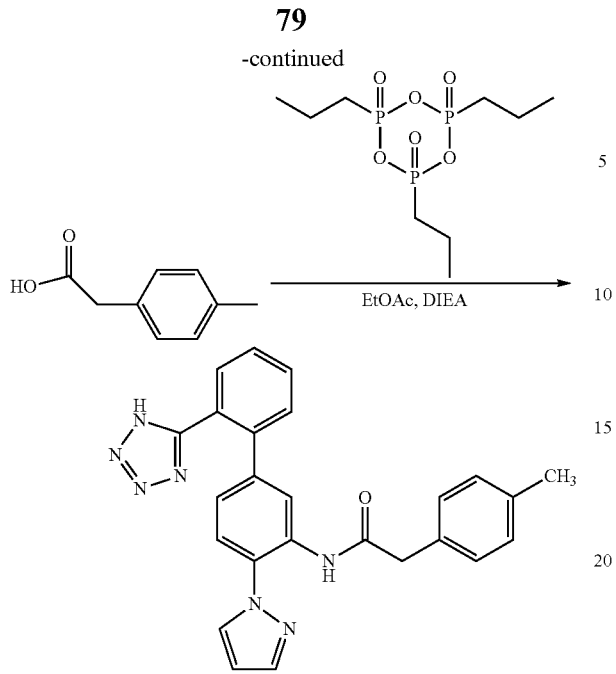

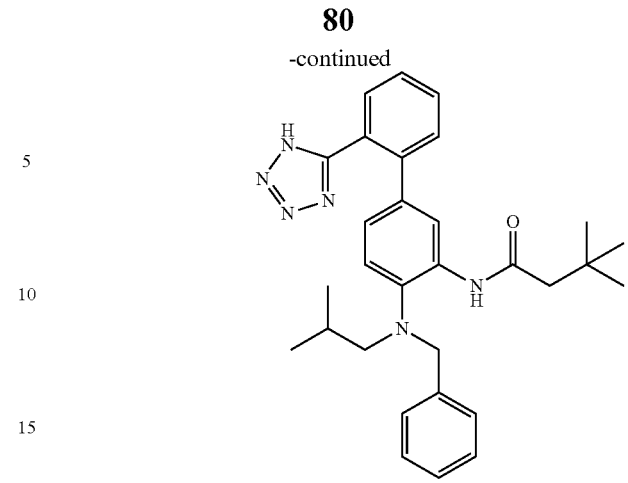

To a solution of 4-(1H-pyrazol-1-yl)-2'-(1H-tetrazol-5-yl)-[1,1'-biphenyl]-3-amine (30.0 mg, 0.099 mmol) and 2-(p-tolyl)acetic acid (29.7 mg, 0.198 mmol) in Ethyl acetate (2.0 mL) was added DIPEA (0.035 mL, 0.198 mmol) followed by 2,4,6-tripropyl-1,3,5,2,4,6-trioxatriphosphinane 2,4,6-trioxide (94 mg, 0.148 mmol) at 0° C., the reaction mixture was brought to room temperature, stirred over night. The reaction mixture was diluted with ethylacetate, washed 1× with water, 1x with 10% NaHCO3 solution, 1x with brine and then dried over $Na_2SO_4$ and concentrated. The crude material was then purified by reverse phase preparative HPLC to afford N-(4-(1H-pyrazol-1-yl)-2'-(1H-tetrazol-5-yl)-[1,1'-biphenyl]-3-yl)-2-(p-tolyl)acetamide (17.5 mg, 0.040 mmol, 40.6% yield) as an off-white solid. MS(ES): m/z=434.2 [M−H]$^−$. HPLC Tr: 1.74$^v$.

The title compound was prepared from 3D and 3,3-dimethylburyric acid employing the general procedure used for the synthesis of Example 3. $^1$H NMR (400 MHz, DMSO-$d_6$) δ ppm 8.63 (s, 1H), 8.0 (brs, 1 H), 7.53-7.68 (m, 4H), 7.17-7.32 (m, 5H), 7.07 (d, 1H, J=8.4 Hz), 6.65 (d, 1H, J=8.8 Hz), 3.95 (s, 2H), 2.68 (d, 2H, J=6.8 Hz), 2.12 (s, 2H), 1.64-1.71 (m, 1H), 0.96 (s, 9 H), 0.85 (d, 1H, J=6.4 Hz). MS(ES): m/z=497 [M+H]$^+$, HPLC Tr: 2.08$^v$.

Example 47

N-(4-(Benzyl(isobutyl)amino)-2'-(2H-tetrazol-5-yl)biphenyl-3-yl)-3,3-dimethylbutanamide Example 48

(R)—N-(4-(Benzyl(isobutyl)amino)-2'-(1H-tetrazol-5-yl)biphenyl-3-yl)-2-hydroxy-2-phenylacetamide

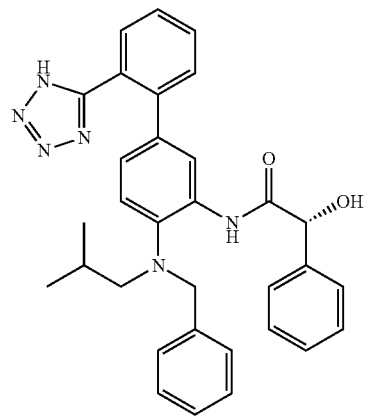 [SMILES: CC(C)CN(Cc1ccccc1)c1ccc(-c2ccccc2-c2nnn[nH]2)cc1NC(=O)[C@H](O)c1ccccc1]

48A. (R)-2-(4-(Benzyl(isobutyl)amino)-2'-(2-trityl-2H-tetrazol-5-yl)biphenyl-3-ylamino)-2-oxo-1-phenylethyl acetate

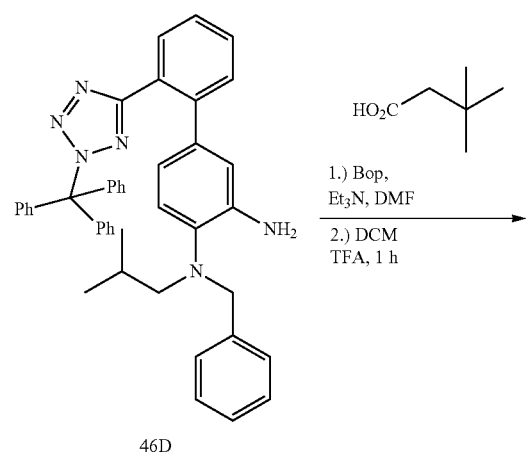

46D

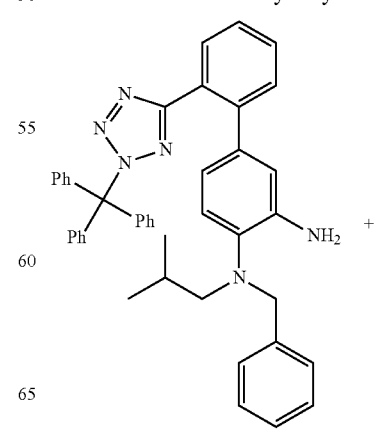

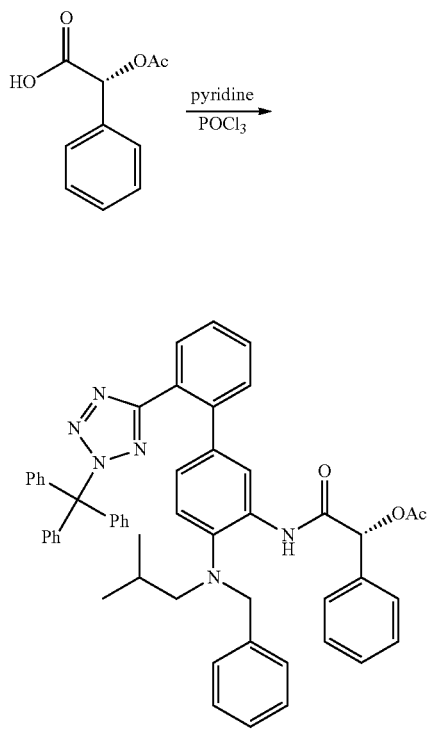

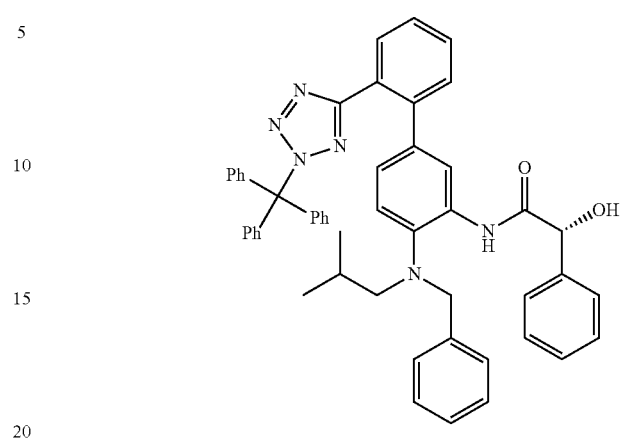

The compound was prepared from N4-benzyl-N4-isobutyl-2'-(2-trityl-2H-tetrazol-5-yl)biphenyl-3,4-diamine (3D) by the general procedure used for the synthesis of 3E. MS(ES): m/z=817.72 [M+H]$^+$, HPLC T$_r$: 2.76$^v$.

48B. (R)—N-(4-(Benzyl(isobutyl)amino)-2'-(2-trityl-2H-tetrazol-5-yl)biphenyl-3-yl)-2-hydroxy-2-phenylacetamide To a stirred, cooled (0° C.) solution of (R)-2-((4-(benzyl(isobutyl)amino)-2'-(2-trityl-2H-tetrazol-5-yl)-[1,1'-biphenyl]-3-yl)amino)-2-oxo-1-phenylethyl acetate (0.03 g, 0.037 mmol), THF (1.0 mL), and water (0.5 mL) was added lithium hydroxide monohydrate (1.54 mg, 0.037 mmol). The reaction mixture was stirred at room temperature for 1 h. The reaction mixture was diluted with ethyl acetate and acidified to neutral pH with 1.5 N HCl. The aqueous layer was extracted with ethyl acetate twice, and the combined organic extracts dried over sodium sulfate, and concentrated to afford (R)—N-(4-(benzyl(isobutyl)amino)-2'-(2-trityl-2H-tetrazol-5-yl)biphenyl-3-yl)-2-hydroxy-2-phenylacetamide (25 mg, 88% yield). MS(ES): m/z=776 [M+H]$^+$. HPLC T$_r$: 1.33$^k$.

48. (R)—N-(4-(Benzyl(isobutyl)amino)-2'-(1H-tetrazol-5-yl)biphenyl-3-yl)-2-hydroxy-2-phenylacetamide

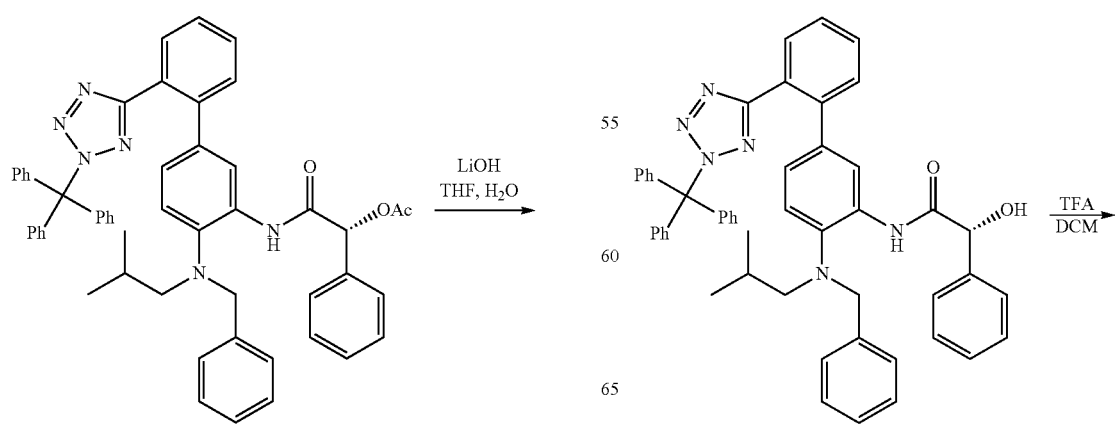

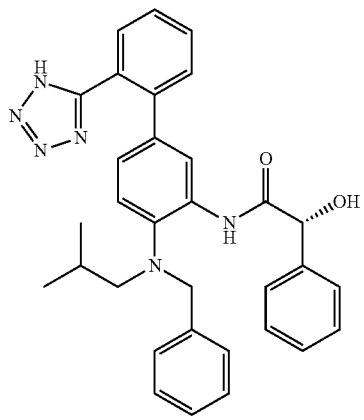

The compound was prepared from (R)—N-(4-(benzyl (isobutyl)amino)-2'-(1H-tetrazol-5-yl)biphenyl-3-yl)-2-hydroxy-2-phenylacetamide to (R)—N-(4-(benzyl(isobutyl) amino)-2'-(1H-tetrazol-5-yl)biphenyl-3-yl)-2-hydroxy-2-phenylacetamide by the general procedure used for the synthesis of Example 3. MS(ES): m/z=533.2 [M+H]⁺, HPLC T$_r$: 2.07$^v$.

Example 49

N-(4-(diisobutylamino)-2'-(1H-tetrazol-5-yl)-[1,1'-biphenyl]-3-yl)-2-(4-iodophenyl)acetamide

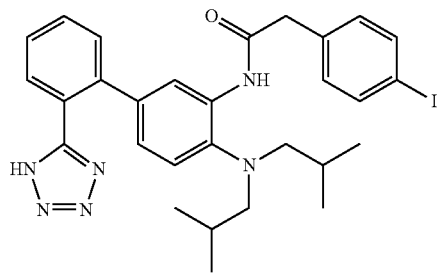 [SMILES: CC(C)CN(CC(C)C)c1ccc(-c2ccccc2-c2nnn[nH]2)cc1NC(=O)Cc1ccc(I)cc1]

49A. 4-(5,5-Dimethyl-1,3,2-dioxaborinan-2-yl)-N1,N1-diisobutylbenzene-1,2-diamine

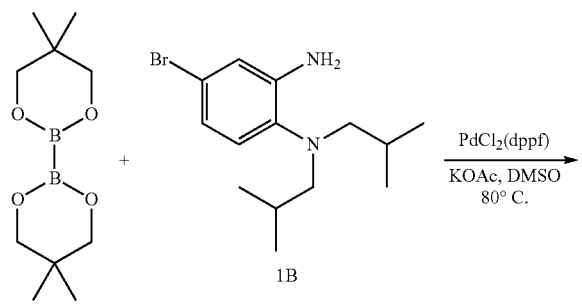

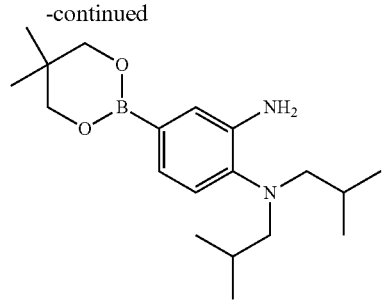

4-Bromo-N1,N1-diisobutylbenzene-1,2-diamine (15.0 g, 50.1 mmol), 5,5,5',5'-tetramethyl-2,2'-bi(1,3,2-dioxaborinane) (20.38 g, 90.0 mmol), PdCl$_2$(dppf)-CH$_2$Cl$_2$Adduct (1.842 g, 2.256 mmol), and potassium acetate (22.14 g, 226 mmol) were combined in a 250 mL RB flask, and DMSO (Volume: 150 mL) was added. The reacting vessel was evacuated and filled with argon 3×, then heated at 80° C. for 16 h. The reaction was cooled to RT diluted with ethyl acetate and filtered. The filtrate was washed with water, dried, and concentrated to afford crude solid. Chromatography on silica gel (EtOAc-hexanes gradient) afforded 4-(5, 5-dimethyl-1,3,2-dioxaborinan-2-yl)-N1,N1-diisobutylbenzene-1,2-diamine (13.0 g, 78% yield) as a white solid. MS(ES): m/z=265, (These mass correspond to [M+H]⁺ for free boronic acid. No significant [M+H]⁺ is seen for the parent compound.) ¹H NMR (400 MHz, DMSO-d$_6$) δ ppm 7.07 (d, 1 H, J=1.2 Hz), 6.92-6.96 (m, 2H), 4.66 (brs, 2H), 3.70 (s, 4H), 2.57 (d, 4H, J=7.2 Hz), 1.66-1.69 (m, 2H), 0.94 (s, 6H), 0.84 (d, 12H, J=6.8 Hz).

49B. 3'-Amino-4'-(diisobutylamino)biphenyl-2-carbonitrile

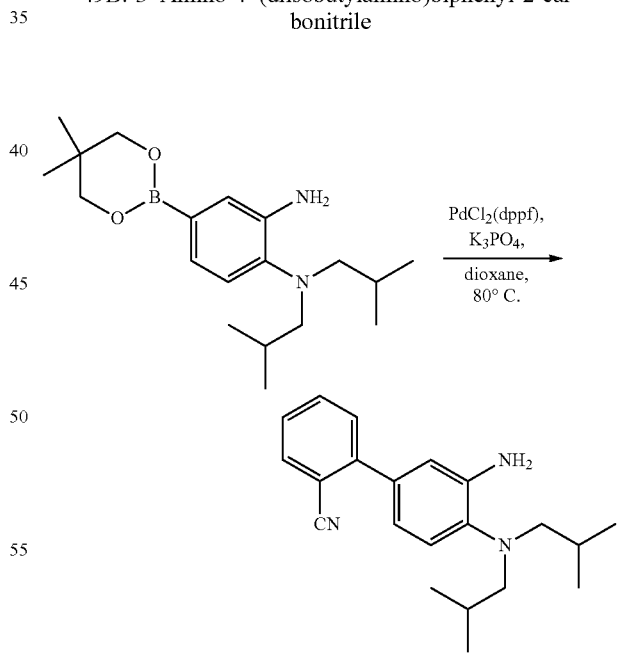

49B was prepared from 4-(5,5-dimethyl-1,3,2-dioxaborinan-2-yl)-N1,N1-diisobutylbenzene-1,2-diamine by the procedure set out below.

4-(5,5-Dimethyl-1,3,2-dioxaborinan-2-yl)-N1,N1-diisobutylbenzene-1,2-diamine (7.5 g, 22.57 mmol), 2-bromobenzonitrile (4.93 g, 27.1 mmol), PdCl$_2$(dppf)-CH$_2$Cl$_2$Adduct (3.69 g, 4.51 mmol) and potassium phosphate, tribasic (14.37 g, 67.7 mmol) were added to a 250 mL RB flask, evacuated and filled with argon 3× followed by 75 mL of dioxane. The reaction mixture was heated at 80° C. for 16 h. The reaction was cooled to room temperature and concentrated. The residue was dissolved in ethyl acetate, washed with water, dried, and concentrated to afford the crude product. Chromatography on silica gel (EtOAc-hexanes gradient) afforded 3'-amino-4'-(diisobutylamino)biphenyl-2-carbonitrile (6.2 g, 85.0% yield). $^1$H NMR (400 MHz, CDCl$_3$) δ ppm 7.72 (dd, 1H, J=8.0, 1.2 Hz), 7.58-7.61 (m, 1H), 7.50 (dd, 1 H, J=8.0, 1.2 Hz), 7.37-7.39 (m, 1H), 7.13-7.15 (m, 1H), 6.89-6.92 (m, 2H), 4.12 (2H, brs), 2.65 (d, 4H, J=7.2 Hz), 1.77-1.84 (m, 2H), 0.92 (d, 12H, J=6.4 Hz). MS(ES): m/z=322.2 [M+H]$^+$.

49C. N4,N4-Diisobutyl-2'-(1H-tetrazol-5-yl)biphenyl-3,4-diamine

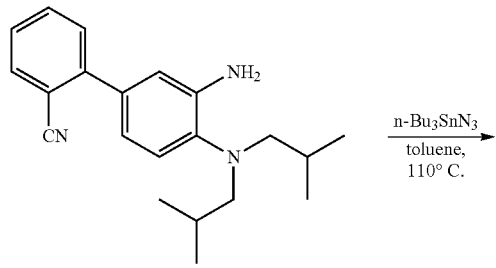

3'-Amino-4'-(diisobutylamine)biphenyl-2-carbonitrile (51D) (3.0 g, 9.33 mmol) and azidotributyltin (17.90 mL, 65.33 mmol) in toluene (60 mL) were heated at 110° C. for 40 hours. The reaction was cooled to room temperature and washed with 10% KF aqueous solution, dried, and concentrated to afford crude liquid product. Chromatography on silica gel (EtOAc-hexanes gradient) afforded N4,N4-diisobutyl-2'-(1H-tetrazol-5-yl)biphenyl-3,4-diamine (3.5 g) as yellow oil. MS(ES): m/z=365.2 [M+H]$^+$.

49. N-(4-(diisobutylamino)-2'-(1H-tetrazol-5-yl)-[1,1'-biphenyl]-3-yl)-2-(4-iodophenyl)acetamide

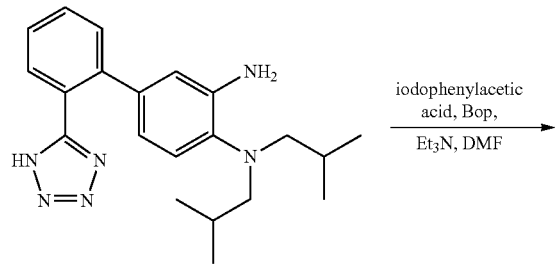

A solution of N4,N4-diisobutyl-2'-(1H-tetrazol-5-yl)-[1,1'-biphenyl]-3,4-diamine (0.1 g, 0.274 mmol) in DMF (2 mL) was treated with triethylamine (0.076 mL, 0.549 mmol) followed by BOP (0.133 g, 0.302 mmol). This solution was stirred at RT for 3 h then purified by flash chromatography (gradient elution with EtOAc-hexanes).
Concentration of the appropriate fractions afforded N-(4-(diisobutylamino)-2'-(1H-tetrazol-5-yl)-[1,1'-biphenyl]-3-yl)-2-(4-iodophenyl)acetamide as an off-white powder.
LCMS (M+H)$^+$: 609 HPLC Tr$^k$: 1.20.

Intermediate Example 3

4-(3,3-Difluoropyrrolidin-1-yl)-2'-(1H-tetrazol-5-yl) biphenyl-3-amine

A.
1-(4-Bromo-2-nitrophenyl)-3,3-difluoropyrrolidine

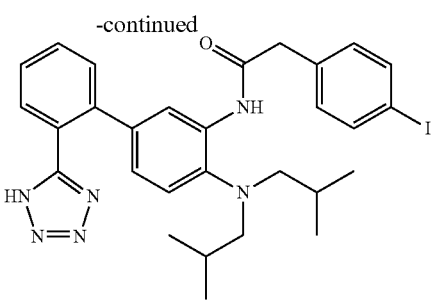

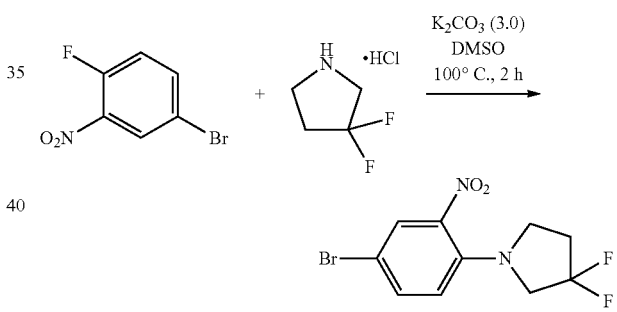

To a stirred solution of 4-bromo-1-fluoro-2-nitrobenzene (3 g, 13.64 mmol) and 3,3-difluoropyrrolidine hydrochloride (2.94 g, 20.45 mmol) in DMSO (12 mL), was added K$_2$CO$_3$ (5.65 g, 40.9 mmol), and the reaction was stirred at 100° C. for 2 h. The reaction mixture was cooled to room temperature, diluted with EtOAc, washed with water then brine, dried over Na$_2$SO$_4$ and concentrated to afford 1-(4-bromo-2-nitrophenyl)-3,3-difluoropyrrolidine (4.0 g). $^1$H NMR (400 MHz, CDCl$_3$) δ ppm 7.89 (d, 1H, J=2.4 Hz), 7.52 (dd, 1H, J=8.8, 2.4 Hz), 6.79 (d, 1H, J=9.2 Hz), 3.44-3.55 (m, 4H), 2.43-2.53 (m, 2H). MS(ES): m/z=307 [M+H]$^+$.

B. 5-Bromo-2-(3,3-difluoropyrrolidin-1-yl)aniline

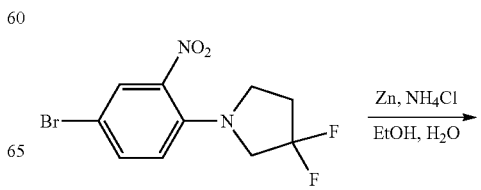

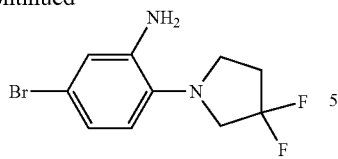

Prepared from 1-(4-bromo-2-nitrophenyl)-3,3-difluoropyrrolidine by the general procedure used for the conversion of 1A to 1B. MS(ES): m/z=277. [M+H]$^+$. HPLC T$_r$: 1.95'

C. 2-(3,3-Difluoropyrrolidin-1-yl)-5-(5,5-dimethyl-1,3,2-dioxaborinan-2-yl)aniline

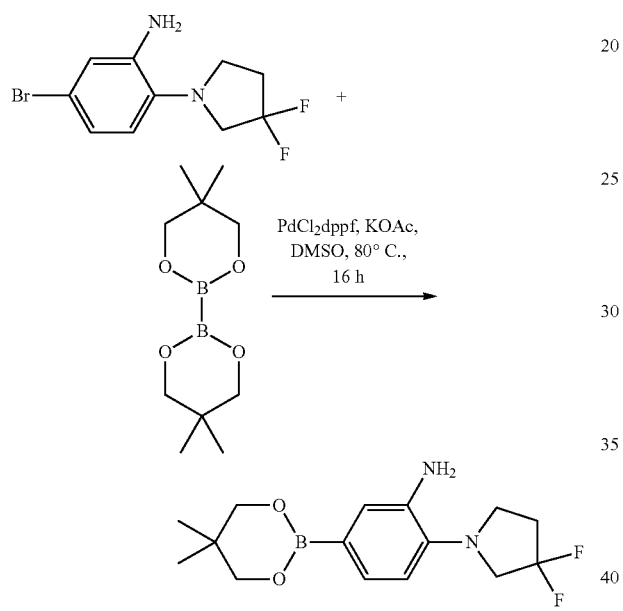

Prepared from 5-bromo-2-(3,3-difluoropyrrolidin-1-yl) aniline by the general procedure used for the conversion of 1B to 49A. MS(ES): m/z=243. (The mass corresponds to [M+H]$^+$ for free boronic acid. No significant [M+H]$^+$ is seen for the parent compound.) HPLC T$_r$: 1.58$^v$ D. 3'-Amino-4'-(3,3-difluoropyrrolidin-1-yl)biphenyl-2-carbonitrile

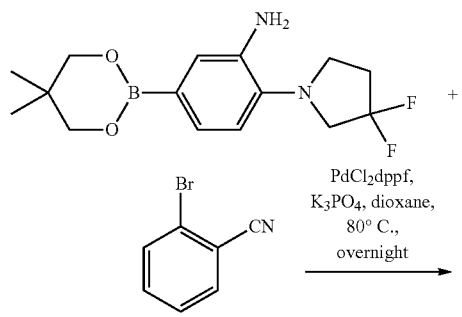

Prepared from 2-(3,3-difluoropyrrolidin-1-yl)-5-(5,5-dimethyl-1,3,2-dioxaborinan-2-yl)aniline by the general procedure used for the conversion of 49A to 49B. MS(ES): m/z=300. [M+H]$^+$. HPLC T$_r$: 0.91$^k$ 4-(3,3-Difluoropyrrolidin-1-yl)-2'-(1H-tetrazol-5-yl) biphenyl-3-amine

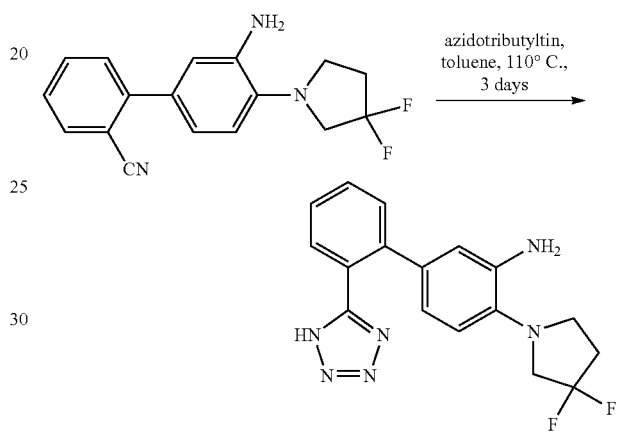

The title compound was prepared from 3'-amino-4'-(3,3-difluoropyrrolidin-1-yl)-[1,1'-biphenyl]-2-carbonitrile by the general procedure used for the conversion of 49B to 49C. MS(ES): m/z=343. [M+H]$^+$.

Intermediate Example 4

4-(5-Benzyl-2,5-diazabicyclo[2.2.1]heptan-2-yl)-2'-(1H-tetrazol-5-yl)-biphenyl-3-amine A. 2-Benzyl-5-(4-bromo-2-nitrophenyl)-2,5-diazabicyclo[2.2.1]heptanes

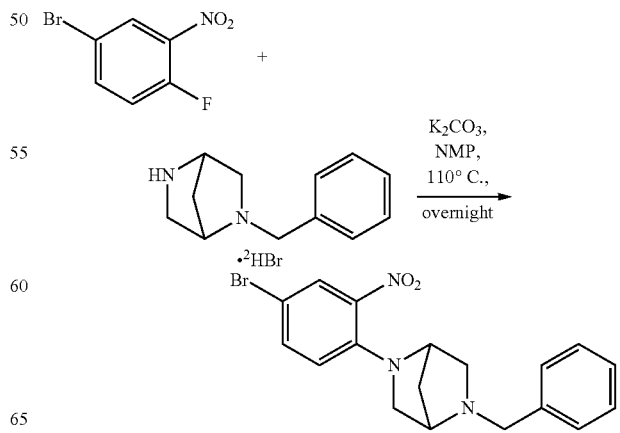

To a solution of 4-bromo-1-fluoro-2-nitrobenzene (2.7 g, 12.27 mmol) and 2-benzyl-2,5-diazabicyclo[2.2.1]heptanes dihydrobromide (4.73 g, 13.50 mmol) in NMP (40.5 mL) was added K₂CO₃ (7.63 g, 55.2 mmol)' and the reaction was stirred at 110° C. overnight. The reaction mixture was cooled to room temperature, diluted with EtOAc, and washed with water (3×). The organic layer was dried over Na₂SO₄, filtered and concentrated in vacuum to give a crude semi solid. Purification using flash column chromatography (20% to 50% ethyl acetate/hexane gradient) provided 2-benzyl-5-(4-bromo-2-nitrophenyl)-2,5-diazabicyclo[2.2.1]heptanes (5.0 g). ¹H NMR (400 MHz, CDCl₃) δ ppm 7.89 (d, 1H, J=2.4 Hz), 7.41 (dd, 1H, J=9.0, 2.8 Hz), 7.22-7.31 (m, 5H), 6.72 (d, 1H, J=9.2 Hz), 4.26 (s, 1H), 3.64 (s, 2H), 3.49-3.54 (m, 2H), 2.93 (dd, 1H, J=10.0, 2.0 Hz), 2.83 (dd, 1H, J=10.0, 1.2 Hz), 2.71 (dd, 1H, J=9.4, 1.6 Hz), 2.03-2.06 (m, 1H), 1.93 (d, 1H, J=10.0 Hz). MS(ES): m/z=388 [M+H]⁺.

B. 2-(5-Benzyl-2,5-diazabicyclo[2.2.1]heptan-2-yl)-5-bromoaniline

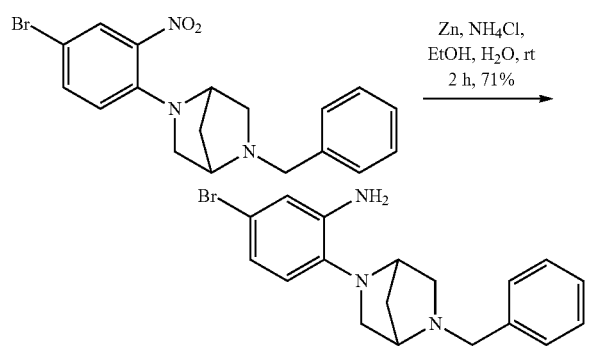

Prepared from 2-benzyl-5-(4-bromo-2-nitrophenyl)-2,5-diazabicyclo[2.2.1]heptanes to 2-(5-benzyl-2,5-diazabicyclo[2.2.1]heptan-2-yl)-5-bromoaniline by the general procedure used for the conversion of 1A to 1B. MS(ES): m/z=360 [M+H]⁺.

C. 3'-Amino-4'-(5-benzyl-2,5-diazabicyclo[2.2.1]heptan-2-yl)biphenyl-2-carbonitrile

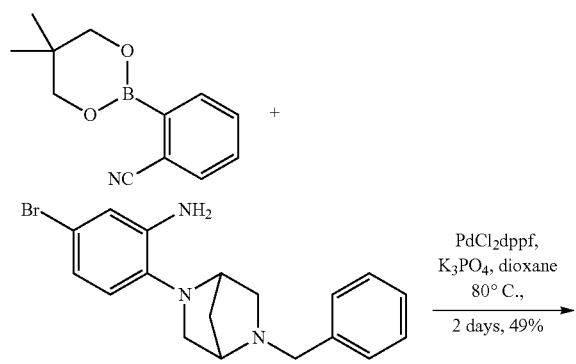

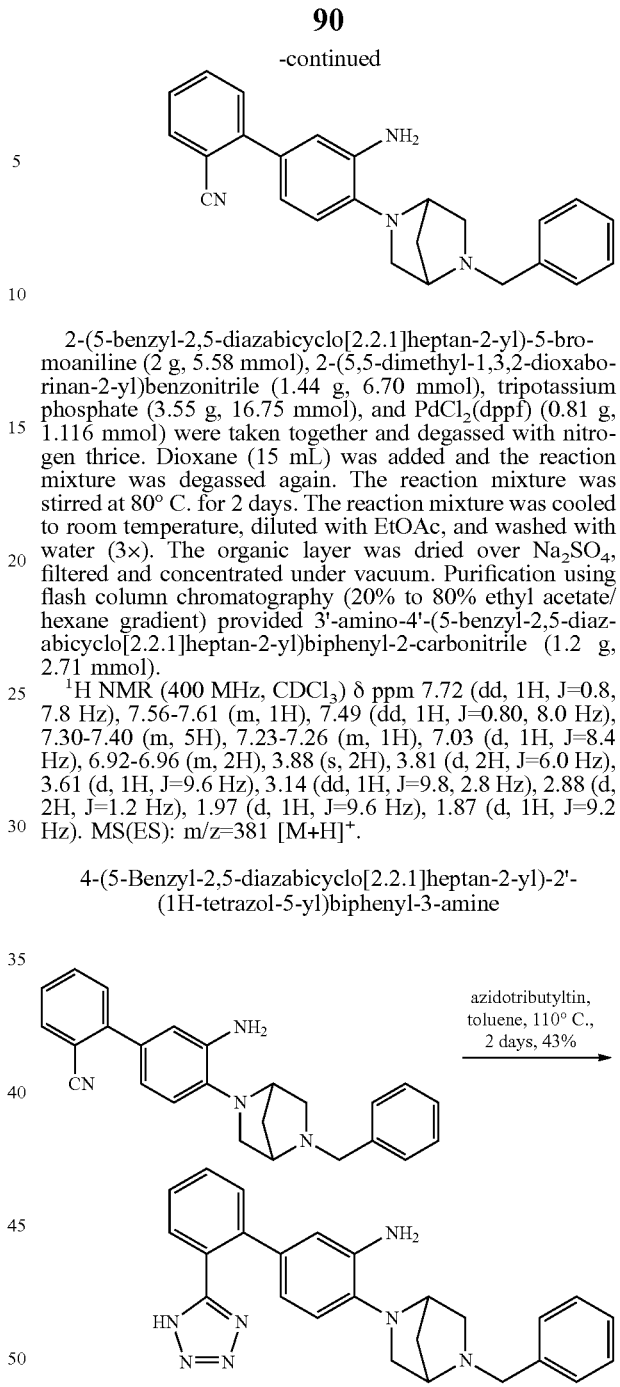

2-(5-benzyl-2,5-diazabicyclo[2.2.1]heptan-2-yl)-5-bromoaniline (2 g, 5.58 mmol), 2-(5,5-dimethyl-1,3,2-dioxaborinan-2-yl)benzonitrile (1.44 g, 6.70 mmol), tripotassium phosphate (3.55 g, 16.75 mmol), and PdCl₂(dppf) (0.81 g, 1.116 mmol) were taken together and degassed with nitrogen thrice. Dioxane (15 mL) was added and the reaction mixture was degassed again. The reaction mixture was stirred at 80° C. for 2 days. The reaction mixture was cooled to room temperature, diluted with EtOAc, and washed with water (3×). The organic layer was dried over Na₂SO₄, filtered and concentrated under vacuum. Purification using flash column chromatography (20% to 80% ethyl acetate/hexane gradient) provided 3'-amino-4'-(5-benzyl-2,5-diazabicyclo[2.2.1]heptan-2-yl)biphenyl-2-carbonitrile (1.2 g, 2.71 mmol).

¹H NMR (400 MHz, CDCl₃) δ ppm 7.72 (dd, 1H, J=0.8, 7.8 Hz), 7.56-7.61 (m, 1H), 7.49 (dd, 1H, J=0.80, 8.0 Hz), 7.30-7.40 (m, 5H), 7.23-7.26 (m, 1H), 7.03 (d, 1H, J=8.4 Hz), 6.92-6.96 (m, 2H), 3.88 (s, 2H), 3.81 (d, 2H, J=6.0 Hz), 3.61 (d, 1H, J=9.6 Hz), 3.14 (dd, 1H, J=9.8, 2.8 Hz), 2.88 (d, 2H, J=1.2 Hz), 1.97 (d, 1H, J=9.6 Hz), 1.87 (d, 1H, J=9.2 Hz). MS(ES): m/z=381 [M+H]⁺.

4-(5-Benzyl-2,5-diazabicyclo[2.2.1]heptan-2-yl)-2'-(1H-tetrazol-5-yl)biphenyl-3-amine A stirred solution of 3'-amino-4'-(5-benzyl-2,5-diazabicyclo[2.2.1]heptan-2-yl)-[1,1'-biphenyl]-2-carbonitrile (1.1 g, 2.89 mmol) and azidotributyltin (5.54 ml, 20.24 mmol) in toluene (11 ml) was refluxed for 2 days. The reaction mixture was cooled to room temperature and concentrated. The residue was dissolved in EtOAc, washed with 10% KF solution, water, brine, dried over Na₂SO₄ and concentrated The crude product was purified by flash column chromatography (0% to 50% MeOH/CHCl₃ gradient) to provide the title compound 4-(5-benzyl-2,5-diazabicyclo[2.2.1]heptan-2-yl)-2'-(1H-tetrazol-5-yl)biphenyl-3-amine (520 mg). ¹H NMR (400 MHz, DMSO-d₆) δ ppm 7.16-7.50 (m, 9H), 6.66 (d, 1H, J=8.0 Hz), 6.55 (d, 1H, J=2.0 Hz), 6.17 (dd, 1HJ=8.0, 1.6 Hz), 4.50 (s, 2H), 3.57 (s, 2H), 3.40 (d, 2H, J=10.0 Hz), 3.12 (d, 2H, J=8.0 Hz), 2.80 (s, 2H), 1.90(d, 1H, J=9.2 Hz), 1.79(d, 1H, J=9.2 Hz). MS(ES): m/z=424 [M+H]⁺. ,

Examples 50 to 53

Using the procedure of Example 45, the following compounds shown in Table 5 were prepared from 45A and the appropriate phenols:

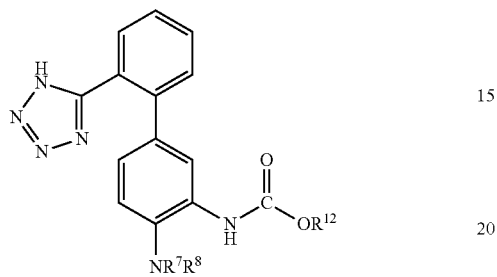

TABLE 4

| Ex. No. | Name | NR⁷R⁸ | R¹² | HPLC Ret Time | (M + H)⁺/ (M − 1) |
|---|---|---|---|---|---|
| 50 | 4-methoxyphenyl (4-(diisobutylamino)-2'-(1H-tetrazol-5-yl)-[1,1'-biphenyl]-3-yl)carbamate | diisobutylamino | 4-methoxyphenyl | 21.64ᵗ | 515.4 |
| 51 | benzo[d][1,3]dioxol-5-yl (4-(diisobutylamino)-2'-(1H-tetrazol-5-yl)-[1,1'-biphenyl]-3-yl) carbamate | diisobutylamino | benzo[d][1,3]dioxol-5-yl | 20.50ᵗ | 529.2 |
| 52 | 3-fluoro-4-methoxyphenyl (4-(diisobutylamino)-2'-(1H-tetrazol-5-yl)-[1,1'-biphenyl]-3-yl) carbamate | diisobutylamino | 3-fluoro-4-methoxyphenyl | 21.78ᵗ | 533.2 |
| 53 | 4-(benzyloxy)phenyl (4-(diisobutylamino)-2'-(1H-tetrazol-5-yl)-[1,1'-biphenyl]-3-yl)carbamate | diisobutylamino | 4-(benzyloxy)phenyl | 23.52ᵗ | 591.4 |

Examples 54 to 90

Using the methods described herein, the following additional compounds of the invention shown below in Table 5 were prepared.

TABLE 5

| Ex. No. | Structure | HPLC T$_r$ | (M + H)$^+$ |
|---|---|---|---|
| 54 | 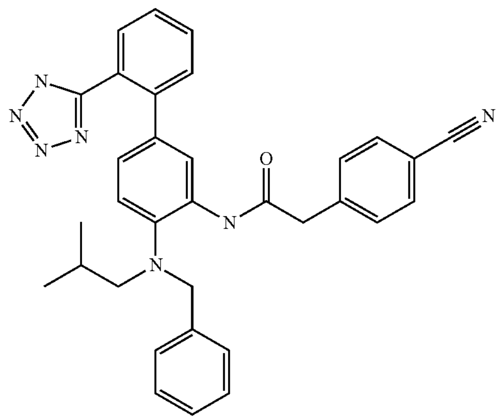 [SMILES: CC(C)CN(Cc1ccccc1)c1ccc(-c2ccccc2-c2nnn[nH]2)cc1NC(=O)Cc1ccc(C#N)cc1] | 1.96$^v$ | 542 |
| 55 | 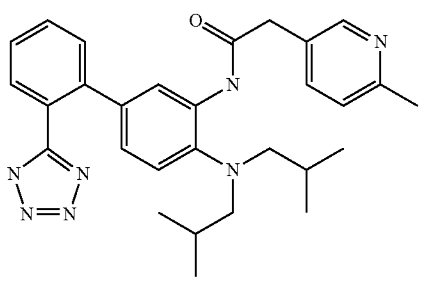 [SMILES: Cc1ccc(CC(=O)Nc2cc(-c3ccccc3-c3nnn[nH]3)ccc2N(CC(C)C)CC(C)C)cn1] | 1.46$^j$ | 498 |
| 56 | 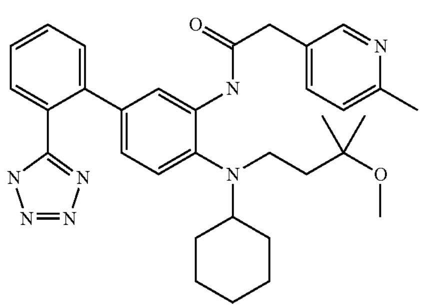 [SMILES: COC(C)(C)CCN(c1ccc(-c2ccccc2-c2nnn[nH]2)cc1NC(=O)Cc1ccc(C)nc1)C1CCCCC1] | 1.41$^j$ | 568 |
| 57 | 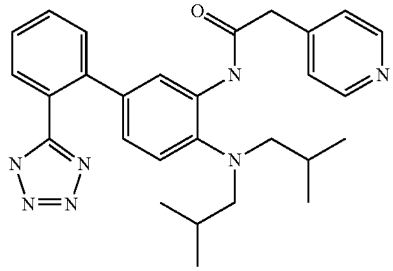 [SMILES: CC(C)CN(CC(C)C)c1ccc(-c2ccccc2-c2nnn[nH]2)cc1NC(=O)Cc1ccncc1] | 1.58$^k$ | 484 |

TABLE 5-continued

| Ex. No. | Structure | HPLC T$_r$ | (M + H)$^+$ |
|---|---|---|---|
| 58 | 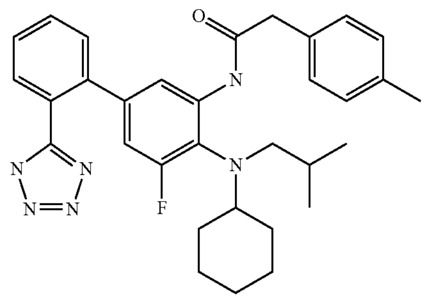 [SMILES: Cc1ccc(CC(=O)Nc2cc(-c3ccccc3-c3nnn[nH]3)cc(F)c2N(CC(C)C)C2CCCCC2)cc1] | 2.17$^j$ | 541 |
| 59 | 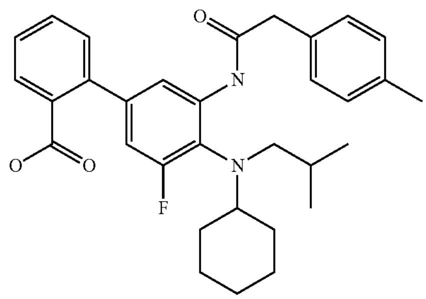 [SMILES: Cc1ccc(CC(=O)Nc2cc(-c3ccccc3C(=O)O)cc(F)c2N(CC(C)C)C2CCCCC2)cc1] | 2.25$^j$ | 517 |
| 60 | 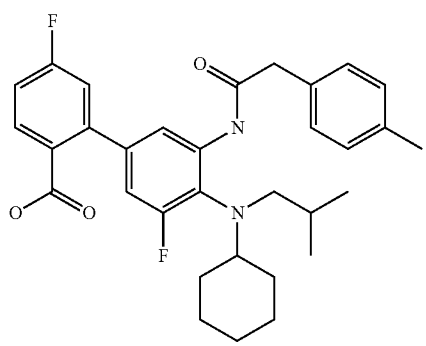 [SMILES: Cc1ccc(CC(=O)Nc2cc(-c3cc(F)ccc3C(=O)O)cc(F)c2N(CC(C)C)C2CCCCC2)cc1] | 2.26$^j$ | 535 |
| 61 | 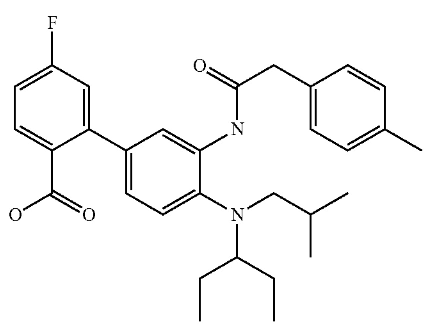 [SMILES: CCC(CC)N(CC(C)C)c1ccc(-c2cc(F)ccc2C(=O)O)cc1NC(=O)Cc1ccc(C)cc1] | 1.83$^j$ | 505 |
| 62 | 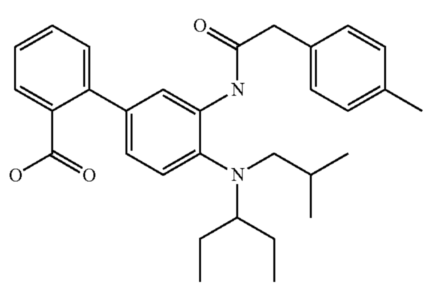 [SMILES: CCC(CC)N(CC(C)C)c1ccc(-c2ccccc2C(=O)O)cc1NC(=O)Cc1ccc(C)cc1] | 1.82$^j$ | 487 |

TABLE 5-continued

| Ex. No. | Structure | HPLC T$_r$ | (M + H)$^+$ |
|---|---|---|---|
| 63 | 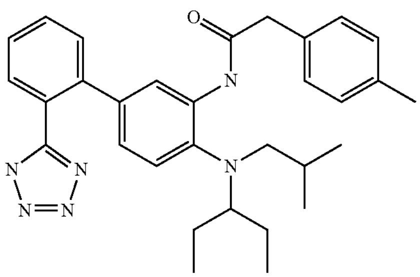 [SMILES: CCC(CC)N(CC(C)C)c1ccc(-c2ccccc2-c2nnn[nH]2)cc1NC(=O)Cc1ccc(C)cc1] | 1.80$^j$ | 511 |
| 64 | 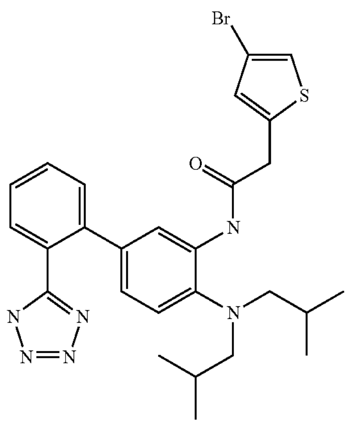 [SMILES: CC(C)CN(CC(C)C)c1ccc(-c2ccccc2-c2nnn[nH]2)cc1NC(=O)Cc1cc(Br)cs1] | 2.05$^j$ | 567 |
| 65 | 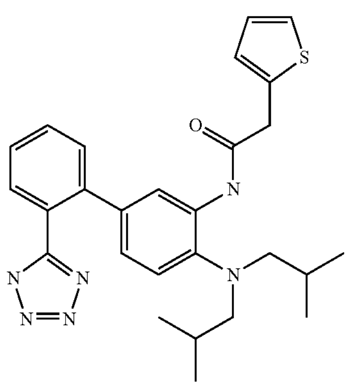 [SMILES: CC(C)CN(CC(C)C)c1ccc(-c2ccccc2-c2nnn[nH]2)cc1NC(=O)Cc1cccs1] | 2.27$^k$ | 489 |
| 66 | 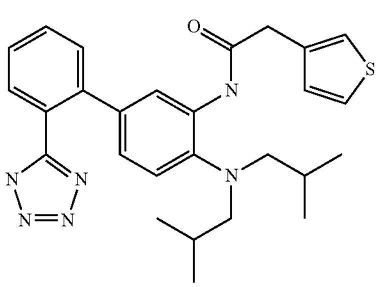 [SMILES: CC(C)CN(CC(C)C)c1ccc(-c2ccccc2-c2nnn[nH]2)cc1NC(=O)Cc1ccsc1] | 2.28$^k$ | 489 |

TABLE 5-continued

| Ex. No. | Structure | HPLC T$_r$ | (M + H)$^+$ |
|---|---|---|---|
| 67 | 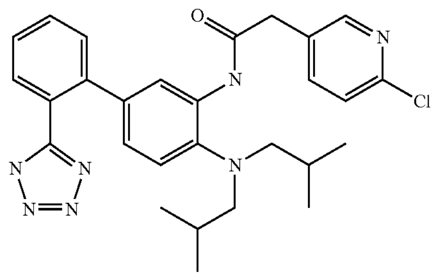 [SMILES: CC(C)CN(CC(C)C)c1ccc(-c2ccccc2-c2nnn[nH]2)cc1NC(=O)Cc1ccc(Cl)nc1] | 4.37$^l$ | 518 |
| 68 | 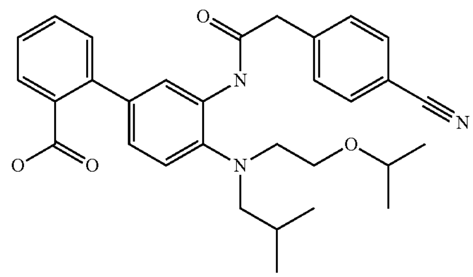 [SMILES: CC(C)CN(CCOC(C)C)c1ccc(-c2ccccc2C(=O)O)cc1NC(=O)Cc1ccc(C#N)cc1] | 2.19$^k$ | 514 |
| 69 | 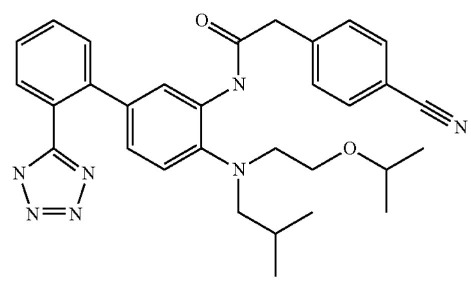 [SMILES: CC(C)CN(CCOC(C)C)c1ccc(-c2ccccc2-c2nnn[nH]2)cc1NC(=O)Cc1ccc(C#N)cc1] | 2.15$^k$ | 538 |
| 70 | 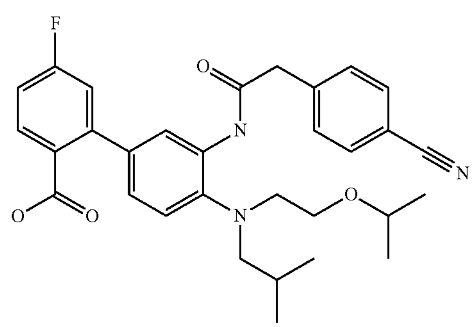 [SMILES: CC(C)CN(CCOC(C)C)c1ccc(-c2cc(F)ccc2C(=O)O)cc1NC(=O)Cc1ccc(C#N)cc1] | 1.77$^j$ | 532 |
| 71 | 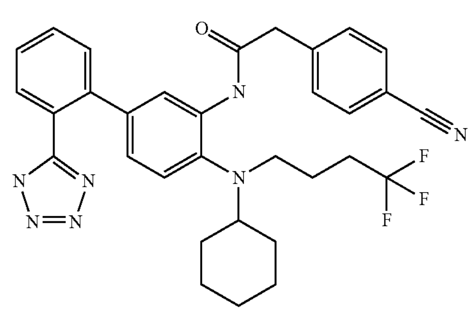 [SMILES: N#Cc1ccc(CC(=O)Nc2cc(-c3ccccc3-c3nnn[nH]3)ccc2N(CCCC(F)(F)F)C2CCCCC2)cc1] | 1.79$^j$ | 588 |

TABLE 5-continued

| Ex. No. | Structure | HPLC T$_r$ | (M + H)⁺ |
|---|---|---|---|
| 72 | 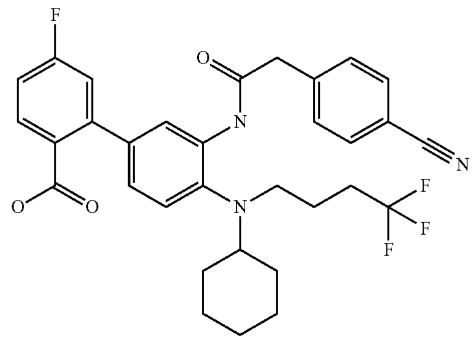 [SMILES: N#Cc1ccc(CC(=O)Nc2cc(-c3cc(F)ccc3C(=O)O)ccc2N(CCCC(F)(F)F)C2CCCCC2)cc1] | 1.81$^j$ | 582 |
| 73 | 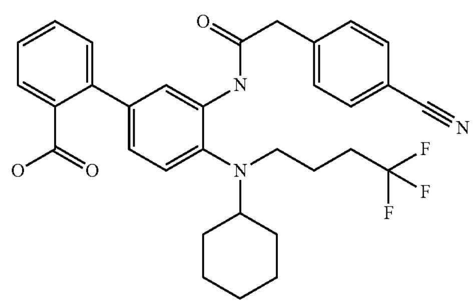 [SMILES: N#Cc1ccc(CC(=O)Nc2cc(-c3ccccc3C(=O)O)ccc2N(CCCC(F)(F)F)C2CCCCC2)cc1] | 2.11$^k$ | 564 |
| 74 | 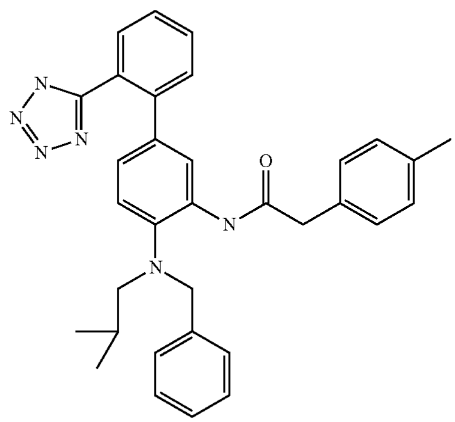 [SMILES: Cc1ccc(CC(=O)Nc2cc(-c3ccccc3-c3nnn[nH]3)ccc2N(Cc2ccccc2)CC(C)C)cc1] | 2.07$^v$ | 529 (M − H)⁻ |
| 75 | 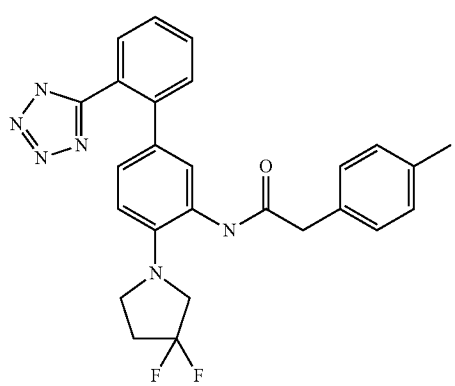 [SMILES: Cc1ccc(CC(=O)Nc2cc(-c3ccccc3-c3nnn[nH]3)ccc2N2CCC(F)(F)C2)cc1] | 1.82$^v$ | 473 (M − H)⁻ |

TABLE 5-continued

| Ex. No. | Structure | HPLC T$_r$ | (M + H)$^+$ |
|---|---|---|---|
| 76 | 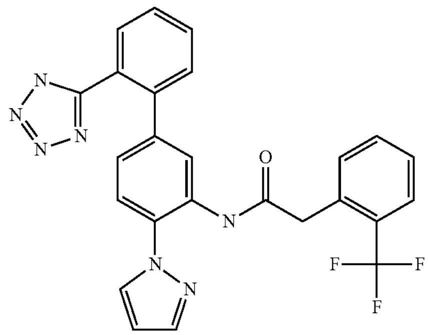 [SMILES: O=C(Cc1ccccc1C(F)(F)F)Nc1cc(-c2ccccc2-c2nnn[nH]2)ccc1-n1cccn1] | 1.78$^v$ | 490 |
| 77 | 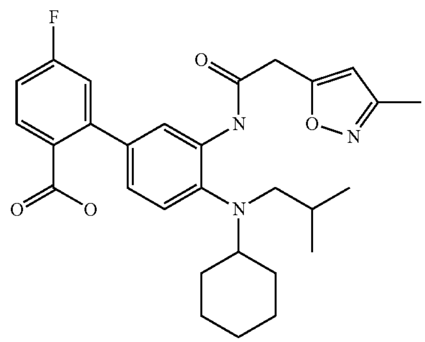 [SMILES: Cc1cc(CC(=O)Nc2cc(-c3cc(F)ccc3C(=O)O)ccc2N(CC(C)C)C2CCCCC2)on1] | 1.66$^j$ | 508 |
| 78 | 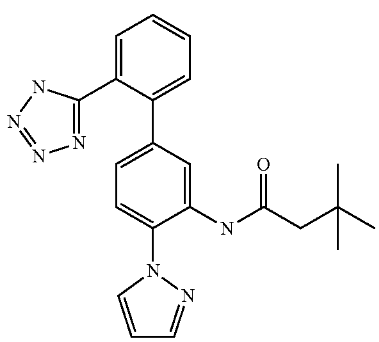 [SMILES: CC(C)(C)CC(=O)Nc1cc(-c2ccccc2-c2nnn[nH]2)ccc1-n1cccn1] | 1.78$^v$ | 400 (M − H)$^-$ |
| 79 | 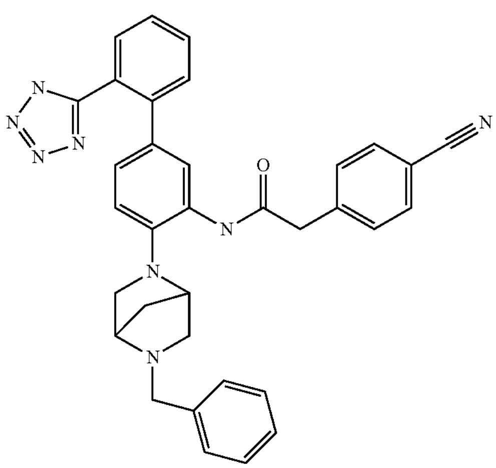 [SMILES: N#Cc1ccc(CC(=O)Nc2cc(-c3ccccc3-c3nnn[nH]3)ccc2N2CC3CC2CN3Cc2ccccc2)cc1] | 1.68$^v$ | 567 |

TABLE 5-continued

| Ex. No. | Structure | HPLC T$_r$ | (M + H)$^+$ |
|---------|-----------|------------|-------------|
| 80 | 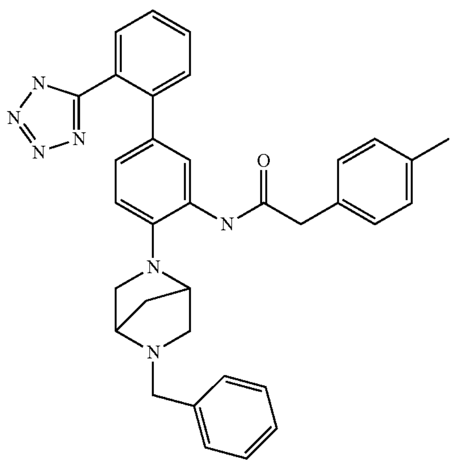 [SMILES: Cc1ccc(CC(=O)Nc2cc(-c3ccccc3-c3nnn[nH]3)ccc2N2CC3CC2CN3Cc2ccccc2)cc1] | 1.76$^v$ | 556 |
| 81 | 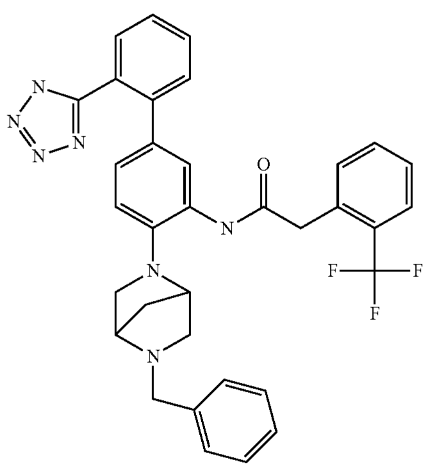 [SMILES: O=C(Cc1ccccc1C(F)(F)F)Nc1cc(-c2ccccc2-c2nnn[nH]2)ccc1N1CC2CC1CN2Cc1ccccc1] | 1.78$^v$ | 608 (M − H)$^−$ |
| 82 | 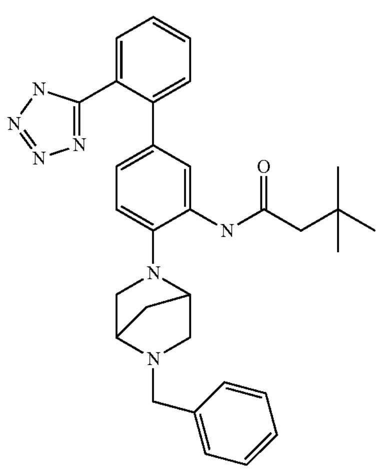 [SMILES: CC(C)(C)CC(=O)Nc1cc(-c2ccccc2-c2nnn[nH]2)ccc1N1CC2CC1CN2Cc1ccccc1] | 1.65$^v$ | 522 |

TABLE 5-continued
| Ex. No. | Structure | HPLC T$_r$ | (M + H)$^+$ |
|---|---|---|---|
| 83 | 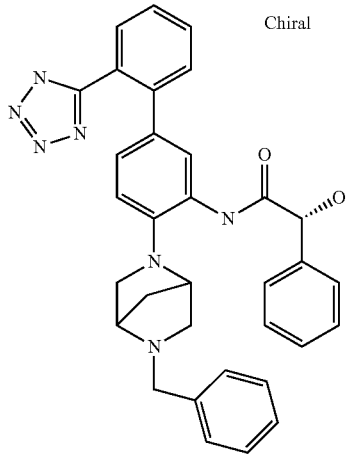 [SMILES: O=C(Nc1cc(-c2ccccc2-c2nnn[nH]2)ccc1N1CC2CC1CN2Cc1ccccc1)[C@H](O)c1ccccc1] Chiral | 1.54$^v$ | 558 |
| 84 | 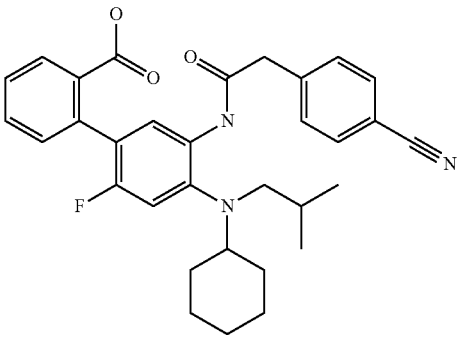 [SMILES: CC(C)CN(c1cc(F)c(-c2ccccc2C(=O)O)cc1NC(=O)Cc1ccc(C#N)cc1)C1CCCCC1] | 1.96$^j$ | 528 |
| 85 | 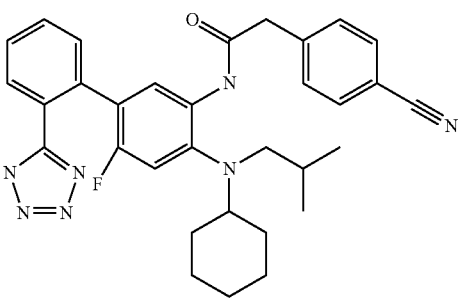 [SMILES: CC(C)CN(c1cc(F)c(-c2ccccc2-c2nnn[nH]2)cc1NC(=O)Cc1ccc(C#N)cc1)C1CCCCC1] | 1.88$^j$ | 552 |
| 86 | 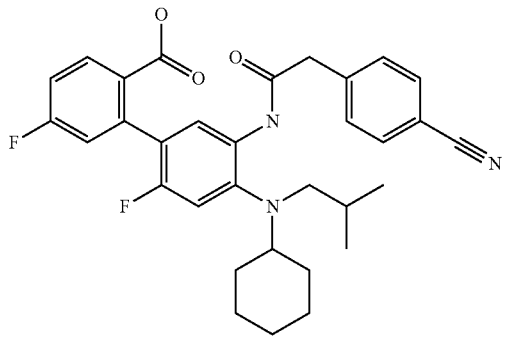 [SMILES: CC(C)CN(c1cc(F)c(-c2cc(F)ccc2C(=O)O)cc1NC(=O)Cc1ccc(C#N)cc1)C1CCCCC1] | 1.98$^j$ | 586 |

TABLE 5-continued

| Ex. No. | Structure | HPLC T$_r$ | (M + H)$^+$ |
|---------|-----------|------------|-------------|
| 87 | 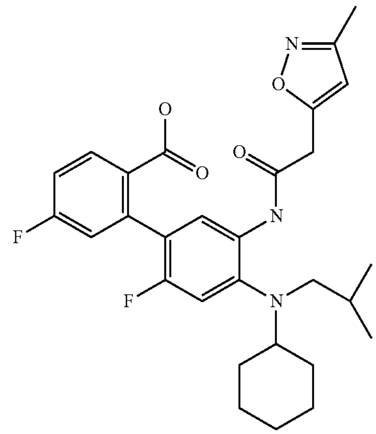 [SMILES: Cc1cc(CC(=O)Nc2cc(-c3cc(F)ccc3C(=O)O)c(F)cc2N(CC(C)C)C2CCCCC2)on1] | 1.83$^j$ | 526 |

Evaluation of Biological Activity

Exemplary compounds were tested for inhibition of IDO activity. Experimental procedures and results are provided below.

IDO Kynurenine Assay with Human IDO1/HEK293 Cells

Human IDO1/HEK293 cells were seeded at 10,000 cells per 50 uL per well with RPMI/phenol red free media contains 10% FBS in a 384-well black wall clear bottom tissue culture plate (Matrix Technologies LLC) 125 nL of certain concentration of compound was then added to each well using ECHO liquid handling systems. The cells were incubated for 20 hours in 37° C. incubator with 5% $CO_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

IDO Kynurenine Assay with Hela Cells

Hela cells were seeded at 30,000 cells per well in 40 ul RPMI/phenol red free media contains 10% FBS in a 384-well black wall clear bottom tissue culture plate (Matrix Technologies LLC). 270 nl of certain concentration of compound was then added to each well using ECHO liquid handling systems. 40 ul of IFNγ (R&D, 285-IF-100) at final concentration of 10 ng/ml was then added to column 2-24 with media to column 1 as control. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound IC50 values were calculated using the counts of no IFNγ control as one hundred percent inhibition, and counts of no compound but DMSO treatment as zero percent inhibition.

Results of the IDO assays are shown in the table below.

| Example # | HEK human IDO-1 (IC50, uM) | Hela Cells LLE_IDO_ABS_DR (IC50, uM) |
|---|---|---|
| 1 | | 0.01 |
| 2 | | 5.02E−03 |
| 3 | | 0.02 |
| 4 | | 0.01 |
| 5 | | 0.04 |
| 6 | | 0.05 |
| 7 | | 0.13 |
| 8 | | 0.94 |
| 9 | | 0.02 |
| 10 | | 7.09E−03 |
| 11 | | 4.05E−03 |
| 12 | 2.99E−03 | 0.01 |
| 13 | | 1.33 |
| 14 | | 0.02 |
| 15 | | 0.09 |
| 16 | | 8.90E−03 |
| 17 | | 4.42E−03 |
| 18 | | 0.04 |
| 19 | | 0.02 |
| 20 | | 9.11E−03 |
| 21 | | 0.52 |
| 22 | | 1.19 |
| 23 | | 0.28 |
| 24 | | 0.08 |
| 25 | | 0.02 |
| 26 | | 0.05 |
| 27 | | 0.16 |
| 28 | | 0.09 |
| 29 | | 0.06 |
| 30 | | 0.30 |
| 31 | | 0.07 |
| 32 | | 4.01 |
| 33 | | 0.50 |
| 34 | | 0.25 |
| 35 | | 0.27 |
| 36 | | 0.40 |

-continued

| Example # | HEK human IDO-1 (IC50, uM) | Hela Cells LLE_IDO_ABS_DR (IC50, uM) |
|---|---|---|
| 37 | | 1.28 |
| 38 | | 2.52 |
| 39 | | 0.05 |
| 40 | | 0.16 |
| 41 | | 1.83 |
| 42 | | 0.50 |
| 43 | | 5.09E-03 |
| 44 | | 0.08 |
| 45 | | 3.90 |
| 46 | | 0.23 |
| 47 | | 0.47 |
| 48 | | 1.61 |
| 49 | 3.17E-03 | |
| 50 | | 0.12 |
| 51 | | 3.91 |
| 52 | | 6.56 |
| 53 | | 3.25 |
| 54 | | 0.01 |
| 55 | 0.12 | |
| 56 | 7.44 | |
| 57 | 0.36 | |
| 58 | 0.01 | |
| 59 | 0.08 | |
| 60 | 0.03 | |
| 61 | 0.02 | |
| 62 | 0.02 | |
| 63 | 4.37E-03 | |
| 64 | 0.04 | |
| 65 | 0.02 | |
| 66 | 0.02 | |
| 67 | 0.02 | |
| 68 | 4.81 | |
| 69 | 0.17 | |
| 70 | 2.93 | |
| 71 | 0.27 | |
| 72 | 1.86 | |
| 73 | 2.11 | |
| 74 | 0.01 | 3.06E-03 |
| 75 | | 1.81 |
| 76 | | 0.28 |
| 77 | 0.30 | |
| 78 | | 4.44 |
| 79 | | 2.51 |
| 80 | 5.13E-03 | 8.44E-03 |
| 81 | 0.11 | 0.10 |
| 82 | | 3.61 |
| 83 | | 8.92 |
| 84 | 0.03 | |
| 85 | 0.04 | |
| 86 | 0.02 | |
| 87 | 0.14 | |

What is claimed is:

1. A compound of formula (II)

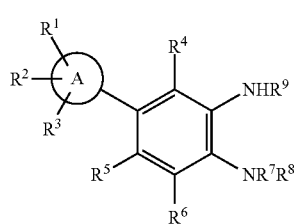

(II)

wherein:

$A$ is phenyl optionally substituted with halo, $R^1$ is COOH or tetrazol-5-yl;

$R^2$ and $R^3$ are independently H;

$R^4$ and $R^5$ are independently H or halo;

$R^6$ is H;

$R^7$ and $R^8$ are independently H, $C_1$-$C_6$ alkyl optionally substituted with halogen, $C_3$-$C_8$ cycloalkyl, $C_3$-$C_8$ cycloalkenyl, aryl, $C_1$-$C_6$ alkoxyl optionally substituted with $C_1$-$C_6$ alkyl, $C_3$-$C_8$ cycloalkyl optionally substituted with $C_1$-$C_6$ alkyl, and aryl $C_1$-$C_6$ alkyl, provided that only one of $R^7$ and $R^8$ is H, or $R^7$ and $R^8$ are taken together with the nitrogen to which they are attached to form $R^9$ is or —COOR$^{12}$;

$R^{10}$ is aryl optionally substituted with $C_1$-$C_6$ alkyl, CN, haloalkyl, or halogen, $C_1$-$C_6$ alkyl, 5- to 7-membered monocyclic heteroaryl optionally substituted with $C_1$-$C_6$ alkyl, halo and CN;

$R^{11}$ is H or OH;

$R^{12}$ is aryl optionally substituted with $C_1$-$C_6$ alkyl, nitro, halogen, alkoxyl, aryloxyl or benzodioxolyl;

and/or a stereoisomer, a tautomer or a pharmaceutically acceptable salt thereof.

2. The compound as defined in claim 1 wherein $A$ is phenyl, and/or a stereoisomer, a tautomer or a pharmaceutically acceptable salt thereof.

3. The compound as defined in claim 1 wherein:

$R^1$ is tetrazol-5-yl or COOH;

$R^2$ is H and $R^3$ is H, and/or a stereoisomer, a tautomer or a pharmaceutically acceptable salt thereof.

4. The compound as defined in claim 1 wherein:
R[7] and R[8] are independently optionally substituted $C_1$-$C_6$ alkoxyl, or optionally substituted $C_3$-$C_8$ cycloalkyl;
or R[7] and R[8] are taken together with the nitrogen to which they are attached to form

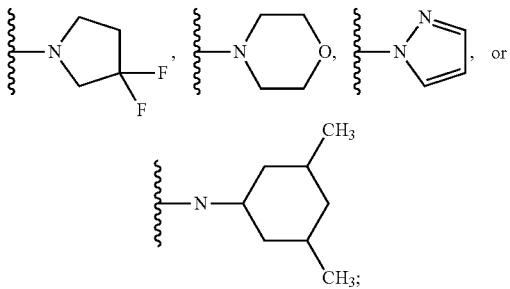

and
R[9] is

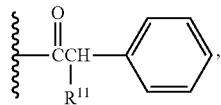

or —COOR[12];
R[11] is H; and
R[12] is naphthyl, nitroaryl, phenyl, $C_1$-$C_6$ alkylphenyl, $C_1$-$C_6$ alkoxyphenyl,

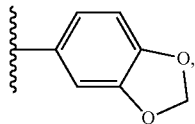

$C_1$-$C_6$ alkoxy(halo)phenyl, halophenyl, or phenyl-$C_1$-$C_6$-alkoxyphenyl;

and/or a stereoisomer, a tautomer or a pharmaceutically acceptable salt thereof.

5. A compound selected from the group consisting of 4'-(Diisobutylamino)-5-fluoro-3'-(2-p-tolylacetamido)biphenyl-2-carboxylic acid; N-(4-(Diisobutylamino)-2'-(1H-tetrazol-5-yl)biphenyl-3-yl)-2-p-tolylacetamide; N,N-(4-(Benzyl(isobutyl)amino)-2'-(1H-tetrazol-5-yl)biphenyl-3-yl)-2-(2-(trifluoromethyl)phenyl)acetamide; 4'-(diisobutylamino)-3'-(2-p-tolylacetamido)biphenyl-2-carboxylic acid; 4'-(cyclohexyl(isobutyl)amino)-3'-(2-(2-fluorophenyl)acetamido)biphenyl-2-carboxylic acid; 4'-(cyclohexyl(isobutyl)amino)-5-fluoro-3'-(2-(2-fluorophenyl)acetamido)biphenyl-2-carboxylic acid; and N-(4-(cyclohexyl(isobutyl)amino)-2'-(1H-tetrazol-5-yl)biphenyl-3-yl)-2-(2-(trifluoromethyl) phenyl)acetamide and/or a stereoisomer, a tautomer or a pharmaceutically acceptable salt thereof.

6. The compound that is 4'-(Diisobutylamino)-5-fluoro-3'-(2-p -tolylacetamido)biphenyl-2-carboxylic acid; N-(4-(Diisobutylamino)-2'-(1H-tetrazol-5-yl)biphenyl-3-yl)-2-p-tolylacetamide or a pharmaceutically acceptable salt thereof.

7. The compound that is N-(4-(Diisobutylamino)-2'-(1H-tetrazol-5-yl)biphenyl-3-yl)-2-p-tolylacetamide or a pharmaceutically acceptable salt thereof.

8. The compound that is N,N-(4-(Benzyl(isobutyl)amino)-2'-(1H-tetrazol-5-yl)biphenyl-3-yl)-2-(2-(trifluoromethyl)phenyl)acetamide or a pharmaceutically acceptable salt thereof.

9. The compound that is 4'-(cyclohexyl(isobutyl)amino)-3'-(2-(2-fluorophenyl)acetamido)biphenyl-2-carboxylic acid or a pharmaceutically acceptable salt thereof.

10. A pharmaceutical composition comprising one or more compounds according to claim 1 and a pharmaceutically acceptable carrier or diluent.

* * * * *